United States Patent
Kettle et al.

(10) Patent No.: US 10,273,227 B2
(45) Date of Patent: Apr. 30, 2019

(54) C5-ANILINOQUINAZOLINE COMPOUNDS AND THEIR USE IN TREATING CANCER

(71) Applicant: AstraZeneca AB, Södertälje (SE)

(72) Inventors: Jason Kettle, Cambridge (GB); Stuart Pearson, Cambridge (GB); Martin Packer, Cambridge (GB); James Smith, Cambridge (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 15/963,122

(22) Filed: Apr. 26, 2018

(65) Prior Publication Data

US 2018/0312490 A1   Nov. 1, 2018

Related U.S. Application Data

(60) Provisional application No. 62/490,859, filed on Apr. 27, 2017.

(51) Int. Cl.
| | |
|---|---|
| *A61K 31/517* | (2006.01) |
| *A61K 31/4192* | (2006.01) |
| *C07D 403/12* | (2006.01) |
| *C07D 403/10* | (2006.01) |
| *A61P 35/00* | (2006.01) |
| *C07D 405/14* | (2006.01) |

(52) U.S. Cl.
CPC ............ *C07D 403/12* (2013.01); *A61P 35/00* (2018.01); *C07D 405/14* (2013.01); *A61K 2121/00* (2013.01)

(58) Field of Classification Search
CPC .. C07D 403/12; C07D 403/10; A61K 31/517; A61K 31/4192; A61P 35/00
USPC .................. 544/284, 293; 514/266.4, 266.23
See application file for complete search history.

(56) References Cited

U.S. PATENT DOCUMENTS

| 7,709,479 B1 | 5/2010 | Mortlock et al. |
| 2003/0087907 A1 | 5/2003 | Kubo et al. |
| 2006/0178382 A1 | 8/2006 | Mortlock et al. |

FOREIGN PATENT DOCUMENTS

| CN | 103254142 A1 | 8/2013 |
| CN | 104130200 A1 | 11/2014 |
| WO | 96/09294 A1 | 3/1996 |
| WO | 97/03069 A1 | 1/1997 |
| WO | 01/021596 A1 | 3/2001 |
| WO | 2006/040520 A1 | 4/2006 |
| WO | 2006/116713 A1 | 11/2006 |
| WO | 2007/099326 A1 | 9/2007 |
| WO | 2007/089307 A2 | 7/2008 |
| WO | 2008/089310 A2 | 7/2008 |
| WO | 2009/140549 A1 | 11/2009 |
| WO | 2011/153553 A2 | 12/2011 |
| WO | 2014/181287 A1 | 11/2014 |

OTHER PUBLICATIONS

Antonescu et al., "Acquired Resistance to Imatinib in Gastrointestinal Stromal Tumor Occurs Through Secondary Gene Mutation", Clin. Cancer Res., Jun. 2005, 11, pp. 4182-4184.
Babaei et al., "Receptor tyrosine kinase (c-Kit) inhibitors: a potential therapeutic target in cancer cells", Drug Design, Development and Therapy, 2016, 10, pp. 2443-2459.
Bahlawane et al., "Constitutive activation of oncogenic PDGFRα-mutant proteins occurring in GIST patients induces receptor mislocalisation and alters PDGFRα signaling charactetistics", Cell Communication and Signaling, 2015, 13:21, pp. 1-21.
Barnett, et al., Gastrointestinal Stromal Tumors Molecular Markers and Genetic Subtypes:, Hematol. Oncol. Clin. N. Am., 2013, 27, pp. 871-888.
Blanke et al., "Long-Term Results from a Randomized Phase II Trial of Standard-Versus Higher-Dose Imatinib Mesylate for Patients with Unresectable or Metastatic Gastrointestinal Stromal Tumors Expressing KIT", J. Clin. Oncol., Feb. 2008, 26:4, pp. 620-625.
Demetri et al., "Efficacy and Safety of Imatinib Mesylate in Advanced Gastrointestinal Stromal Tumors", N. Engl. J. Med., 2002, 347:7, pp. 472-480.
Demetri et al., "Efficacy and safety of sunitinib in patients with advanced gastrointestinal stromal tumor after failure of imatinib: a randomized controlled trial", The Lancet, 2006, 368, pp. 1329-1338.
Demetri et al., "Efficacy and safety of regorafenib for advanced gastrointestinal stromal tumours after failure of imatinib and sunitinib (GRID): an international, multicenter, randomized, placebo-controlled, phase 3 trial", The Lancet, 2013, 381, pp. 295-302.
Dinitto et al., "Function of activation loop tyrosine phosphorylation in the mechanism of c-Kit auto-activation and its implication in sunitinib resistance", J. Biochem., 2010, 147:4, pp. 601-609.

(Continued)

*Primary Examiner* — Matthew P Coughlin
*Assistant Examiner* — Sagar Patel

(57) ABSTRACT

The invention concerns compounds of Formula (I):

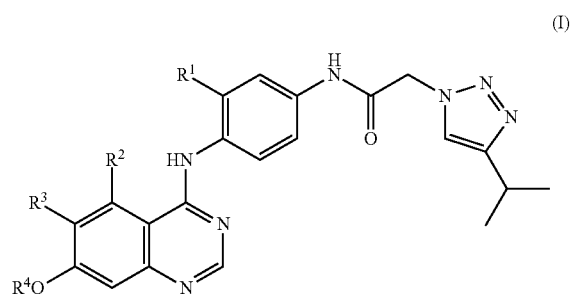

(I)

or pharmaceutically acceptable salts thereof, wherein $R^1$, $R^2$, $R^3$ and $R^4$ have any of the meanings hereinbefore defined in the description; process for their preparation; pharmaceutical compositions containing them and their use in treating KIT mediated diseases.

24 Claims, 10 Drawing Sheets

(56) References Cited

OTHER PUBLICATIONS

Fletcher, "KIT Oncogenic Mutations: Biologic Insights, Therapeutic Advances, and Future Directions", Cancer Res., 2016, 76:21, pp. 6140-6142.

Gastrointestinal Stromal Tumor Meta-Analysis Group (MetaGIST), "Comparison of Two Doses of Imatinib for the Treatment of Unresectable or Metastatic Gastrointertinal Stromal Tumors: A Meta-Analysis of 1,640 Patients", J. Clin. Oncol., 2010, 28, pp. 1247-1253.

Heinrich et al., "Molecular Correlates of Imatinib Resistance in Gastrointestinal Stromal Tumors", J. Clin. Oncol., 2006, 24:29, pp. 4764-4774.

Heinrich et al., "Primary and Secondary Kinase Genotypes Correlate With the Biological and Clinical Activity of Sunitinib in Imatinib-Resistant Gastrointestinal Stromal Tumor", J. Clin. Oncol., 2008, 26:33, pp. 5352-5359.

Hirota et al., Gain-of-Function Mutations of c-kit in Human Gastrointestinal Stromal Tumors:, Science, 1998, 279, pp, 577-580.

International Search Report and Written Opinion for PCT/EP2018/060800 dated Jul. 6, 2018.

International Search Report and Written Opinion for PCT/EP2018/060798 dated Jun. 20, 2018.

Lemmon, et al., "A New Twist in the Transmembrane Signaling Tool-Kit", Cell, 2007, 130, pp. 213-215.

Lennartsson et al., "Stem Cell Factor Receptor/c-KOT: From Basic Science to Clinical Implications", Physiol. Rev., 2012, 92, pp. 1619-1649.

Plé et al., "Discovery of AZD2932, a new Quinazoline Ether Inhibitor with high affinity for VEGFR-2 and PDGFR tyrosine kinases", Bioorganic & Medicinal Chemistry Letters, 2012, 22, pp. 262-266.

Rao et al., "Synthesis, Antitumor Evaluation and Docking Study of Novel 4-Anilinoquinazoline Derivatives as Potential Epidermal Growth Factor Receptor (EGFR) Inhibitors", Chem. Med. Chem., 2013, 8, pp. 928-933.

Verstraete et al., "Extracellular assembly and activation principles of oncogenic class III receptor tyrosine kinases", Nat. Rev. Cancer, 2012, 12, pp. 753-766.

Verweij et al., "Progression-free stuvival in gastrointestinal stromal tumours with high-dose imatinib: randomised trial", The Lancet, 2004, 364, pp. 1127-1134.

Yin et al., "Design, synthesis and biological evaluation of 4-anilinoquinazoline derivatives as new c-myc G-quadruplex ligands", European Journal of Medicinal Chemistry, 2016, 122, pp. 264-279.

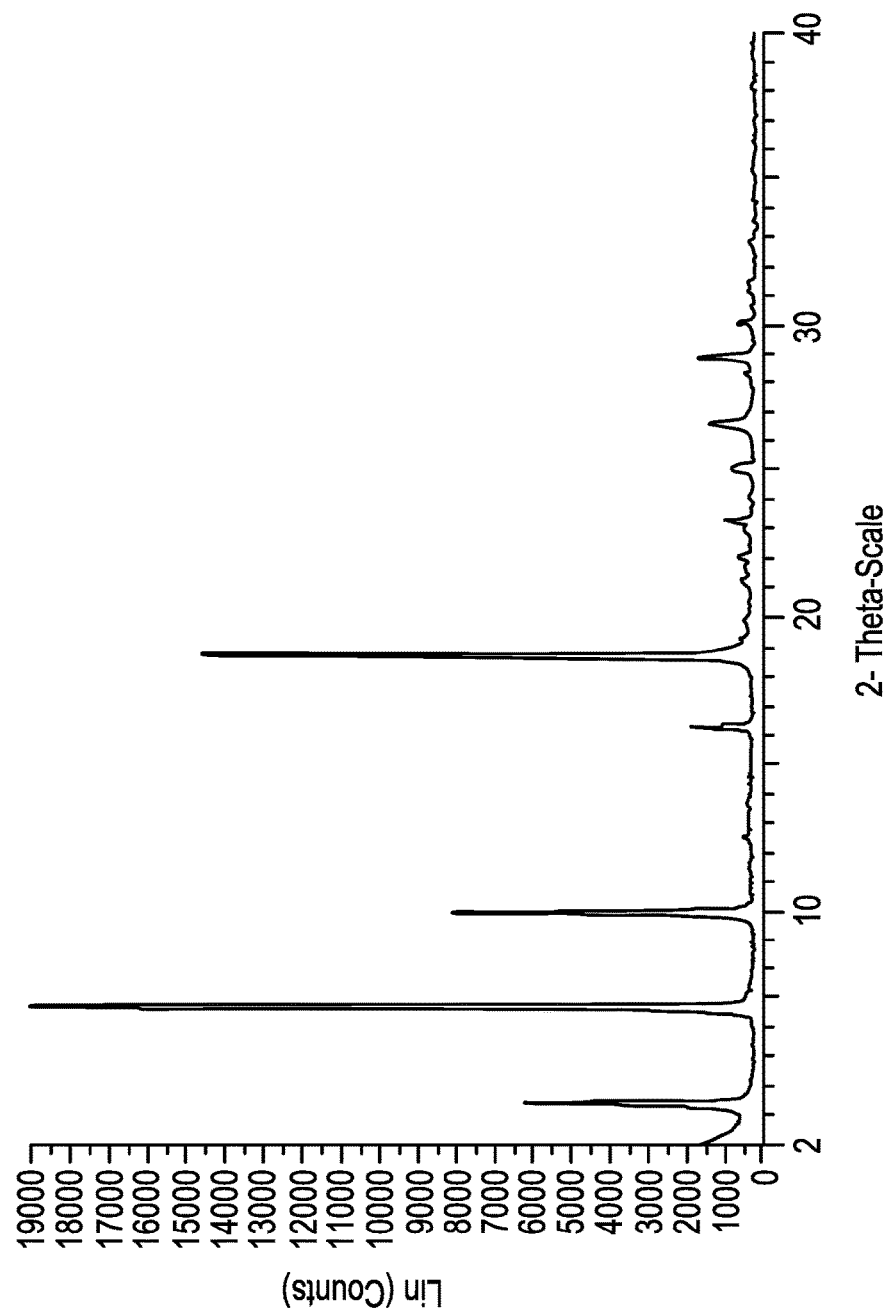
Figure 1: X-ray Powder Diffraction Pattern of Compound X Form A

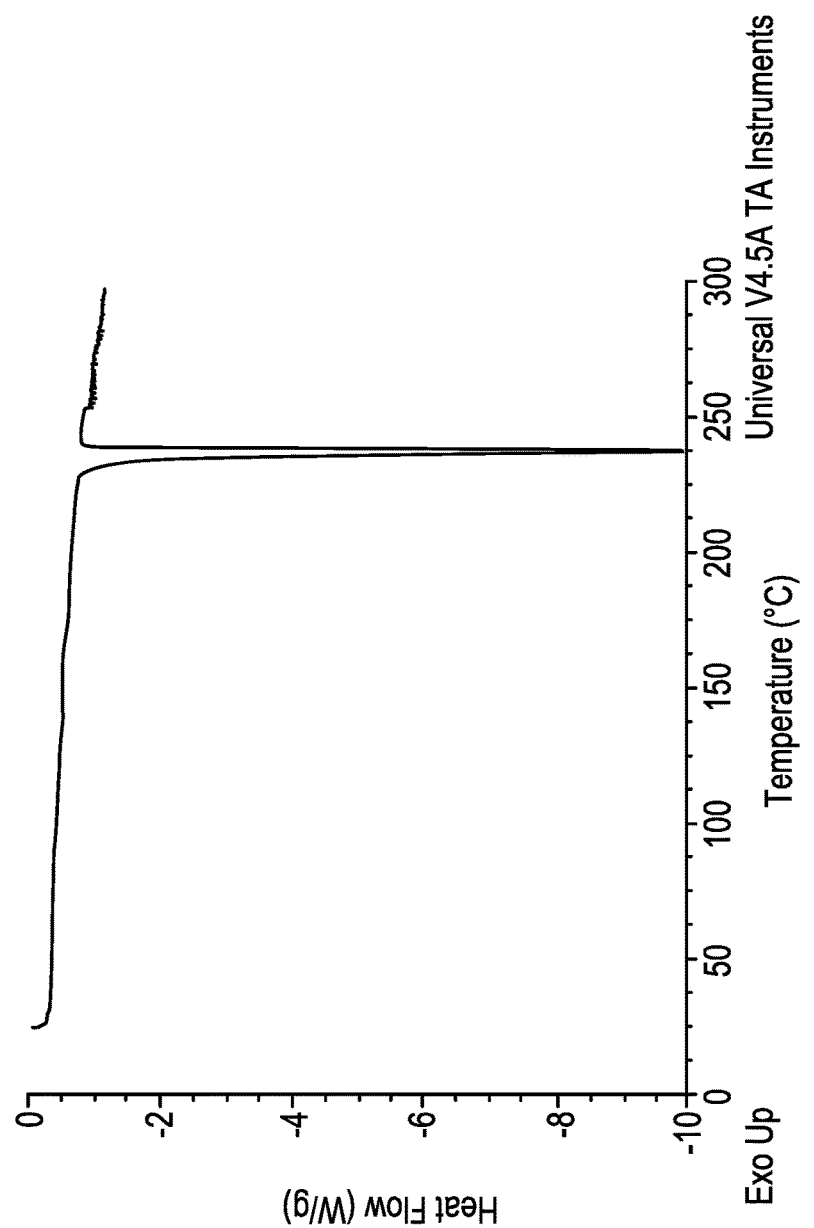
Figure 2: DSC Thermogram of Compound X Form A

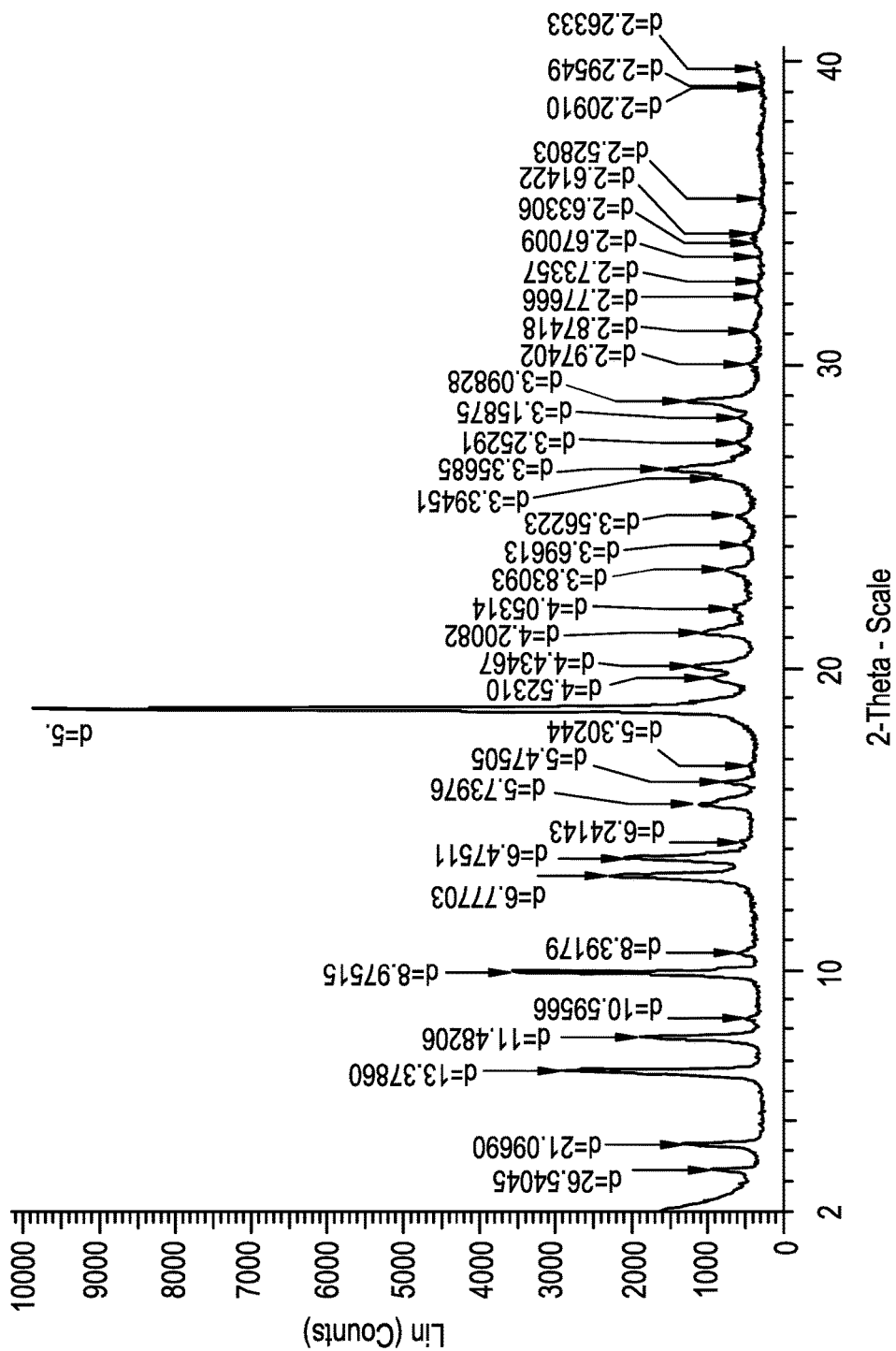
Figure 3: X-ray Powder Diffraction Pattern of Compound X Form B

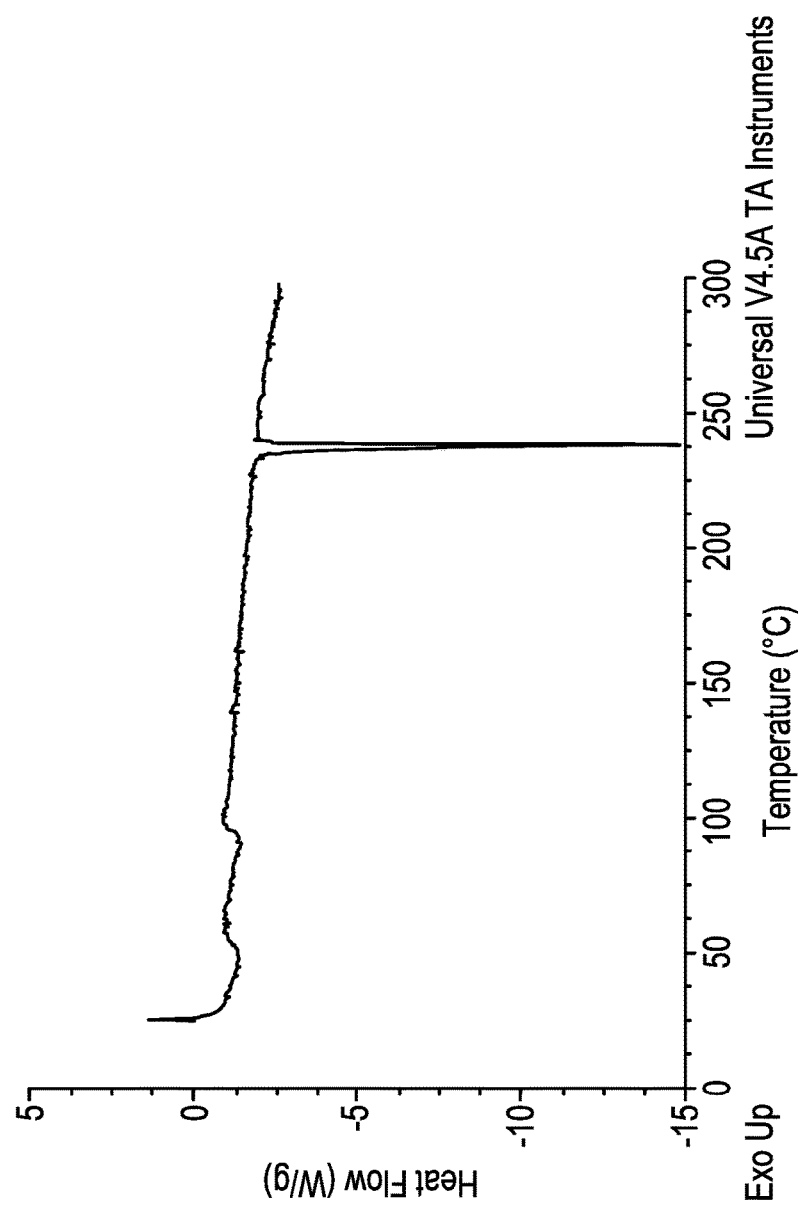
Figure 4: DSC Thermogram of Compound X Form B

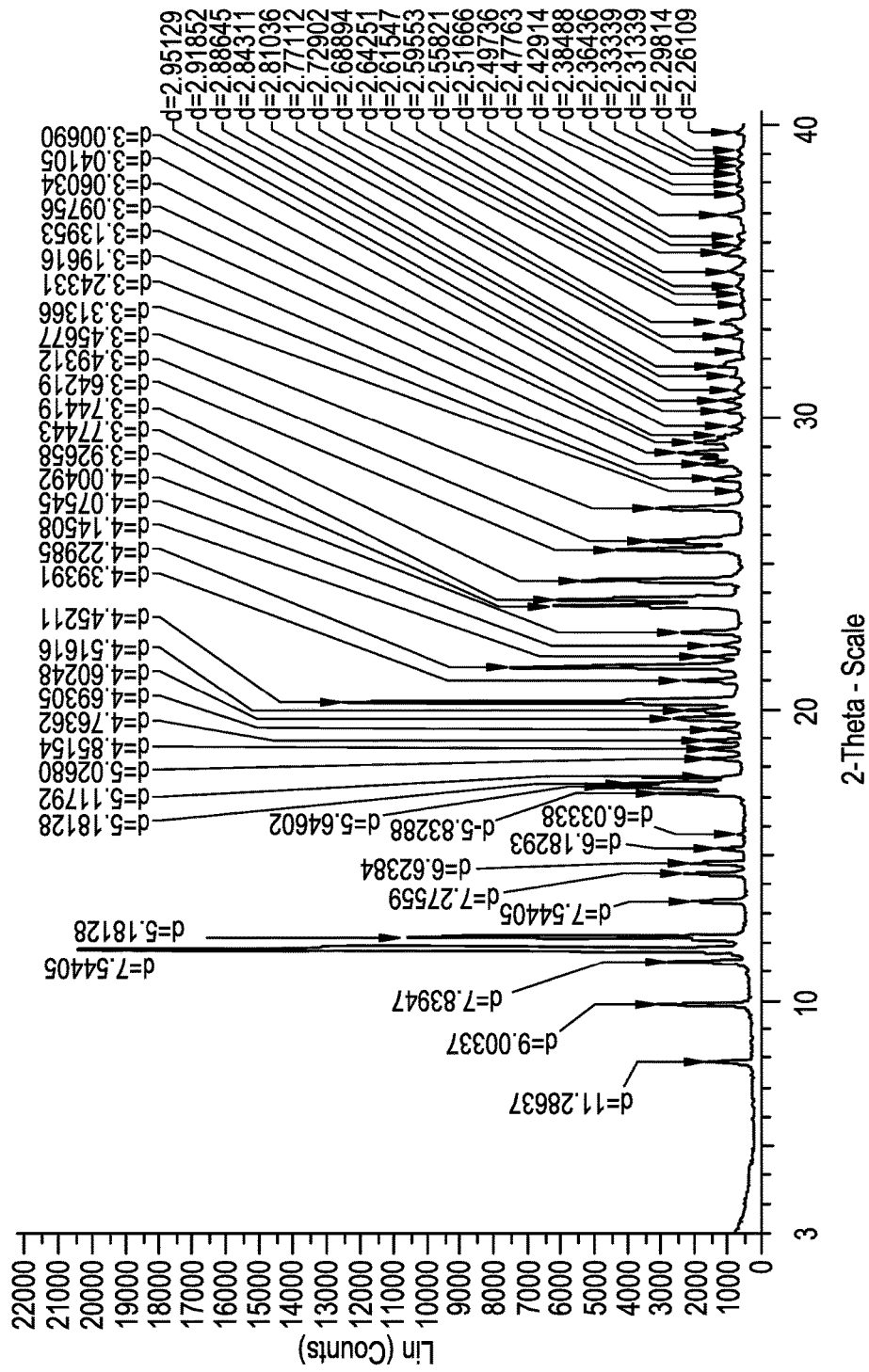
Figure 5: X-ray Powder Diffraction Pattern of Tosylate Salt Y Form A

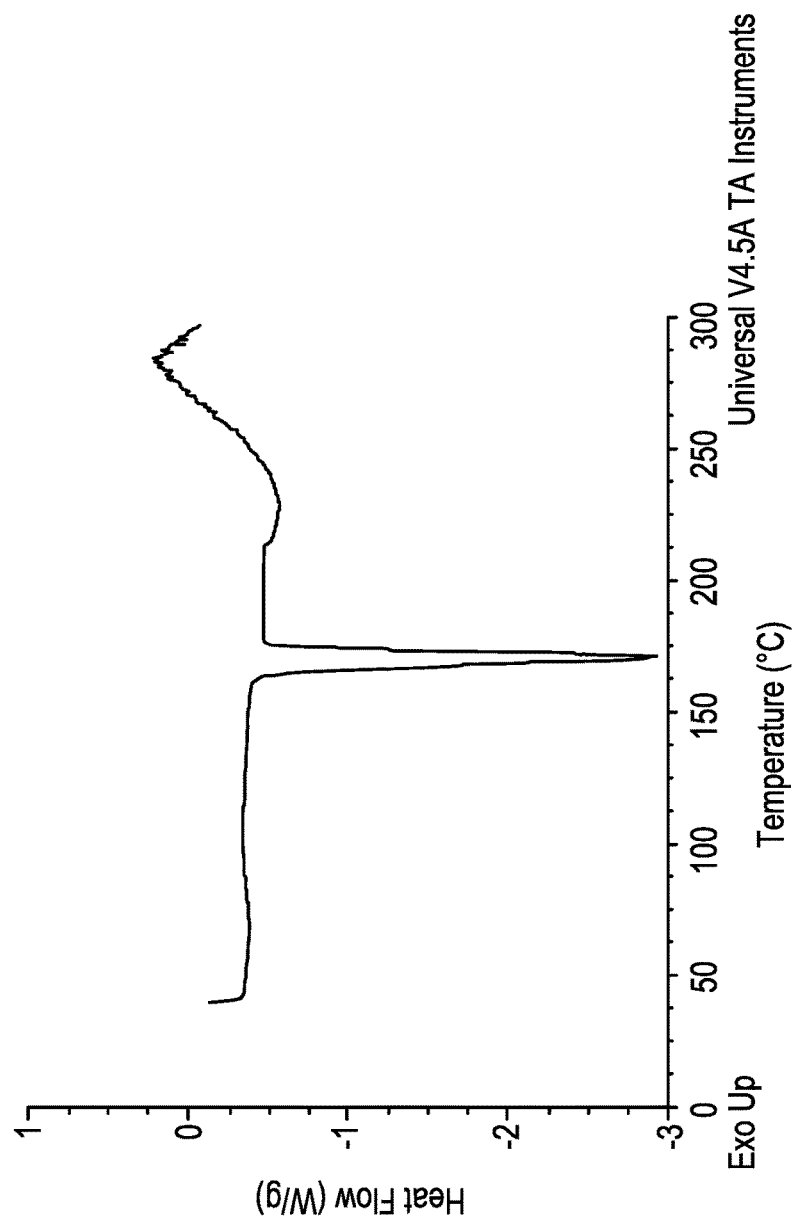
Figure 6: DSC Thermogram of Tosylate Salt Y Form A

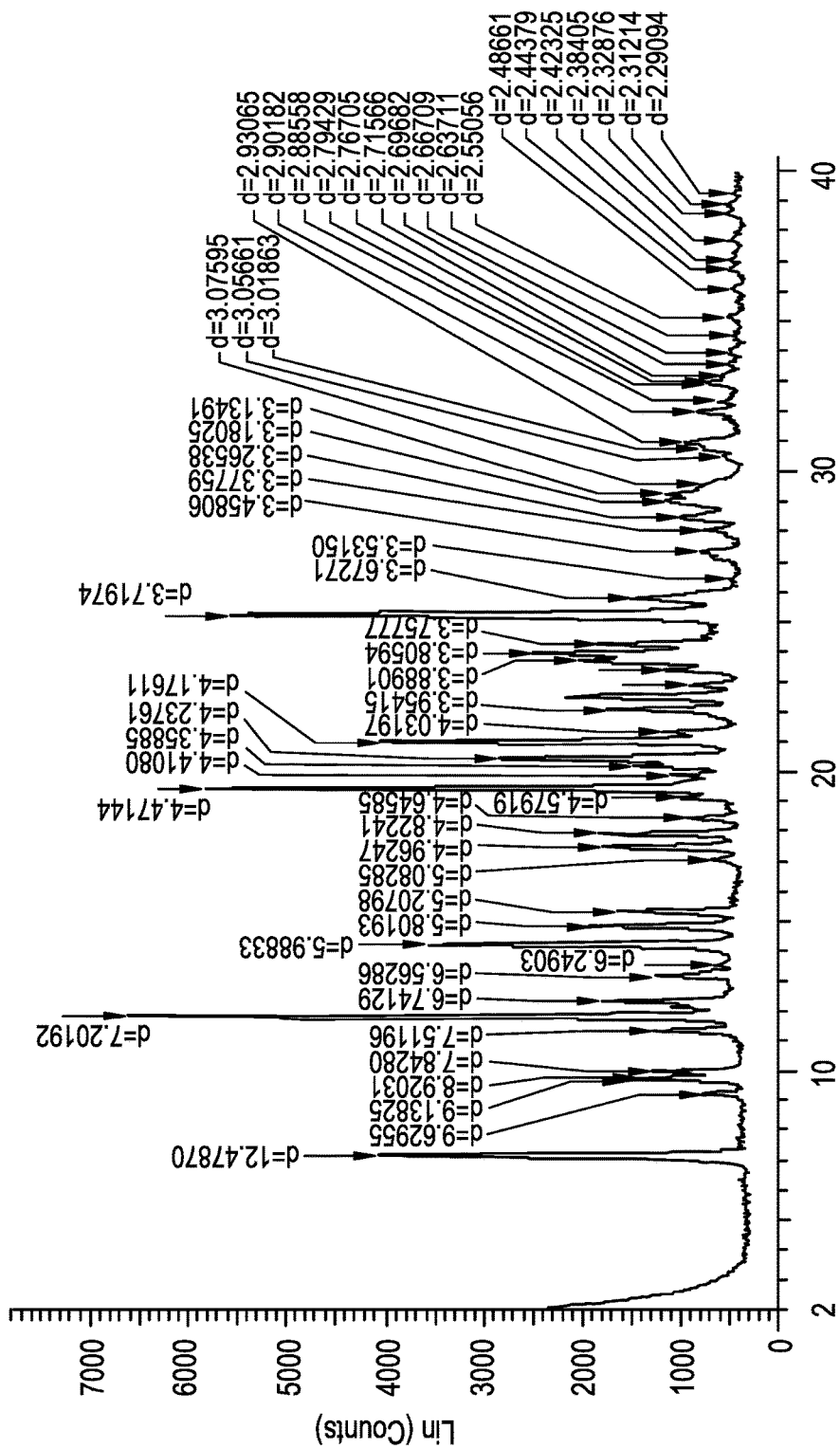
Figure 7: X-ray Powder Diffraction Pattern of Tosylate Salt Y Form B

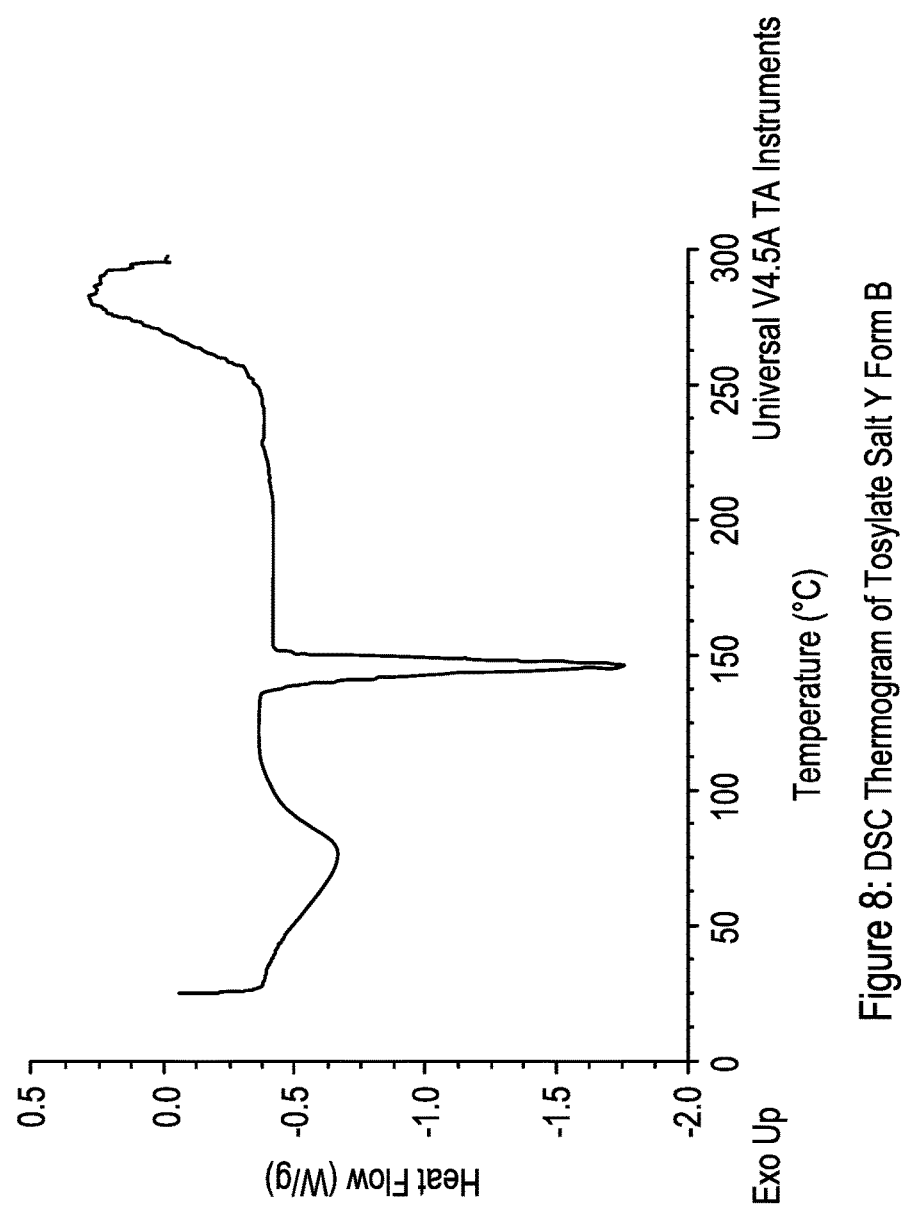
Figure 8: DSC Thermogram of Tosylate Salt Y Form B

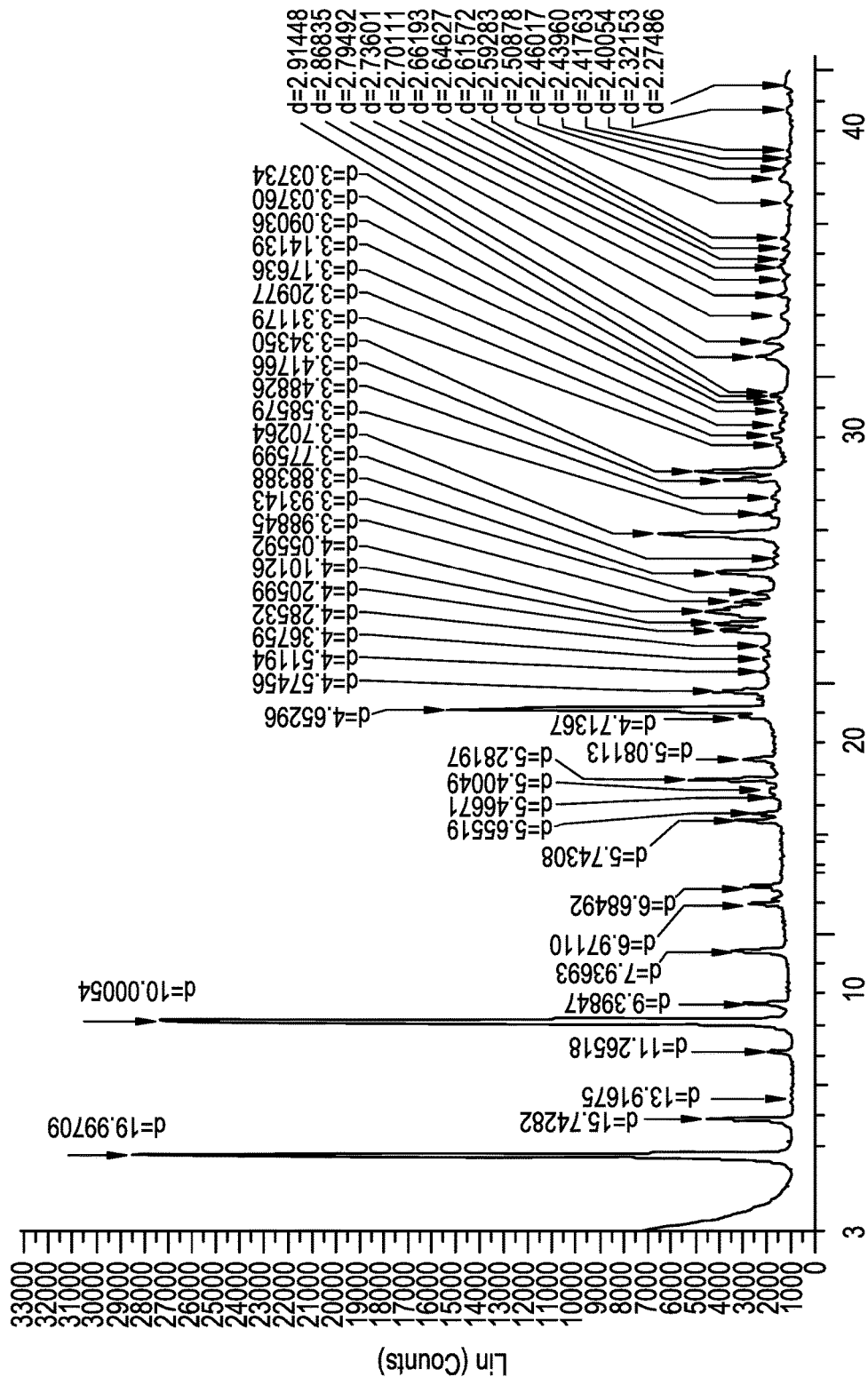
Figure 9: X-ray Powder Diffraction Pattern of Tosylate Salt Y Form D

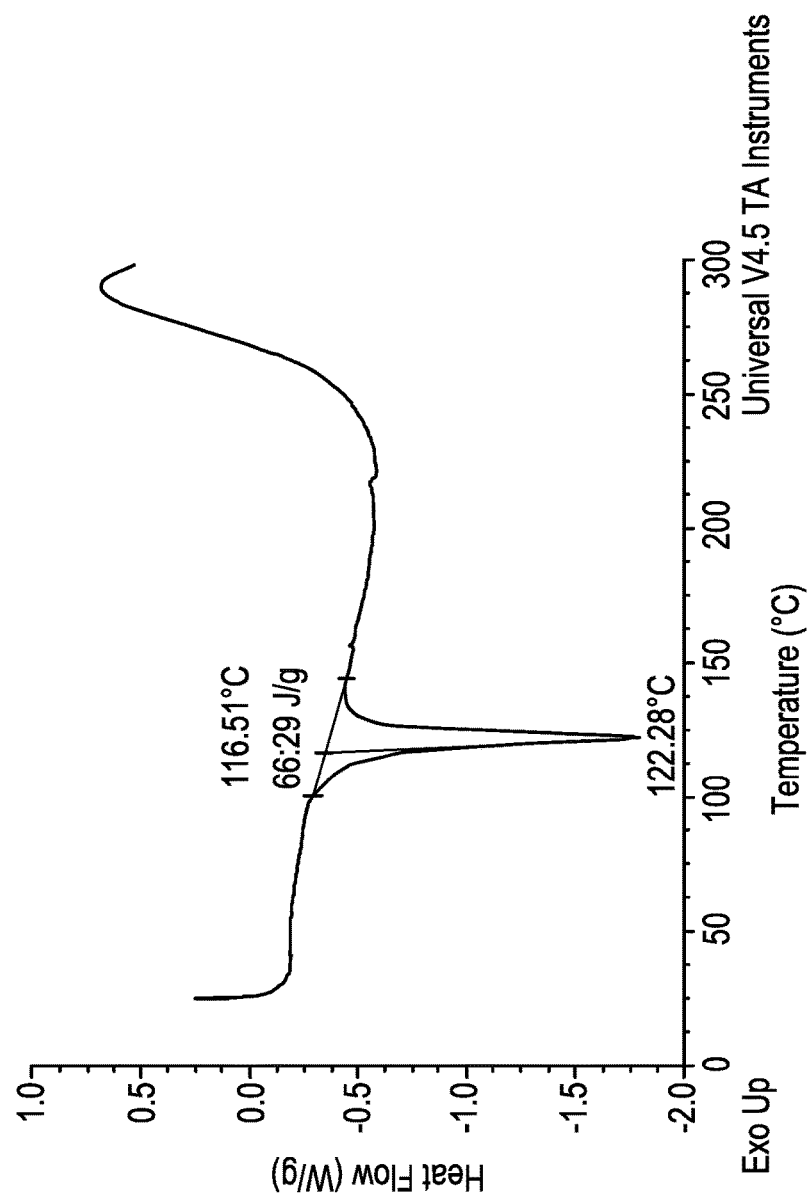
Figure 10: DSC Thermogram of Tosylate Salt Y Form D

C5-ANILINOQUINAZOLINE COMPOUNDS AND THEIR USE IN TREATING CANCER

CROSS-REFERENCE TO RELATED APPLICATION

This application claims the benefit under 35 U.S.C. § 119(e) of U.S. Provisional Patent Application No. 62/490,859, filed on Apr. 27, 2017, the entirety of which is hereby incorporated by reference.

FIELD OF INVENTION

The specification generally relates to $C_5$-anilinoquinazoline compounds and pharmaceutically acceptable salts thereof. These compounds and their pharmaceutically acceptable salts selectively modulate KIT, including wild-type KIT and primary and secondary KIT mutations, and the specification therefore also relates to the use of such compounds and salts thereof to treat or prevent KIT mediated disease, including cancer. The specification further relates to crystalline forms of $C_5$-anilinoquinazoline compounds and pharmaceutically acceptable salts thereof; pharmaceutical compositions comprising such compounds and salts; kits comprising such compounds and salts; methods of manufacture of such compounds and salts; and to methods of treating KIT mediated disease, including cancer, using such compounds and salts.

BACKGROUND

Receptor tyrosine kinases (RTK) can be oncogenic drivers in cancer due to genetic aberrations such as amplification, mutations or fusion events or via overexpression (M. A. Lemmon, K. M. Ferguson, *Cell* 130, 213 (2007)). Most aberrations in RTK result in ligand-independent activation of the receptor and activation of downstream signalling promoting cell growth and proliferation and increased survival. The class III RTK including KIT, platelet-derived growth factor receptor (PDGFR) alpha and beta, colony-stimulating factor 1 receptor (CSF1R), and the Fms-like tyrosine kinase 3 receptor (FLT3) is implicated in a variety of human cancers (K. Verstraete. S. N. Savvides, *Nat. Rev. Cancer* 12, 753 (2012)).

The gene encoding KIT is located on Chr 4 and comprises 21 exons (J. Lennartsson, L. Ronnstrand, *Physiol Rev.* 92, 1619 (2012)). The 976 amino acids of the KIT protein are divided into key domains: an extracellular domain, a transmembrane domain, a juxtamembrane domain (JM) and kinase domain separated by a kinase insert (KID) in the middle. The mature protein is ~145 KDa following N glycosylation and is expressed at the cell surface. Following stem cell factor (SCF) binding, the dimerisation increases the intrinsic kinase activity phosphorylating tyrosine residues in the JM domain (Y547, Y553, Y568 and Y570) followed by phosphorylations in the KID (Y703, Y721, Y729/730) and finally the activation loop (Y823) (J. P. DiNitto et al., *J. Biochem.* 147, 601 (2010)). Some phosphoylations sites on KIT are key docking sites for adaptors and downstream effectors propagating the activation signal. PI3K, Src and MAPK are key signalling pathways activated downstream of KIT. Regulation of KIT signalling includes internalization and subsequent degradation of the receptor, phosphorylation of Ser 741 and 746, and dephosphorylation of tyrosine residues by phosphatases such as SHP1.

KIT-driven signaling plays a key role in specific cell types, including interstitial cells of Cajal (ICCs), melanocytes, mast cells, germ cells and some hematopoietic stem cells (J. Lennartsson, L. Ronnstrand, *Physiol Rev.* 92, 1619 (2012)). Aberrations of KIT are observed in malignancies derived from these cell types. For example, KIT mutations are reported in gastrointestinal stromal tumours (originating from ICC), in mastocytosis and in melanomas.

Mutations in KIT in cancer affect multiple exons with hotspot mutations observed in the JM and kinase domains (J. Lennartsson, L. Ronnstrand, *Physiol Rev.* 92, 1619 (2012)). Mutations in the JM domain are thought to remove the autoinhibitory interaction of the JM domain with the kinase domain (J. P. DiNitto et al., *J. Biochem.* 147, 601 (2010)). Lower frequency mutations are present in exon 9 (extracellular Ig domain 5) and 13 (ATP binding pocket and gatekeeper). Mutations in the JM domain are observed in GIST while mutations affecting the kinase domain, in particular the A loop are frequently observed in mastocytosis. Similarly, PDGFR mutations in GIST affect both the JM domain and the kinase domain (C. Bahlawane et al., *Cell Commun. Signal.* 13, 21 (2015)).

Gastrointestinal stromal tumors (GISTs) are the most common mesenchymal tumors of the gastrointestinal tract (C. M. Barnett, C. L. Corless, M. C. Heinrich. *Hematol. Oncol. Clin. North Am.* 27, 871 (2013)). GISTs are most commonly found in the stomach and small intestine. Neoplastic GIST originate from the same precursor cells as the ICC and the vast majority of GIST express KIT protein initially called CD117. KIT mutations affecting exon 11 were first identified in GIST in 1998 (S. Hirota et al., *Science* 279, 577 (1998)). The same publication also reported the oncogenicity of KIT mutations expressed ectopically in Ba/F3 cells and their constitutive kinase activation. 75-80% GIST harbor KIT mutations and ~10% PDGFR mutations (J. A. Fletcher, *Cancer Res.* 76, 6140 (2016)). Rare aberrations in BRAF, NF1 and SDH account for what is referred to as WT KIT (C. M. Barnett, C. L. Corless, M. C. Heinrich, *Hematol. Oncol. Clin. North Am.* 27, 871 (2013)).

Imatinib was the first KIT inhibitor tested in GIST, demonstrating remarkable activity in patients with advanced GIST (G. D. Demetri et al., *N. Engl. J. Med.* 347, 472 (2002), J. Verweij et al., *Lancet* 364, 1127 (2004), C. D. Blanke et al., *J. Clin. Oncol.* 26, 626 (2008)). A meta-analysis of 2 large clinical studies concluded that patients with exon 9 mutations in KIT or other mutations had worse prognosis than patients with exon 11 mutations (Metagist, *J. Clin. Oncol.* 28, 1247 (2010)). In addition, a high dose imatinib (800 mg) did not improve progression-free survival in patients with exon 9 mutations compared to the standard dose (400 mg). Clinical resistance to imatinib was first reported in 2005 (C. R. Antonescu et al., *Clin. Cancer Res.* 11, 4182 (2005)) but a larger study following patients treated with imatinib as part of a PhII study B2222 showed a reactivation of KIT and KIT signalling with patients who have initially benefited from imatinib relapsed (M. C. Heinrich et al., *J. Clin. Oncol.* 24, 4764 (2006)). Secondary resistance mutations were noted at key residues: V654A in the ATP-binding pocket, T670I at the gatekeeper residue and A loop (D816X, D820X, N822K, Y823D). In addition, so called "primary resistance" to imatinib was mainly observed in patients with exon9 mutations. Overall, 50% of patients developed resistance within 2 years (C. D. Blanke et al., *J. Clin. Oncol.* 26, 626 (2008).).

Sunitinib is a multikinase inhibitor including KIT and PDGFR. Sunitinib demonstrated clinical activity in GIST patients following progression on imatinib (G. D. Demetri et al., *Lancet* 368, 1329 (2006)). Clinical benefit with sunitinib was observed in patients with primary exon 9 mutations. In addition, patients with secondary mutations affecting exon 13 and 14 had longer progression-free and overall survival compared to patients with secondary mutations affecting the A loop (M. C. Heinrich et al., *J. Clin. Oncol.* 26, 5352 (2008)). Clinical progression with sunitnib was observed within 1 year of treatment. Ectopic expression of KIT with primary and secondary mutations in CHO cells showed that sunitinib reduced KIT phosphorylation preferentially when KIT aberrations affected the ATP binding pocket or the gatekeeper.

Regorafenib, another multikinase inhibitor has shown clinical activity in patients with GIST after relapse to imatinib and sunitinib (G. D. Demetri et al., *Lancet* 381, 295 (2013)). The PhIII study reported a median PFS of 4.8 months.

Accordingly, there is a need for KIT inhibitors that inhibit secondary KIT mutations, and furthermore, are selective against KDR, particularly as existing treatments are ineffective against such secondary mutations. There is also a need for KIT inhibitors that inhibit primary KIT mutations and wildtype KIT.

SUMMARY

The compounds of the disclosure have been found to possess potent anti-tumour activity, being useful in inhibiting a range of secondary KIT mutations, including V654A, D816H and T670I, as well as primary mutations and wildtype KIT, and furthermore are selective against KDR. The compounds of the disclosure have the required pharmaceutical properties, for example, good PK properties.

Briefly, this specification describes, in part, a compound of Formula (I):

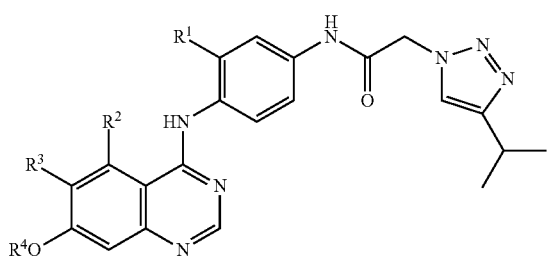

or a pharmaceutically acceptable salt thereof, wherein:—
$R^1$ is selected from hydrogen and fluoro;
$R^2$ is selected from fluoro and $C_{1-2}$ alkoxy;
$R^3$ is selected from hydrogen and methoxy; and
$R^4$ is a $C_{1-3}$ alkyl, optionally substituted with a group selected from $C_{1-3}$ alkoxy and $NR^5R^6$, where $R^5$ and $R^6$ are each independently hydrogen or methyl; or a 4 to 6 membered heterocyclyl ring containing one oxygen atom.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, a compound of Formula (I), or a pharmaceutically acceptable salt thereof, for the manufacture of a medicament for the treatment of cancer.

This specification also describes, in part, a method for treating cancer in a warm blooded animal in need of such treatment, which comprises administering to the warm-blooded animal a therapeutically effective amount of a compound of Formula (I), or a pharmaceutically acceptable salt thereof.

BRIEF DESCRIPTION OF THE FIGURES

FIG. 1 shows the XRPD for Form A of N-(4-{[5-Fluoro-7-(2-methoxyethoxy)quinazolin-4-yl]amino}phenyl)-2-[4-(propan-2-yl)-1H-1,2,3-triazol-1-yl]acetamide (Compound X, Example 12).

FIG. 2 shows the DSC for Form A of N-(4-{[5-Fluoro-7-(2-methoxyethoxy)quinazolin-4-yl]amino}phenyl)-2-[4-(propan-2-yl)-1H-1,2,3-triazol-1-yl]acetamide (Compound X, Example 12).

FIG. 3 shows the XRPD for Form B of N-(4-{[5-Fluoro-7-(2-methoxyethoxy)quinazolin-4-yl]amino}phenyl)-2-[4-(propan-2-yl)-1H-1,2,3-triazol-1-yl]acetamide (Compound X, Example 12).

FIG. 4 shows the DSC for Form B of N-(4-{[5-Fluoro-7-(2-methoxyethoxy)quinazolin-4-yl]amino}phenyl)-2-[4-(propan-2-yl)-1H-1,2,3-triazol-1-yl]acetamide (Compound X, Example 12).

FIG. 5 shows the XRPD for Form A of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt (Tosylate Salt Y, Example 12A).

FIG. 6 shows the DSC for Form A of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt (Tosylate Salt Y, Example 12A).

FIG. 7 shows the XRPD for Form B of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt (Toslate Salt Y, Example 12A).

FIG. 8 shows the DSC for Form B of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt (Tosylate Salt Y. Example 12A).

FIG. 9 shows the XRPD for Form D of N-(4-{[5-Fluoro-7-(2-methoxy ethoxy)quinazolin-4-yl]amino}phenyl)-2-[4-(propan-2-yl)-1H-1,2,3-triazol-1-yl]acetamide tosylate salt (Tosylate Salt Y, Example 12A).

FIG. 10 shows the DSC for Form D of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt (Toslate Salt Y, Example 12A).

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

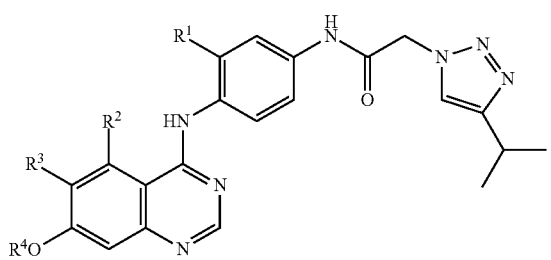

(I)

or a pharmaceutically acceptable salt thereof, wherein:—
$R^1$ is selected from hydrogen and fluoro;
$R^2$ is selected from fluoro and $C_{1-2}$ alkoxy;
$R^3$ is selected from hydrogen or methoxy; and
$R^4$ is a $C_{1-3}$ alkyl, optionally substituted with a group selected from $C_{1-3}$ alkoxy and $NR^5R^6$, where $R^5$ and $R^6$ are each independently hydrogen or methyl; or a 4 to 6 membered heterocyclyl ring containing one oxygen atom.

Suitable 4 to 6 membered heterocyclyl rings containing one oxygen atom include an oxetanyl ring, a tetrahydrofuranyl ring and an oxanyl ring.

The term "oxetanyl" ring includes oxetan-3-yl, the structure of which is shown below:

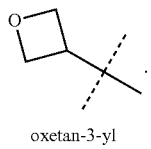

oxetan-3-yl

The term "tetrahydrofuranyl" includes tetrahydrofuran-3-yl, the structure of which is shown below:

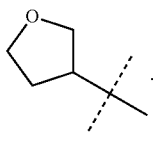

tetrahydrofuran-3-yl

The term "oxanyl" ring includes oxan-3-yl and oxan-4-yl groups, the structures of which are shown below:

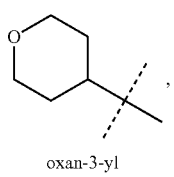 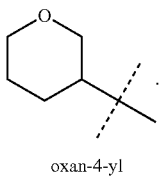

oxan-3-yl     oxan-4-yl

In the above structures the dashed line indicates the bonding position of the relevant group.

An oxanyl ring may also be referred to as a tetrahydropyranyl ring. Similarly, an oxan-4-yl ring may be referred to as a tetrahydropyran-4-yl ring, and an oxan-3-yl ring may be referred to as a tetrahydropyran-3-yl ring.

The prefix $C_{p-q}$ in $C_{p-q}$ alkyl and other terms (where p and q are integers) indicates the range of carbon atoms that are present in the group, for example $C_{1-3}$ alkyl includes $C_1$ alkyl (methyl), $C_2$ alkyl (ethyl) and $C_3$ alkyl (propyl as n-propyl and isopropyl).

The term $C_{p-q}$ alkoxy comprises —O—$C_{p-q}$ alkyl groups.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example one or two hydrogens, or alternatively one hydrogen) on the designated group is replaced by the indicated substituent(s) (for example one or two substituents, or alternatively one substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002. A suitable pharmaceutically acceptable salt of a compound of Formula (I) is, for example, an acid addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

In one embodiment, there is provided a compound of Formula (I) or a pharmaceutically acceptable salt thereof, where the pharmaceutically acceptable salt is a tosylate, mesylate or besylate salt. These salts showed improved handling properties for formulations comprising compounds of Formula (I). In one embodiment, there is provided a compound of Formula (I) or a pharmaceutically acceptable salt thereof, where the pharmaceutically acceptable salt is a tosylate salt. In one embodiment, there is provided a compound of Formula (I) or a pharmaceutically acceptable salt thereof, where the pharmaceutically acceptable salt is a mono-tosylate salt, i.e. the stoichiometry of the compound of the Formula (I) to tosylate is 1:1.

A further embodiment provides any of the embodiments defined herein (for example the embodiment of claim 1) with the proviso that one or more specific Examples (for instance, one, two or three specific Examples) selected from the group consisting of Examples 1, 2, 3, 4, 5, 6, 7, 8, 9, 10, 11, 12, 12A, 13, 14, 15, 16, 17, 18, 19, 20, 21 and 22 is individually disclaimed.

A further embodiment provides any of the embodiments defined herein (for example the embodiment of claim 1) with the proviso that one or more specific Examples (for instance, one, two or three specific Examples) selected from the group consisting of Examples 1, 2, 3, 4, 5, 6, 7, 8, 9, 10, 11, 12, 13, 14, 15, 16, 17, 18, 19, 20, 21 and 22 is individually disclaimed.

In one embodiment, $R^1$ is hydrogen. In one embodiment, $R^1$ is fluoro.

In one embodiment, $R^2$ is selected from fluoro, methoxy and ethoxy. In one embodiment, $R^2$ is fluoro. In one embodiment, $R^2$ is methoxy. In one embodiment, $R^2$ is ethoxy.

In one embodiment, $R^3$ is hydrogen. In one embodiment, $R^3$ is methoxy.

In one embodiment, $R^4$ is selected from $C_{1-3}$ alkyl optionally substituted with a group selected from methoxy and $NR^5R^6$ where $R^5$ and $R^6$ are each independently hydrogen or methyl; and an oxetanyl, a tetrahydrofuranyl and an oxanyl ring.

In one embodiment, $R^4$ is selected from $C_{1-3}$ alkyl optionally substituted with a group selected from methoxy and $NR^5R^6$ where $R^5$ and $R^6$ are each methyl; and an oxetanyl, a tetrahydrofuranyl and an oxanyl ring.

In one embodiment, $R^4$ is selected from methyl, ethyl, isopropyl, 2-(dimethylamino)ethyl, 2-methoxyethyl, oxetan-3-yl, tetrahydrofuran-3-yl and oxan-4-yl.

In one embodiment, $R^4$ is methyl. In one embodiment, $R^4$ is ethyl. In one embodiment, $R^4$ is isopropyl.

In one embodiment, $R^4$ is 2-dimethylaminoethyl. In one embodiment, $R^4$ is 2-methoxyethyl. In one embodiment, $R^4$ is oxetan-3-yl. In one embodiment, $R^4$ is tetrahydrofuran-3-yl. In one embodiment, $R^4$ is oxan-4-yl.

In one embodiment, $R^1$ is hydrogen, $R^2$ is methoxy, $R^3$ is hydrogen and $R^4$ is methyl.

In one embodiment, $R^1$ is hydrogen, $R^2$ is fluoro, $R^3$ is hydrogen and $R^4$ is 2-methoxyethyl.

In one embodiment there is provided a compound of Formula (I), or a pharmaceutically acceptable salt thereof, wherein the compound is selected from the group consisting of:

N-{4-[(5,7-dimethoxyquinazolin-4-yl)amino]-3-fluorophenyl}-2-[4-(propan-2-yl)-1H-1,2,3-triazol-1-yl]acetamide;
N-{4-[(5-fluoro-6,7-dimethoxyquinazolin-4-yl)amino]phenyl}-2-[4-(propan-2-yl)-1H-1,2,3-triazol-1-yl]acetamide;
(R)—N-(4-{[5-Ethoxy-7-(tetrahydrofuran-3-yloxy)quinazolin-4-yl]amino}phenyl)-2-[4-(propan-2-yl)-1H-1,2,3-triazol-1-yl]acetamide;
(S)—N-(4-{[5-Ethoxy-7-(tetrahydrofuran-3-yloxy)quinazolin-4-yl]amino}phenyl)-2-[4-(propan-2-yl)-1H-1,2,3-triazol-1-yl]acetamide;
N-(4-((5-Ethoxy-7-((tetrahydro-2H-pyran-4-yl)oxy)quinazolin-4-yl)amino)phenyl)-2-(4-isopropyl-1H-1,2,3-triazol-1-yl)acetamide;
N-(4-((7-(2-(Dimethylamino)ethoxy)-5-ethoxyquinazolin-4-yl)amino)phenyl)-2-(4-isopropyl-1H-1,2,3-triazol-1-yl)acetamide;
N-(4-((5-Ethoxy-7-methoxyquinazolin-4-yl)amino)phenyl)-2-(4-isopropyl-1H-1,2,3-triazol-1-yl)acetamide;
N-(4-((5-Ethoxy-7-(2-methoxyethoxy)quinazolin-4-yl)amino)phenyl)-2-(4-isopropyl-1H-1,2,3-triazol-1-yl)acetamide;
N-(4-((5-Ethoxy-7-(oxetan-3-yloxy)quinazolin-4-yl)amino)phenyl)-2-(4-isopropyl-1H-1,2,3-triazol-1-yl)acetamide;
N-(4-{[5-Methoxy-7-(tetrahydro-2H-pyran-4-yloxy)quinazolin-4-yl]amino}phenyl)-2-[4-(propan-2-yl)-1H-1,2,3-triazol-1-yl]acetamide;
2-[4-(Propan-2-yl)-1H-1,2,3-triazol-1-yl]-N-{4-[(5,6,7-trimethoxyquinazolin-4-yl)amino]phenyl}acetamide;
N-(4-{[5-Fluoro-7-(2-methoxyethoxy)quinazolin-4-yl]amino}phenyl)-2-[4-(propan-2-yl)-1H-1,2,3-triazol-1-yl]acetamide;
(R)-2-(4-Isopropyl-1H-1,2,3-triazol-1-yl)-N-(4-((5-methoxy-7-((tetrahydrofuran-3-yl)oxy)quinazolin-4-yl)amino)phenyl)acetamide;
(S)-2-(4-Isopropyl-1H-1,2,3-triazol-1-yl)-N-(4-((5-methoxy-7-((tetrahydrofuran-3-yl)oxy)quinazolin-4-yl)amino)phenyl)acetamide;
N-(4-{[5-Methoxy-7-(propan-2-yloxy)quinazolin-4-yl]amino}phenyl)-2-[4-(propan-2-yl)-1H-1,2,3-triazol-1-yl]acetamide;
N-(4-{[5-Methoxy-7-(oxetan-3-yloxy)quinazolin-4-yl]amino}phenyl)-2-[4-(propan-2-yl)-1H-1,2,3-triazol-1-yl]acetamide;
N-[4-({7-[2-(Dimethylamino)ethoxy]-5-methoxyquinazolin-4-yl}amino)phenyl]-2-[4-(propan-2-yl)-1H-1,2,3-triazol-1-yl]acetamide;
N-{4-[(7-Ethoxy-5-methoxyquinazolin-4-yl)amino]phenyl}-2-[4-(propan-2-yl)-1H-1,2,3-triazol-1-yl]acetamide;
N-{4-[(5,7-Diethoxyquinazolin-4-yl)amino]phenyl}-2-[4-(propan-2-yl)-1H-1,2,3-triazol-1-yl]acetamide;
N-(4-{[5-Methoxy-7-(2-methoxyethoxy)quinazolin-4-yl]amino}phenyl)-2-[4-(propan-2-yl)-1H-1,2,3-triazol-1-yl]acetamide;
N-{4-[(5-Fluoro-7-methoxyquinazolin-4-yl)amino]phenyl}-2-[4-(propan-2-yl)-1H-1,2,3-triazol-1-yl]acetamide; and
N-{4-[(5,7-Dimethoxyquinazolin-4-yl)amino]phenyl}-2-[4-(propan-2-yl)-1H-1,2,3-triazol-1-yl]acetamide.

In one embodiment there is provided a compound of Formula (I), or a pharmaceutically acceptable salt thereof, wherein the compound is selected from the group consisting of:

N-(4-{[5-Fluoro-7-(2-methoxyethoxy)quinazolin-4-yl]amino}phenyl)-2-[4-(propan-2-yl)-1H-1,2,3-triazol-1-yl]acetamide; and
N-{4-[(5,7-Dimethoxyquinazolin-4-yl)amino]phenyl}-2-[4-(propan-2-yl)-1H-1,2,3-triazol-1-yl]acetamide.

In one embodiment there is provided a compound of Formula (I), or a pharmaceutically acceptable salt thereof, wherein the compound is N-(4-{[5-Fluoro-7-(2-methoxyethoxy)quinazolin-4-yl]amino}phenyl)-2-[4-(propan-2-yl)-1H-1,2,3-triazol-1-yl]acetamide.

In one embodiment there is provided a compound of Formula (I) wherein the compound is N-(4-{[5-Fluoro-7-(2-methoxyethoxy)quinazolin-4-yl]amino}phenyl)-2-[4-(propan-2-yl)-1H-1,2,3-triazol-1-yl]acetamide, in the free base form (also referred to as Compound X).

In one embodiment there is provided a compound of Formula (I) wherein the compound is N-(4-{[5-Fluoro-7-(2-methoxy ethoxy)quinazolin-4-yl]amino}phenyl)-2-[4-(propan-2-yl)-1H-1,2,3-triazol-1-yl]acetamide tosylate salt (also referred to as Tosylate Salt Y).

In one embodiment there is provided a compound of Formula (I), or a pharmaceutically acceptable salt thereof, wherein the compound is N-{4-[(5,7-Dimethoxyquinazolin-4-yl)amino]phenyl}-2-[4-(propan-2-yl)-1H-1,2,3-triazol-1-yl]acetamide.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The invention encompasses all such solvated and unsolvated forms of compounds of Formula (I), particularly to the extent that such forms possess KIT inhibitory activity, as for example measured using the tests described herein.

Atoms of the compounds and salts described in this specification may exist as their isotopes. The invention encompasses all compounds of Formula (I) where an atom is replaced by one or more of its isotopes (for example a compound of Formula (I) where one or more carbon atom is an $^{11}$C or $^{13}$C carbon isotope, or where one or more hydrogen atoms is a $^{2}$H or $^{3}$H isotope, or where one or more nitrogen atoms is a $^{15}$N isotope or where one of more oxygen atoms is an $^{17}$O or $^{18}$O isotope).

Compounds and salts described in this specification may exist in optically active or racemic forms by virtue of one or more asymmetric carbon atoms. The invention includes any optically active or racemic form of a compound of Formula (I) which possesses KIT inhibitory activity, as for example measured using the tests described herein. The synthesis of optically active forms may be carried out by standard techniques of organic chemistry well known in the art, for example by synthesis using optically active materials or by resolution of a racemic form.

Therefore, in one embodiment there is provided a compound of Formula (I), or a pharmaceutically acceptable salt thereof, which is a single optical isomer being in an enantiomeric excess (% e.e.) of ≥95%, ≥98% or ≥99%. In one embodiment, the single optical isomer is present in an enantiomeric excess (% e.e.) of ≥99%.

Some of the compounds of Formula (I) may be crystalline and may have more than one crystalline form. It is to be understood that the invention encompasses any crystalline or amorphous form, or mixtures thereof, which possess properties useful in KIT inhibitory activity. It is well known how to determine the efficacy of a crystalline or amorphous form by the standard tests described hereinafter.

It is generally known that crystalline materials may be analysed using conventional techniques such as, for example, X-ray powder diffraction (hereinafter XRPD) analysis and Differential Scanning Calorimetry (hereinafter DSC).

As an example, the compound of Example 12. Compound X, exhibits crystallinity and two crystalline forms, Form A and Form B, have been identified and have been obtained using the conditions described hereinafter in the experimental section.

Polymorphic Form A of Compound X

Accordingly, a further aspect of the invention is Form A of Compound X (Example 12).

According to the invention there is provided a crystalline form, Form A, of Compound X which has an XRPD pattern with at least one specific peak at about 2-theta=6.7°, measured using CuKα radiation.

According to the invention there is provided a crystalline form, Form A, of Compound X which has an XRPD pattern with at least one specific peak at about 2-theta=18.7°, measured using CuKα radiation.

According to the invention there is provided a crystalline form, Form A. of Compound X which has an XRPD pattern with at least two specific peaks at about 2-theta=6.7° and 18.7°, measured by CuKα radiation.

According to the invention there is provided a crystalline form, Form A, of Compound X which has an XRPD pattern with specific peaks at about 2-theta=3.4, 6.7, 9.9, 16.2, 18.7, 22.1, 23.3 25.1, 26.6, 28.9°, measured using CuKα radiation.

According to the invention there is provided crystalline form, Form A. of Compound X which has an XRPD pattern substantially the same as the XRPD pattern shown in FIG. 1, measured using CuKα radiation.

According to the invention there is provided a crystalline form, Form A, of Compound X which has an XRPD pattern with at least one specific peak at 2-theta=6.7° plus or minus 0.2° 2-theta, measured using CuKα radiation.

According to the invention there is provided a crystalline form, Form A, of Compound X which has an XRPD pattern with at least one specific peak at 2-theta=18.7° plus or minus 0.2° 2-theta, measured using CuKα radiation.

According to the invention there is provided a crystalline form, Form A, of Compound X which has an XRPD pattern with at least two specific peaks at 2-theta=6.7° and 18.7° wherein said values may be plus or minus 0.2° 2-theta, measured using CuKα radiation.

According to the invention there is provided a crystalline form, Form A, of Compound X which has an XRPD pattern with specific peaks at 2-theta=3.4, 6.7, 9.9, 16.2, 18.7, 22.1, 23.3 25.1, 26.6, 28.9° wherein said values may be plus or minus 0.2° 2-theta, measured using CuKα radiation.

DSC analysis of Compound X. Form A shows a melting endotherm with an onset of 235.7° C. and a peak at 237.6° C. (FIG. 2).

Thus DSC analysis shows Compound X, Form A is a high melting solid with an onset of melting at about 235.7° C. and a peak at about 237.6° C.

Polymorphic Form B of Compound X

A further aspect of the invention is Form B of Compound X.

According to the invention there is provided a crystalline form, Form B, of Compound X which has an XRPD pattern with at least one specific peak at about 2-theta=4.2°, measured using CuKα radiation.

According to the invention there is provided a crystalline form, Form B, of Compound X which has an XRPD pattern with at least one specific peak at about 2-theta=7.7°, measured using CuKα radiation.

According to the invention there is provided a crystalline form, Form B, of Compound X which has an XRPD pattern with at least two specific peaks at about 2-theta=4.2° and 7.7°, measured using CuKα radiation.

According to the invention there is provided a crystalline form, Form B, of Compound X which has an XRPD pattern with specific peaks at about 2-theta=4.2, 6.6, 7.7, 9.8, 13.1, 13.7, 18.6, 20.0, 26.5, 28.8°, measured using CuKα.

According to the invention there is provided a crystalline form, Form B, of Compound X which has an XRPD pattern substantially the same as the XRPD shown in FIG. 3, measured using CuKα radiation.

According to the invention there is provided a crystalline form, Form B, of Compound X which has an XRPD pattern with at least one specific peak at 2-theta=4.2° plus or minus 0.2° 2-theta, measured using CuKα radiation.

According to the invention there is provided a crystalline form, Form B, of Compound X which has an XRPD pattern with at least one specific peak at 2-theta=7.7° plus or minus 0.2° 2-theta, measured using CuKα radiation.

According to the invention there is provided a crystalline form, Form B, of Compound X which has an XRPD pattern with at least two specific peaks at 2-theta=4.2° and 7.7° wherein said values may be plus or minus 0.2° 2-theta, measured using CuKα radiation.

According to the invention there is provided a crystalline form, Form B, of Compound X which has an XRPD pattern with specific peaks at 2-theta=4.2, 6.6, 7.7, 9.8, 13.1, 13.7, 18.6, 20.0, 26.5, 28.8° wherein said values may be plus or minus 0.2° 2-theta, measured using CuKα radiation.

DSC analysis of Compound X, Form B is shown in FIG. 4.

As a further example, the compound of Example 12A, Tosylate Salt Y, exhibits crystallinity and four crystalline forms, Form A, Form B, Form C and Form D have been identified and have been obtained using the conditions described hereinafter in the experimental section.

Polymorphic Form a of Tosylate Salt Y

Accordingly, a further aspect of the invention is Form A of Tosylate Salt Y (Example 12A).

According to the invention there is provided a crystalline form, Form A of Tosylate Salt Y, which has an XRPD pattern with at least one specific peak at about 2-theta=13.4°, measured using CuKα radiation.

According to the invention there is provided a crystalline form, Form A of Tosylate Salt Y, which has an XRPD pattern with at least one specific peak at about 2-theta=14.3°, measured using CuKα radiation.

According to the invention there is provided a crystalline form, Form A of Tosylate Salt Y, which has an XRPD pattern with at least two specific peaks at about 2-theta=13.4° and 14.3°, measured using CuKα radiation.

According to the invention there is provided a crystalline form, Form A of Tosylate Salt Y, which has an XRPD pattern with specific peaks at about 2-theta=11.7, 12.2, 13.4, 14.3, 17.3, 20.2, 21.4, 23.6, 23.7, 24.4°, measured using CuKα radiation.

According to the invention there is provided crystalline form, Form A of Tosylate Salt Y, which has an XRPD pattern substantially the same as the XRPD pattern shown in FIG. 5.

According to the invention there is provided crystalline form, Form A of Tosylate Salt Y, which has an XRPD pattern with at least one specific peak at 2-theta=13.4° plus or minus 0.2° 2-theta, measured using CuKα radiation.

According to the invention there is provided a crystalline form, Form A of Tosylate Salt Y, which has an XRPD pattern with at least one specific peak at 2-theta=14.3° plus or minus 0.2° 2-theta, measured using CuKα radiation.

According to the invention there is provided a crystalline form, Form A of Tosylate Salt Y, which has an XRPD pattern with at least two specific peaks at 2-theta=13.4° and 14.3° wherein said values may be plus or minus 0.2° 2-theta, measured using CuKα radiation.

According to the invention there is provided a crystalline form, Form A of Tosylate Salt Y, which has an XRPD pattern with specific peaks at 2-theta=11.7, 12.2, 13.4, 14.3, 17.3, 20.2, 21.4, 23.6, 23.7, 24.4° wherein said values may be plus or minus 0.2° 2-theta, measured using CuKα radiation.

DSC analysis of Form A of Tosylate Salt Y shows a melting endotherm with an onset of about 165.7° C. and a peak at about 170.8° C. (FIG. 6).

Thus DSC analysis shows Form A of Tosylate Salt Y is a high melting solid with an onset of melting at about 165.7° C. and a peak at about 170.8° C.

Polymorphic Form B of Tosylate Salt Y

A further aspect of the invention is Form B of Tosylate Salt Y.

According to the invention there is provided a crystalline form, Form B of Tosylate Salt Y, which has an XRPD pattern with at least one specific peak at about 2-theta=7.1°, measured using CuKα radiation.

According to the invention there is provided a crystalline form, Form B of Tosylate Salt Y, which has an XRPD pattern with at least one specific peak at about 2-theta=9.2°, measured using CuKα radiation.

According to the invention there is provided a crystalline form, Form B of Tosylate Salt Y, which has an XRPD pattern with at least two specific peaks at about 2-theta=7.1° and 9.2°, measured using CuKα radiation.

According to the invention there is provided a crystalline form, Form B of Tosylate Salt Y, which has an XRPD pattern with specific peaks at about 2-theta=7.1, 9.2, 11.8, 14.2, 19.4, 20.4, 20.9, 22.5, 23.9, 25.2°, measured using CuKα radiation.

According to the invention there is provided crystalline form, Form B of Tosylate Salt Y, which has an XRPD pattern substantially the same as the XRPD pattern shown in FIG. 7.

According to the invention there is provided crystalline form, Form B of Tosylate Salt Y, which has an XRPD pattern with at least one specific peak at 2-theta=7.1° plus or minus 0.2° 2-theta, measured using CuKα radiation.

According to the invention there is provided a crystalline form, Form B of Tosylate Salt Y, which has an XRPD pattern with at least one specific peak at 2-theta=9.2° plus or minus 0.2° 2-theta, measured using CuKα radiation.

According to the invention there is provided a crystalline form, Form B of Tosylate Salt Y, which has an XRPD pattern with at least two specific peaks at 2-theta=7.1° and 9.2° wherein said values may be plus or minus 0.2° 2-theta.

According to the invention there is provided a crystalline form, Form B of Tosylate Salt Y, which has an XRPD pattern with specific peaks at 2-theta=7.1, 9.2, 11.8, 14.2, 19.4, 20.4, 20.9, 22.5, 23.9, 25.2° wherein said values may be plus or minus 0.2° 2-theta, measured using CuKα radiation.

DSC analysis of Form B of Tosylate Salt Y shows a melting endotherm with an onset of about 140.0° C. and a peak at about 146.2° C. (FIG. 8).

Thus DSC analysis shows Form B of Tosylate Salt Y is a solid with an onset of melting at about 140.0° C. and a peak at about 146.2° C.

Polymorphic Form D of Tosylate Salt Y

A further aspect of the invention is Form D of Tosylate Salt Y.

According to the invention there is provided a crystalline form, Form D of Tosylate Salt Y, which has an XRPD pattern with at least one specific peak at about 2-theta=0.4°, measured using CuKα radiation.

According to the invention there is provided a crystalline form, Form D of Tosylate Salt Y, which has an XRPD pattern with at least one specific peak at about 2-theta=5.6°, measured using CuKα radiation.

According to the invention there is provided a crystalline form, Form D of Tosylate Salt Y, which has an XRPD pattern with at least two specific peaks at about 2-theta=4.4° and 5.6°, measured using CuKα radiation.

According to the invention there is provided a crystalline form, Form D of Tosylate Salt Y, which has an XRPD pattern with specific peaks at about 2-theta=4.4, 5.6, 8.8, 16.8, 19.1, 19.7, 21.9, 22.3, 24.8, 26.9°, measured using CuKα radiation.

According to the invention there is provided crystalline form, Form D of Tosylate Salt Y, which has an XRPD pattern substantially the same as the XRPD pattern shown in FIG. 9.

According to the invention there is provided crystalline form, Form D of Tosylate Salt Y, which has an XRPD pattern with at least one specific peak at 2-theta=4.4° plus or minus 0.2° 2-theta, measured using CuKα radiation.

According to the invention there is provided a crystalline form, Form D of Tosylate Salt Y, which has an XRPD pattern with at least one specific peak at 2-theta=5.6° plus or minus 0.2° 2-theta, measured using CuKα radiation.

According to the invention there is provided a crystalline form, Form D of Tosylate Salt Y, which has an XRPD pattern with at least two specific peaks at 2-theta=4.4° and 5.6° wherein said values may be plus or minus 0.2° 2-theta, measured using CuKα radiation.

According to the invention there is provided a crystalline form, Form D of Tosylate Salt Y, which has an XRPD pattern with specific peaks at 2-theta=4.4, 5.6, 8.8, 16.8, 19.1, 19.7, 21.9, 22.3, 24.8, 26.9° wherein said values may be plus or minus 0.2° 2-theta, measured using CuKα radiation.

DSC analysis of Form D of Tosylate Salt Y shows a melting endotherm with an onset of about 116.5° C. and a peak at about 122.3° C. (FIG. 10).

Thus DSC analysis shows Form D of Tosylate Salt Y s a solid with an onset of melting at about 116.5° C. and a peak at about 122.3° C.

When it is stated that the present invention relates to a crystalline form of Form A or Form B of Compound X, or Form A, Form B or Form D of Tosylate Salt Y, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that Compound X, Form A and Form B, and Tosylate Salt Y, Form A, Form B and Form D, of the invention are not limited to the crystals that provide X-ray powder diffraction patterns identical to the X-ray powder diffraction pattern shown in FIGS. 1, 3, 5, 7, and 9, and any crystals providing X-ray powder diffraction pattern shown in FIGS. 1, 3, 5, 7, and 9 fall within the scope of the present invention. A person skilled in the art of X-ray powder diffraction is able to judge the substantial identity of X-ray powder diffraction patterns.

Persons skilled in the art of X-ray powder diffraction will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn. C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in FIGS. 1, 3, 5, 7, and 9 and when reading Tables A to E (see Examples 12 and 12A). Furthermore, it should be understood that intensities might fluctuate depending on experimental conditions and sample preparation (preferred orientation).

The compounds of Formula (I) include one or more chiral centres. To the extent a structure or chemical name in this specification does not indicate chirality, the structure or name is intended to encompass any single stereoisomer (i.e. any single chiral isomer) corresponding to that structure or name, as well as any mixture of stereoisomers (e.g. a racemate). It is well-known in the art how such optically-active forms can be prepared. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

Compounds of Formula (I), where $R^2$ is fluoro, may for example be prepared by the reaction of a compound of Formula (II) or a salt thereof:

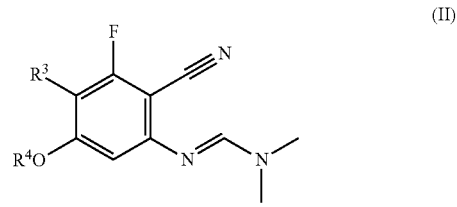

(II)

where $R^3$ and $R^4$ are as defined in any of the embodiments herein, with a compound of Formula (III):

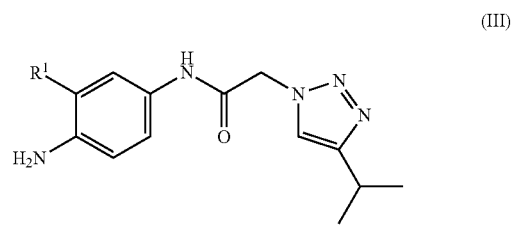

(III)

or a salt thereof, where $R^1$ is as defined in any of the embodiments herein. The reaction is conveniently performed in a suitable solvent (for example acetic acid) at a suitable temperature (for example a temperature of about 25 to 100° C.).

Compounds of Formula (II) and (III), and salts thereof, are therefore useful as intermediates in the preparation of compounds of Formula (I), where $R^2$ is fluoro, and provide a further embodiment.

In any of the embodiments where a compound of Formula (II) or (III) or a salt thereof is mentioned it is to be understood that such salts do not need to be pharmaceutically acceptable salts.

The compound of Formula (II) may for example be prepared by the reaction of a compound of Formula (IV):

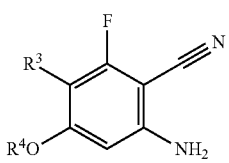

(IV)

or a salt thereof, where $R^3$ and $R^4$ are as defined in any of the embodiments herein, with a dialkyl acetal of DMF (for example 1,1-dimethoxy-N,N-dimethylmethanamine).

The compound of Formula (IV) may for example be prepared by the reaction of a compound of Formula (V):

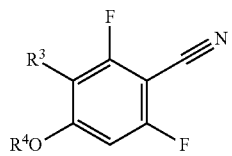

(V)

where $R^3$ and $R^4$ are as defined in any of the embodiments herein, with a weak base (for example aqueous ammonia) under high temperature and pressure conditions (for example a temperature of about 80 to 100° C. and a pressure of about 3 to 15 bar).

The compound of Formula (V) may for example be prepared by the reaction of a compound of Formula (VI):

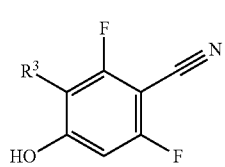

(VI)

or a salt thereof, where $R^3$ is as defined in any of the embodiments herein, with $R^4$—Br, where $R^4$ is as defined in any of the embodiments herein, in the presence of a suitable base (for example potassium carbonate) and solvent (for example dimethylformamide) and at a suitable temperature (for example about 80° C.).

The compound of Formula (III) may for example be prepared by the reaction of a compound of Formula (VII):

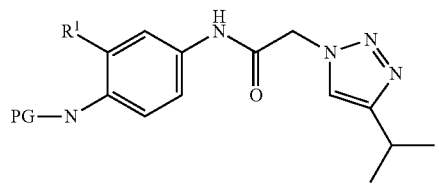

(VII)

where $R^1$ is as defined in any of the embodiments herein and PG is a suitable protecting group (for example tert-butyloxycarbonyl (BOC)), with a suitable deprotecting agent (for example HCl in dioxane) and in a suitable solvent (for example DCM).

The compound of Formula (VII) may for example be prepared by the reaction of a compound of Formula (VIII):

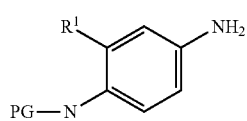

(VIII)

or a salt thereof, with a compound of Formula (IX):

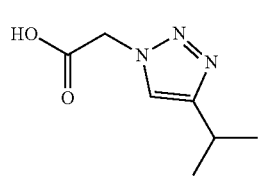

(IX)

or a salt thereof, where $R^1$ is as defined in any of the embodiments herein and PG is a suitable protecting group (for example tert-butyloxycarbonyl (BOC)), in the presence of a suitable reagent and base for peptide coupling (for example HATU and DIPEA respectively) and a suitable solvent (for example DMF).

Compounds of Formula (I), where $R^2$ is $C_{1-2}$ alkoxy, may for example be prepared by the reaction of a compound of Formula (X):

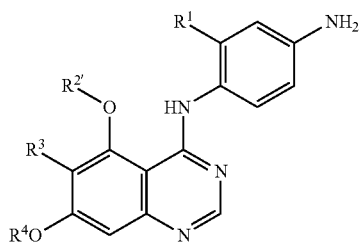

(X)

or a salt thereof, where $R^{2'}$ is $C_{1-2}$ alkyl and $R^1$, $R^3$ and $R^4$ are as defined in any of the embodiments herein, with a compound of Formula (XI):

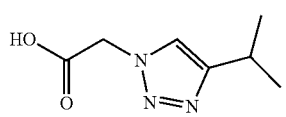

(XI)

or a salt thereof, in the presence of a suitable reagent and base for peptide coupling (for example HATU and DIPEA respectively) and a suitable solvent (for example DMF) and at a suitable temperature (for example room temperature). In one embodiment, $R^{2'}$ is methyl. In one embodiment, $R^{2'}$ is ethyl.

Compounds of Formula (X) and (XI), and salts thereof, are therefore useful as intermediates in the preparation of compounds of Formula (I), where $R^2$ is $C_{1-2}$ alkoxy, and provide a further embodiment.

In any of the embodiments where a compound of Formula (X) or (XI) or a salt thereof is mentioned it is to be understood that such salts do not need to be pharmaceutically acceptable salts.

The compound of Formula (X) may for example be prepared by the reaction of a compound of Formula (XII):

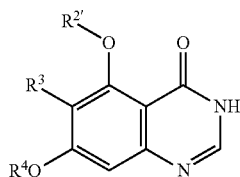

(XII)

or a salt thereof, where $R^{2'}$, $R^3$ and $R^4$ are as defined in any of the embodiments herein, with a compound of Formula (XIII):

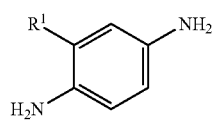

(XIII)

or a salt thereof, where $R^1$ is as defined in any of the embodiments herein, in the presence of a suitable peptide coupling reagent (for example PyBOP), a strong organic base (for example DBU) and a suitable solvent (for example MeCN).

The compound of Formula (XII) may for example be prepared by the reaction of a compound of Formula (XIV):

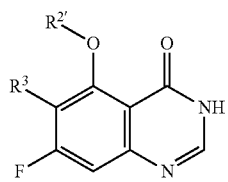

(XIV)

where $R^{2'}$ and $R^3$ are as defined in any of the embodiments herein, with $KOR^4$, or another suitable alkali metal alkoxide, at a suitable temperature (for example about 60 to 100° C.), where $R^4$ is as defined in any of the embodiments herein.

The compound of Formula (XIV) may for example be prepared by the reaction of a compound of Formula (XV):

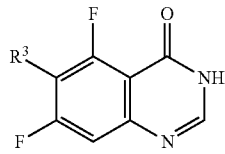

(XV)

where $R^3$ is as defined in any of the embodiments herein, with a suitable alkali metal alkoxide (for example $NaOR^{2'}$) at a suitable temperature (for example room temperature), where $R^{2'}$ is as defined in any of the embodiments herein.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of Formula (I) may be converted into further compounds of Formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

Compounds of Formula (I), (II) and (III), and any intermediates used to make these, can be prepared by methods similar to those shown in the Examples section.

Biological Assays

The following assay was used to measure the effects of the compounds of the invention.

3 different KIT cDNA encoding for the exon11 deletion (557-558) and a secondary mutation (V654A, T670I, D816H) from Genescript were cloned into pLVX-IRES Puro vector (Clontech). Lentiviral particles were generated using Trans-lentiviral ORF packaging kit (TLP 5918) from Thermo Scientific (Waltham, Mass.) in HEK293-T/17 cells, according to the manufacturer's instructions.

Tel-KDR myc was cloned into pBCS2004, a retroviral vector, wherein KDR (K790-V1356) is fused to the C-terminus of Tel. Retroviral particles were generated in HEK293T cells. The Tel-KDR plasmid was co-transfected with helper viruses (gag-Pol and VSV-G) into HEK293T cells using calcium phosphate and the virus was harvested 72 h after transfection.

Exponentially grown Ba/F3 cells (1.5×106 cells in 2 ml medium) were infected with 2 ml of viral suspension in a 6-well plate in the presence of mIL-3 (10 ng/ml) and polybrene (4 μg/ml) (Sigma Aldrich, St. Louis, Mo.) and incubated for 24 h. After 24 h, the cells were centrifuged and the viral supernatant was discarded. The cells were then re-suspended in fresh medium and allowed to recover for another day. The following day, the cells were seeded in complete medium without murine IL-3. After a week or two, when cells started proliferating, a selection was carried out by gradually increasing the puromycin concentration to 0.5 ug/ml. Once the cells were growing exponentially in puromycin, batches of cells were frozen down for banking.

The impact of KIT inhibitors on the viability of Ba/F3 expressing KIT mutations was determined using an MTS assay, which is a colorimetric sensitive quantification of viable cells in proliferation and cytotoxicity assay. In the MTS assay 3-(4,5-dimethylthiazol-2-yl)-2,5-diphenyltetrazolium bromide (MTT) in the presence of phenazine methosulfate (PMS) was used. The mitochondrial reductase forms a formazan which absorbs at 490 nm. Cells in exponential growth phase were added to 384-well plates containing pre-dispensed compounds (top concentration 10 uM, 10-point curve). The cells were incubated for 72 h at 37° C. and 5% $CO_2$. After 72 h, MTS reagent was added to the plates and incubated an additional 2 h at 37° C. before measuring the absorbance at 490 nm on a Tecan microplate reader using Magellan Software (Tecan Trading AG, Switzerland).

The absorbances were normalized as follows: (ReadDay0 control)/(Day3 control−Day0 control)*100. The $GI_{50}$ values were generated using Genedata Screener software (Genedata Lexington, Mass.). A non-linear regression with constraints for top and bottom between 100 and −100 and no constraint on the Hill coefficient was used to generate $GI_{50}$ values. The $GI_{50}$ values reported below are the calculated mean result of at least 3 biological replicates across all the cell lines tested.

The following data was generated for the Examples (the data below may be a result from a single experiment or an average of multiple repeat experiments):

| Example | Ba/F3-Parental GI50 (μM) | Ba/F3-T670I GI50 (μM) | Ba/F3-V654A GI50 (μM) | Ba/F3-D816H GI50 (μM) | TEL-KDR GI50 (μM) |
|---|---|---|---|---|---|
| 1 | 10.000 | 0.162 | 0.007 | 0.141 | 10.000 |
| 2 | 10.000 | 0.049 | 0.004 | 0.022 | 2.496 |
| 3 | 1.466 | 0.061 | 0.011 | 0.042 | 1.838 |
| 4 | 1.724 | 0.049 | 0.012 | 0.045 | 2.218 |
| 5 | 1.871 | 0.591 | 0.041 | 0.138 | 6.179 |
| 6 | 2.053 | 0.091 | 0.013 | 0.063 | 2.655 |
| 7 | 10.000 | 0.073 | 0.007 | 0.079 | 3.193 |
| 8 | 2.551 | 0.032 | 0.015 | 0.044 | 2.149 |
| 9 | 1.707 | 0.127 | 0.012 | 0.105 | 2.334 |
| 10 | 10.000 | 0.640 | 0.007 | 0.065 | 9.485 |
| 11 | 10.000 | 0.036 | 0.004 | 0.027 | 2.476 |
| 12 | 10.000 | 0.015 | 0.002 | 0.007 | 1.303 |
| 13 | 10.000 | 0.208 | 0.009 | 0.024 | 3.261 |
| 14 | 10.000 | 0.159 | 0.015 | 0.038 | 5.404 |
| 15 | 10.000 | 0.254 | 0.011 | 0.035 | 4.181 |
| 16 | 10.000 | 0.502 | 0.012 | 0.090 | 9.358 |
| 17 | 10.000 | 0.627 | 0.020 | 0.088 | 10.000 |
| 18 | 10.000 | 0.066 | 0.003 | 0.021 | 6.014 |
| 19 | 10.000 | 0.034 | 0.007 | 0.056 | 10.000 |
| 20 | 9.961 | 0.053 | 0.008 | 0.030 | 3.393 |
| 21 | 10.000 | 0.068 | 0.002 | 0.025 | 10.000 |
| 22 | 10.000 | 0.106 | 0.003 | 0.048 | 5.346 |

The data shows that the compounds of the invention inhibit KIT carrying both primary and secondary KIT mutations simultaneously, and furthermore, are selective against KDR. In some embodiments, pharmaceutically acceptable salts of the compounds of Formula (I) convert to the free base form in vivo. For example, the tosylate salt of Example 12 (also referred to herein as Example 12A and Tosylate Salt Y) converts to the free base in vivo and it is the free base, rather than the tosylate salt, that passes through the cell membrane. Administration of the tosylate salt would therefore lead to the free base activity exemplified above for Example 12.

Compounds may be further selected on the basis of further biological or physical properties which may be measured by techniques known in the art and which may be used in the assessment or selection of compounds for therapeutic or prophylactic application.

As a result of their KIT inhibitory activity, the compounds of Formula (I), and pharmaceutically acceptable salts thereof are expected to be useful in therapy.

We have found that the compounds of Formula (I) possess potent anti-tumour activity which it is believed is obtained by way of inhibition of both wildtype KIT and KIT mutants. We have also found that the compounds of Formula (I) may also act partly as an immune-oncology drug.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of a compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by KIT. In one embodiment, the disease mediated by KIT is cancer. In one embodiment the cancer is selected from the group consisting of gastrointestinal stromal tumour (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is a gastrointestinal stromal tumour. GIST is a type of tumour that occurs in the gastrointestinal tract, most commonly in the stomach or small intestine.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by KIT. In one embodiment, the disease mediated by KIT is cancer. In one embodiment, the cancer is selected from the group consisting of gastrointestinal stromal tumors (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of KIT is beneficial in a warm-blooded animal in need of such treatment, which comprises administering to said warm-blooded animal a therapeutically effective amount of a compound of Formula (I), or a pharmaceutically acceptable salt thereof. In one embodiment, the disease is cancer. In one embodiment, the cancer is selected from the group consisting of gastrointestinal stromal tumors (GIST), melanomas, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is gastrointestinal stromal tumour.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of KIT activity. For cancer therapy, efficacy in-vivo can, for example, be measured by assessing the duration of survival, time to disease progression (TP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of KIT activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is selected from the group consisting of gastrointestinal stromal tumors (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

In one embodiment the cancer is gastrointestinal stromal tumour.

The anti-cancer treatment described in this specification may be useful as a sole therapy, or may involve, in addition to administration of the compound of Formula (I), or a pharmaceutically acceptable salt thereof, conventional surgery, radiotherapy or chemotherapy; or a combination of such additional therapies. Such conventional surgery, radiotherapy or chemotherapy may be administered simultaneously, sequentially or separately to treatment with the compound of Formula (I) or a pharmaceutically acceptable salt thereof.

Where a combination therapy is administered "simultaneously", this includes treatment of a patient with a single dosage form (e.g. a tablet) comprising both a compound of Formula (I), or a pharmaceutically acceptable salt thereof and an additional anti-cancer substance; and also simultaneous dosing of separate dosage forms each separately comprising one of the respective combination partners.

Where a combination therapy is administered "sequentially" or "separately", this includes treatment of a patient with a first dosage form (e.g. a tablet) comprising a compound of Formula (I), or a pharmaceutically acceptable salt thereof, followed by treatment of the same patient with a second dosage form comprising an additional anti-cancer substance; or treatment of a patient with a single dosage form (e.g. a tablet) comprising a particular anti-cancer substance, followed by treatment of the same patient with a second dosage form comprising a compound of Formula (I), or a pharmaceutically acceptable salt thereof. The interval between the sequential or separate doses may be judged by a skilled practitioner with reference to the information in this specification.

In one embodiment there is provided a compound of Formula (I), or a pharmaceutically acceptable salt thereof, for use in the treatment of cancer, where the compound of Formula (I), or a pharmaceutically acceptable salt thereof is administered before surgery.

Administration of a compound of Formula (I), or a pharmaceutically acceptable salt thereof, before surgery to entirely or partially remove a cancer may be referred to as "neo-adjuvant therapy". In such a scenario, the goal of administering the compound of Formula (I), or a pharmaceutically acceptable salt thereof is generally to reduce the size of the target tumour in order to increase the chances of a successful resection. As such, the length of time the compound of Formula (I), or a pharmaceutically acceptable salt thereof is dosed before surgery may be judged by a skilled practitioner with reference to the information within this specification.

In one embodiment there is provided a compound of Formula (I), or a pharmaceutically acceptable salt thereof, for use in the treatment of cancer, where the compound of Formula (I), or a pharmaceutically acceptable salt thereof is administered after surgery.

In one embodiment there is provided a compound of Formula (I), or a pharmaceutically acceptable salt thereof, for use in the treatment of cancer, where the compound of Formula (I), or a pharmaceutically acceptable salt thereof is administered in combination with at least one additional anti-cancer substance.

In one embodiment there is provided a compound of Formula (I), or a pharmaceutically acceptable salt thereof, for use in the treatment of cancer, where the compound of Formula (I), or a pharmaceutically acceptable salt thereof is administered simultaneously, sequentially or separately with at least one additional anti-cancer substance.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:

(i) inhibitors of growth factor function and their downstream signalling pathways: included are Ab modulators of any growth factor or growth factor receptor targets, reviewed by Stem et al. Critical Reviews in Oncology/ Haematology, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK7, CDK9 and CDK4/6 such as palbociclib;

(ii) modulators of apoptotic and cell death pathways such as Bcl family modulators (e.g. ABT-263/Navitoclax, ABT-199);

(iii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab).

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iii) above.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier. In one embodiment the anti-tumour substance is an anti-neoplastic agent.

According to a further embodiment there is provided a kit comprising:

a) A compound of Formula (I), or a pharmaceutically acceptable salt thereof, in a first unit dosage form:

b) A further additional anti-tumour substance in a further unit dosage form;

c) Container means for containing said first and further unit dosage forms; and optionally d) Instructions for use.

The compounds of Formula (I), and pharmaceutically acceptable salts thereof, may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier. The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment, said cancer is selected from the group consisting of gastrointestinal stromal tumors (GIST), melanoma, lung cancers, glioblastoma, leukemias, testicular carcinomas and head and neck cancers. Lung cancers include small cell lung cancer (SCLC), adenocarcinomas and squamous carcinomas of the lung. Leukemias include acute myeloid leukaemia (AML) and mast cell leukemias.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-500 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work up procedures were carried out after removal of residual solids by filtration;

(iii) flash column chromatography was performed on Merck Kieselgel silica (Art. 9385) or on reversed phase silica (Fluka silica gel 90 C18) or on Silicycle cartridges (40-63 µm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 µm silica) either manually or automated using an Isco CombiFlash Companion system or similar system;

(iv) preparative reverse phase HPLC was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents;

(v) chiral HPLC methods were carried out using a Gilson GX-281 HPLC and a Daicel CHIRALPAK IC (2×25 cm, 5 um) or Daicel CHIRALPAK IF (2×25 cm, 5 um); in general a flow rate of between 10-350 ml/minute and detection was by UV absorbance at a typical wavelength of 254 nm. A sample concentration of about 1-100 mg/ml was used in a suitable solvent mixture with an injection volume of between 0.5-10 ml and run time of between 10-150 minutes and a typical oven temperature of 25-35° C.; analytical chiral HPLC methods were carried out using Shimadzu UFLC and a Daicel CHIRALPAK IC-3 (50×4.6 mm 3 um) or Daicel CHIRALPAK IF-3 (50×4.6 mm 3 um); in general a flow rate of 1 ml/minute and detection was by UV absorbance at a typical wavelength of 254 nm. A sample concentration of about 1 mg/ml was used in a suitable solvent such as EtOH with an injection volume of about 10 µl and run time of between 10-60 minutes and a typical oven temperature of 25-35° C.;

(vi) yields, where present, are not necessarily the maximum attainable;

(vii) in general, the structures of end products of the compounds of Formula (I) were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(viii) in general, end products of Formula (I) were also characterized by mass spectroscopy following liquid chromatography (LCMS or UPLC); in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the [M+H]+ unless otherwise specified; for molecules with multiple isotopic patterns (Br, Cl, etc.) the reported value is the one obtained for the lowest isotope mass unless otherwise specified;

(ix) ion exchange purification was generally performed using an SCX-2 (Biotage) cartridge;

(x) where reactions refer to the use of a microwave, one of the following microwave reactors were used: Biotage Initiator, Personal Chemistry Emrys Optimizer, Personal Chemistry Smithcreator or CEM Explorer;

(xi) intermediate purity was assessed by thin layer chromatographic, mass spectroscopy. LCMS. UPLC/MS. HPLC and/or NMR analysis;

(xii) the following abbreviations have been used:
BEH ethylene bridged hybrid
BOP (benzotriazol-1-yloxy)tris(dimethylamino)phosphonium hexafluorophosphate
DBU 1,8-diazabicyclo(5.4.0)undec-7-ene DCM dichloromethane
DEA diethylamine
DIPEA diisopropylethylamine
DMF N,N-dimethylformamide
DMF-DMA N,N-dimethylformamide dimethyl acetal
DMSO dimethylsulfoxide
e.e. enantiomeric excess
HATU (1-[bis(dimethylamino)methylene]-1H-1,2,3-triazolo[4,5-b]pyridinium 3-oxid hexafluorophosphate)
HCl hydrochloric acid
HPLC high performance liquid chromatography
MS mass spectrometry
NMR nuclear magnetic resonance
PAT process analytical technology
PyAOP ((7-azabenzotriazol-1-yloxy)tripyrrolidinophosphonium hexafluorophosphate)
PyBOP (benzotriazol-1-yl-oxytripyrrolidinophosphonium hexafluorophosphate)
TBME/MTBE tert-butyl methyl ether
TEA triethylamine
TFA trifluoroacetic acid
THF tetrahydrofuran
tR retention time
PTSA p-toluenesulfonic acid
UPLC ultra performance liquid chromatography
(xiii) XRPD: Analytical Instrument: Bruker D4

The X-ray powder diffractogram was determined by mounting a sample of the crystalline material on a Bruker (Bruker D4) single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm anti scatter slit and a 9.55 mm detector slit. Samples were measured in reflection geometry in θ-2θ configuration over the scan range 2° to 40° 2θ with a nominal 0.12 second exposure per 0.02° increment. The instrument was equipped with a Position sensitive detector (Lynxeye). Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(xiv) Differential Scanning Calorimetry: Analytical Instrument: TA Instruments Q2000 DSC Typically less than 3 mg of material contained in a standard aluminium pan fitted with a lid was heated over the temperature range 25° C. to 300° C. at a constant heating rate of 10° C. per minute. A purge gas using nitrogen was used—flow rate 50 ml per minute. Thermal data was analyzed using standard software, e.g., Universal v.4.5A from TA INSTRUMENTS®;

(xv) For the Thermogravimetry Analysis (TGA) the instrument used was TA Instruments Q5000 TGA Typically less than 5 mg was placed into an aluminum sample pan and transferred to the TGA furnace. The instrument was purged with nitrogen at 50 mL/min and data collected between 25° C. and just below the melting point of the compound, using a constant heating rate of 10° C./minute. Thermal data was analyzed using standard software, e.g., Universal v.4.5A from TA INSTRUMENTS®.

Example 1

N-(4-[(5,7-dimethoxyquinazolin-4-yl)amino]-3-fluorophenyl)-2-[4-(propan-2-yl)-1H-1,2,3-triazol-1-yl]acetamide

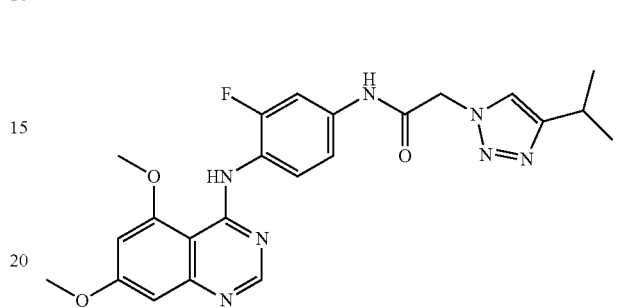

4-Chloro-5,7-dimethoxyquinazoline (78 mg, 0.4 mmol) was added to N-(4-amino-3-fluorophenyl)-2-(4-isopropyl-1H-1,2,3-triazol-1-yl)acetamide (80 mg, 0.3 mmol) in isopropanol (2.5 mL) under nitrogen. The resulting mixture was stirred at 80° C. for 4 hours. The reaction mixture was diluted with water. The precipitate was collected by filtration, washed with water (10 mL) and dried under vacuum to afford crude product as a purple solid. The crude product was purified by preparative HPLC. Fractions containing the desired compound were evaporated to dryness to afford the title compound as a beige solid (80 mg, 58%). 1H NMR (400 MHz, DMSO-d6) δ 1.25 (6H, d), 2.95-3.06 (1H, m), 3.91 (3H, s), 4.06 (3H, s), 5.29 (2H, s), 6.72 (1H, d), 6.80 (1H, d), 7.28-7.36 (1H, m), 7.67-7.75 (1H, m), 7.88 (1H, s), 8.19 (1H, t), 8.41 (1H, s), 9.81 (1H, s), 10.71 (1H, s); m/z (ES+), [M+H]+=466; acid, HPLC tR=1.53 min.

The intermediates used in Example 1 were prepared as follows:

Preparation of 2-Fluorobenzene-1,4-diamine

Zinc powder (4.2 g, 64.1 mmol) was added to ammonium chloride (3.4 g, 64.1 mmol), 3-fluoro-4-nitroaniline (500 mg, 3.2 mmol) and water (4 mL) in ethanol (15 mL) under nitrogen. The resulting mixture was stirred at 25° C. for 2 hours. The mixture was filtered, and the filtrate was evaporated to dryness to give a crude residue which was purified by flash silica chromatography, elution gradient 1 to 10% methanol in DCM (0.1% DIPEA). Pure fractions were evaporated to dryness to afford the title compound as a black oil (405 mg, 100%). 1H NMR (DMSO-d6, 300 MHz) δ 6.27 (1H, dd), 6.39 (1H, dd), 6.58 (1H, dd), 9.74 (2H, s); m/z (ES+), [M+H]+=127; acid. HPLC tR=0.227 min.

Preparation of Ethyl 2-(4-isopropyl-1H-1,2,3-triazol-1-yl)acetate

A 30% solution of ethyl 2-azidoacetate in DCM (19.5 g, 45.4 mmol) was added as a solution in acetonitrile (27 mL) over 5 minutes to a suspension of copper(I) iodide (0.17 g, 0.9 mmol), 3-methylbut-1-yne (5.1 mL, 49.9 mmol) and triethylamine (0.13 mL, 0.9 mmol) in acetonitrile (27 mL) at room temperature. The mixture was stirred for 3 days at room temperature. The mixture was concentrated and the residue was partitioned between water (150 mL) and ethyl acetate (150 mL). The aqueous layer was extracted with ethyl acetate (100 mL) and the extracts combined with the organic layer. The combined extracts were dried and evaporated to dryness. The crude product was purified by flash silica chromatography, elution gradient 30 to 50% ethyl acetate in heptane. Pure fractions were evaporated to dryness to afford the title compound as a white crystalline solid (8.06 g, 90%). 1H NMR (500 MHz, DMSO, 27° C.) δ 1.21 (3H, t), 1.22 (6H, d), 2.98 (1H, hept), 4.16 (2H, q), 5.30 (2H, s), 7.82 (1H, d); m/z: ES+ [M+H]+ 198.

Preparation of 2-(4-Isopropyl-1H-1,2,3-triazol-1-yl)acetic acid

Lithium hydroxide hydrate (10.2 g, 242.5 mmol) was added as a solution in water (540 mL) to ethyl 2-(4-isopropyl-1H-1,2,3-triazol-1-yl)acetate (15.9 g, 80.8 mmol) in THF (180 mL). The mixture was stirred for 90 minutes, then concentrated. The resulting aqueous solution was acidified to pH 5 with 2M HCl and extracted with ethyl acetate (200 mL). The aqueous layer was evaporated to dryness to afford the title compound as a white solid containing LiCl (28.2 g, 100%, 48% strength), which was used without further purification. 1H NMR (500 MHz, DMSO, 27° C.) δ 1.20 (6H, d), 2.92 (1H, hept), 4.59 (2H, s), 7.62 (1H, d); m/z: ES+ [M+H]+170.

Preparation of N-(4-Amino-3-fluorophenyl)-2-(4-isopropyl-1H-1,2,3-triazol-1-yl)acetamide HATU (678 mg, 1.8 mmol) was added to 2-(4-isopropyl-1H-1,2,3-triazol-1-yl)acetic acid (201 mg, 1.2 mmol), 2-fluorobenzene-1,4-diamine (150 mg, 1.2 mmol) and DIPEA (0.3 mL, 1.8 mmol) in DMF (7 mL) under nitrogen. The resulting mixture was stirred at 25° C. for 6 hours, then evaporated to dryness. The crude product was purified by preparative HPLC. Fractions containing the desired compound were evaporated to dryness to afford the title compound as a black solid (200 mg, 61%). 1H NMR (DMSO-d6, 400 MHz) δ 1.24 (6H, d), 2.99 (1H, dt), 4.98 (2H, s), 5.18 (2H, s), 6.72 (1H, dd), 6.99 (1H, dd), 7.38 (1H, dd), 7.85 (1H, s), 10.25 (1H, s); m/z (ES+), [M+H]+=278; acid, HPLC tR=0.979 min.

Example 2

N-{4-[(5-fluoro-6,7-dimethoxyquinazolin-4-yl)amino]phenyl}-2-[4-(propan-2-yl)-1H-1,2,3-triazol-1-yl]acetamide

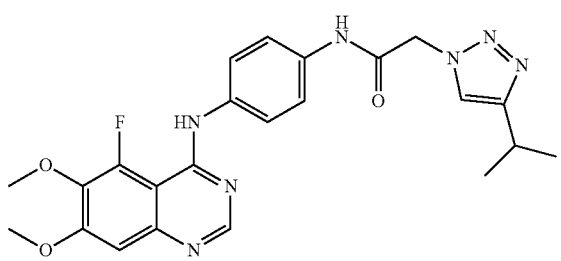 [SMILES: COc1cc2ncnc(Nc3ccc(NC(=O)Cn4cc(C(C)C)nn4)cc3)c2c(F)c1OC]

HATU (84 mg, 0.2 mmol) was added portionwise to N1-(5-fluoro-6,7-dimethoxyquinazolin-4-yl)benzene-1,4-diamine (100 mg, 0.2 mmol), 2-(4-isopropyl-1H-1,2,3-triazol-1-yl)acetic acid (52 mg, 0.2 mmol) and DIPEA (0.06 mL, 0.4 mmol) in DMF (1 mL) at 25° C. under nitrogen. The resulting solution was stirred at room temperature for 1 hour. The reaction mixture was concentrated and diluted with DCM (100 mL), and washed sequentially with 0.1M HCl (20 mL), water (10 mL), and saturated Na2CO3 (20 mL). The organic layer was dried, filtered and evaporated to dryness. The crude product was purified by preparative HPLC. Fractions containing the desired compound were evaporated to dryness to afford the title compound as a white solid (60 mg, 70%). 1H NMR (400 MHz, DMSO-d6) δ 1.26 (6H, d), 2.94-3.07 (1H, m), 3.91 (3H, s), 4.00 (3H, s), 5.27 (2H, s), 7.15 (1H, d), 7.59 (2H, d), 7.69 (2H, d), 7.88 (1H, d), 8.45 (1H, s), 8.94 (1H, d), 10.48 (1H, s); m/z (ES+), [M+H]+=466; acid, HPLC tR=1.38 min.

The intermediates used in Example 2 were prepared as follows:

Preparation of 2-Fluoro-3,4-dimethoxybenzaldehyde

Titanium(IV)chloride (8 g, 42.3 mmol) in DCM (12 mL) was added dropwise to 1-fluoro-2,3-dimethoxybenzene (4 g, 25.6 mmol) in DCM (40 mL) at 0° C. over a period of 15 minutes under nitrogen. This was followed by the addition of dichloro(methoxy)methane (3.2 g, 28.2 mmol) in anhydrous DCM (8 mL) dropwise over 12 minutes. The resulting solution was stirred at 0° C. for 30 minutes, then stirred at room temperature for 5 hours. The reaction mixture was quenched with water (200 mL), extracted with DCM (2×100 mL), the organic layer was dried, filtered and evaporated to dryness. The crude product was purified by flash silica chromatography, elution gradient 0 to 2% methanol in DCM. Pure fractions were evaporated to dryness to afford the title compound (4.6 g, 98%) as a yellow solid. 1H NMR (DMSO-d6, 300 MHz) δ 3.84 (3H, d), 3.95 (3H, s), 7.11 (1H, p), 7.61 (1H, p), 10.06 (1H, s); m/z (ES+), [M+H]+=185; acid, HPLC tR=1.434 min.

Preparation of 2-Fluoro-3,4-dimethoxy-6-nitrobenzaldehyde

Potassium nitrate (2.8 g, 27.4 mmol) was added portionwise to 2-fluoro-3,4-dimethoxybenzaldehde (4.2 g, 22.8 mmol) and concentrated sulfuric acid (30 ml, 562.9 mmol) at 0° C. The resulting solution was stirred at room temperature for 3 hours. The reaction mixture was poured into ice water. The precipitate was collected by filtration, washed with ice water (75 mL) and dried under vacuum to afford the title compound as a brown solid (3.2 g, 61%). 1H NMR (DMSO-d6, 300 MHz) δ 3.95 (3H, d), 4.02 (3H, s), 7.71 (1H, d), 10.08 (1H, s); m/z (ES+), [M+H]+=230; acid, HPLC tR=1.206 min.

Preparation of 2-Fluoro-3,4-dimethoxy-6-nitrobenzoic acid

Sodium perborate (4.3 g, 27.9 mmol) was added portionwise to 2-fluoro-3,4-dimethoxy-6-nitrobenzaldehyde (3.2 g, 14 mmol) in acetic acid (45 mL) over a period of 2 minutes. The resulting mixture was stirred at 50° C. for 3 days. The reaction mixture was evaporated to dryness and dissolved in DCM (200 mL), and washed sequentially with water (2×100 mL). The aqueous layer was separated, frozen and lyophilized to afford the title compound as yellow solid (2.9 g, 85%). 1H NMR (DMSO-d6, 300 MHz) δ 3.89 (6H, d), 7.41 (1H, d); m/z (ES+), [M+H]+=not found; acid. HPLC tR=1.041 min.

Preparation of 2-Fluoro-3,4-dimethoxy-6-nitrobenzamide

SOCl$_2$ (100 mL, 1370 mmol) was added portionwise to 2-fluoro-3,4-dimethoxy-6-nitrobenzoic acid (2.9 g, 11.8 mmol). The resulting mixture was stirred at 90° C. for 2 hours. The solvent was removed under reduced pressure and the resulting residue was dissolved in THF (30 mL). The solvent was cooled to 0° C. and ammonia (0.5M in THF) (47.3 mL, 23.7 mmol) was added slowly. The resulting solution was stirred at room temperature for 2 hours. The reaction mixture was evaporated to dryness and dissolved in DCM (200 mL), and washed sequentially with saturated NaHCO$_3$ (2×50 mL) and water (2×50 mL). The organic layer was dried, filtered and evaporated to dryness. The crude product was purified by flash silica chromatography, elution gradient 0 to 6% methanol in DCM. Pure fractions were evaporated to dryness to afford the title compound as a brown solid (0.6 g, 21%). 1H NMR (DMSO-d6, 300 MHz) δ 3.98 (6H, d), 7.69 (1H, d).

Preparation of 6-Amino-2-fluoro-3,4-dimethoxybenzamide

Iron (412 mg, 7.4 mmol) was added portionwise to 2-fluoro-3,4-dimethoxy-6-nitrobenzamide (600 mg, 2.5 mmol) in acetic acid (3 mL). The resulting mixture was stirred at 105° C. for 15 minutes. The reaction mixture was evaporated to dryness and dissolved in DCM (100 mL), and washed sequentially with water (2×50 mL). The organic layer was dried, filtered and evaporated to afford the title compound as a yellow oil (500 mg, 95%), which was used without further purification. m/z (ES+), [M+H]+=215; acid, HPLC tR=0.964 min.

Preparation of 5-Fluoro-6,7-dimethoxyquinazolin-4(3H)-one

PTSA (35.5 mg, 0.2 mmol) was added to 6-amino-2-fluoro-3,4-dimethoxybenzamide (200 mg, 0.9 mmol) and trimethoxymethane (5 mL) at 25° C. under nitrogen. The resulting suspension was stirred at 100° C. for 3 hours. The reaction was cooled to room temperature. The precipitate was collected by filtration, washed with ethyl acetate (5 mL) and evaporated to dryness to afford the title compound as a beige solid (140 mg, 67%), which was used without further purification. 1H NMR (400 MHz, DMSO-d6) δ 3.83 (3H, s), 3.95 (3H, s), 7.01-7.08 (1H, m), 8.00 (1H, d), 12.12 (1H, s); m/z (ES+), [M+H]+=225; acid, HPLC tR=0.87 min.

Preparation of N1-(5-Fluoro-6,7-dimethoxyquinazolin-4-yl)benzene-1,4-diamine PyAOP (393 mg, 0.8 mmol) was added to 5-fluoro-6,7-dimethoxyquinazolin-4(3H)-one (130 mg, 0.6 mmol) and DBU (0.22 mL, 1.5 mmol) in acetonitrile (4 mL) at 25° C. under nitrogen. The resulting solution was stirred at room temperature for 10 minutes. Benzene-1,4-diamine (94 mg, 0.9 mmol) was added to this at 25° C. under nitrogen. The resulting solution was stirred at room temperature for 3 hours. The reaction mixture was quenched with water (20 mL), extracted with DCM (2×25 mL), the organic layer was dried, filtered and evaporated to afford a dark oil which solidified on standing. The crude product was purified by flash silica chromatography, elution gradient 0 to 2% methanol in DCM. Pure fractions were evaporated to dryness to afford the title compound as a yellow solid (220 mg, >100%). 1H NMR (400 MHz, DMSO-d6) δ 3.89 (3H, s), 3.98 (3H, s), 5.05 (2H, s), 6.57 (2H, d), 7.09 (1H, s), 7.26 (2H, d), 8.34 (1H, s), 8.65 (1H, d); m/z (ES+), [M+H]+=315; acid, HPLC tR=0.87 min.

Example 3 and Example 4

(R)—N-(4-{[5-Ethoxy-7-(tetrahydrofuran-3-yloxy) quinazolin-4-yl]amino}phenyl)-2-[4-(propan-2-yl)-1H-1,2,3-triazol-1-yl]acetamide and (S)—N-(4-{[5-Ethoxy-7-(tetrahydrofuran-3-yloxy)quinazolin-4-yl] amino}phenyl)-2-[4-(propan-2-yl)-1H-1,2,3-triazol-1-yl]acetamide

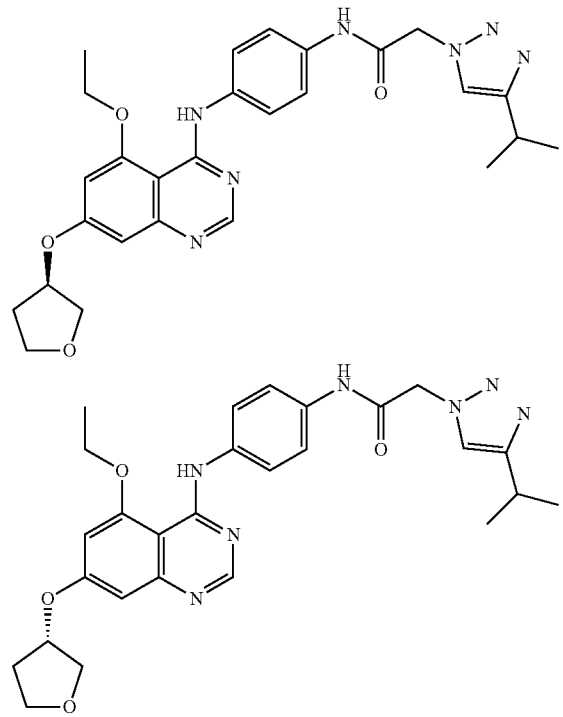

Potassium tert-butoxide (150 mg, 1.3 mmol) was added to tetrahydrofuran-3-ol (78 mg, 0.9 mmol) and N-(4-((5-ethoxy-7-fluoroquinazolin-4-yl)amino)phenyl)-2-(4-isopropyl-1H-1,2,3-triazol-1-yl)acetamide (200 mg, 0.4 mmol) in DMF (4 mL) at 25° C. under air. The resulting mixture was stirred at 80° C. for 5 hours. The crude product was purified by preparative HPLC. Fractions containing the desired compound were evaporated to dryness to afford the racemic title compound as a white solid (160 mg, 70%); m/z (ES+), [M+H]+=518; TFA, HPLC tR=1.443 min. This compound was purified by preparative chiral-HPLC on a Chiralpak IA column, eluting isocratically with 30% ethanol in MTBE (0.1% DEA) as eluent. The fractions containing the desired compound were evaporated to dryness to afford one enantiomer of N-(4-((5-ethoxy-7-((tetrahydrofuran-3-yl) oxy)quinazolin-4-yl)amino)phenyl)-2-(4-isopropyl-1H-1,2,3-triazol-1-yl)acetamide as a white solid (68 mg, 43%). 1H NMR (400 MHz, DMSO, 20° C.) δ 1.25 (6H, d), 1.56 (3H, t), 1.99-2.06 (1H, m), 2.25-2.35 (1H, m), 2.95-3.02 (1H, m), 3.75-3.95 (4H, m), 4.32 (2H, t), 5.22 (1H, t), 5.27 (2H, s), 6.68 (1H, s), 6.76 (1H, s), 7.60 (2H, d), 7.78 (2H, d), 7.88 (1H, s), 8.46 (1H, s), 9.98 (1H, s), 10.50 (1H, s); m/z (ES+),

[M+H]+=518; TFA, HPLC tR=1.463 min. This was then followed by the other enantiomer of N-(4-((5-ethoxy-7-((tetrahydrofuran-3-yl)oxy)quinazolin-4-yl)amino)phenyl)-2-(4-isopropyl-1H-1,2,3-triazol-1-yl)acetamide as a white solid (62 mg, 39%). 1H NMR (400 MHz, DMSO, 20° C.) δ 1.25 (6H, d), 1.56 (3H, t), 1.98-2.05 (1H, m), 2.25-2.35 (1H, m), 2.95-3.02 (1H, m), 3.75-3.95 (4H, m), 4.32 (2H, t), 5.22 (1H, t), 5.27 (2H, s), 6.68 (1H, s), 6.76 (1H, s), 7.60 (2H, d), 7.78 (2H, d), 7.88 (1H, s), 8.46 (1H, s), 9.99 (1H, s), 10.50 (1H, s); m/z (ES+), [M+H]+=518; TFA, HPLC tR=1.470 min.

The intermediates used in Example 3 and Example 4 were prepared as follows:

Preparation of
5-Ethoxy-7-fluoroquinazolin-4(3H)-one

Sodium ethanolate (7.5 g, 109.8 mmol) was added to 5,7-difluoroquinazolin-4(3H)-one (4 g, 22 mmol) in DMSO (20 mL) cooled at 0° C. under nitrogen. The resulting solution was stirred at room temperature for 2 hours. The reaction mixture was diluted with water (200 mL) and adjusted to pH 7 with 2M HCl. The resulting solid was isolated by filtration to afford the title compound as yellow solid (4.4 g, 96%). 1H NMR (300 MHz, DMSO, 21° C.) δ 1.37 (3H, t), 4.09-4.16 (2H, m), 6.88-6.94 (2H, m), 7.98 (1H, s), 11.98 (1H, s); m/z (ES+), [M+H]+=209; TFA, HPLC tR=0.988 min.

Preparation of N1-(5-Ethoxy-7-fluoroquinazolin-4-yl)benzene-1,4-diamine

BOP (8.9 g, 20.2 mmol) was added to 5-ethoxy-7-fluoroquinazolin-4(3H)-one (3 g, 14.4 mmol) and DBU (4.3 mL, 28.8 mmol) in acetonitrile (20 mL) at 25° C. under nitrogen. The resulting solution was stirred at 60° C. for 3 hours. Benzene-1,4-diamine (2.2 g, 20.2 mmol) was added to this at 25° C. under nitrogen. The resulting solution was stirred at 60° C. for 3 hours. The solvent was removed under reduced pressure. The reaction mixture was quenched with water (10 mL), extracted with DCM (3×25 mL), the organic layer was dried, filtered and evaporated to afford a dark oil. The crude product was purified by flash silica chromatography, elution gradient 0 to 4% methanol in DCM. Pure fractions were evaporated to dryness to afford the title compound as a yellow solid (2.6 g, 59%). 1H NMR (300 MHz, DMSO, 23° C.) δ 1.68 (3H, t), 4.27-4.29 (2H, m), 6.65 (1H, s), 6.74-6.77 (2H, m), 7.06 (1H, d), 7.45-7.48 (2H, m), 8.54 (1H, d), 9.69 (1H, s); m/z (ES+), [M+H]+=299; TFA, HPLC tR=0.871 min.

Preparation of N-(4-((5-Ethoxy-7-fluoroquinazolin-4-yl)amino)phenyl)-2-(4-isopropyl-1H-1,2,3-triazol-1-yl)acetamide HATU (4.7 g, 12.3 mmol) was added to N1-(5-ethoxy-7-fluoroquinazolin-4-yl)benzene-1,4-diamine (2.5 g, 8.2 mmol), 2-(4-isopropyl-1H-1,2,3-triazol-1-yl)acetic acid (2.1 g, 12.3 mmol) and DIPEA (4.3 mL, 24.6 mmol) in DMF (10 mL) at 25° C. under air. The resulting mixture was stirred at room temperature for 2 hours. The reaction mixture was diluted with ethyl acetate (150 mL), and washed sequentially with water (2×150 mL) and saturated brine (75 mL). The organic layer was dried, filtered and evaporated to dryness. The crude product was purified by flash silica chromatography, elution gradient 0 to 4% methanol in DCM. Pure fractions were evaporated to dryness to afford the title compound as a yellow solid (1.5 g, 41%). 1H NMR (300 MHz, DMSO, 23° C.) δ 1.25 (6H, d), 1.58 (3H, t), 2.95-3.05 (1H, m), 4.35-4.42 (2H, m), 5.26 (2H, s), 7.05-7.12 (2H, m), 7.60-7.63 (2H, m), 7.77-7.80 (2H, m), 7.87 (1H, s), 8.50 (1H, s), 10.03 (1H, s), 10.51 (1H, s); m/z (ES+), [M+H]+=450; TFA, HPLC tR=1.048 min.

Example 5

N-(4-((5-Ethoxy-7-((tetrahydro-2H-pyran-4-yl)oxy)quinazolin-4-yl)amino)phenyl)-2-(4-isopropyl-1H-1,2,3-triazol-1-yl)acetamide

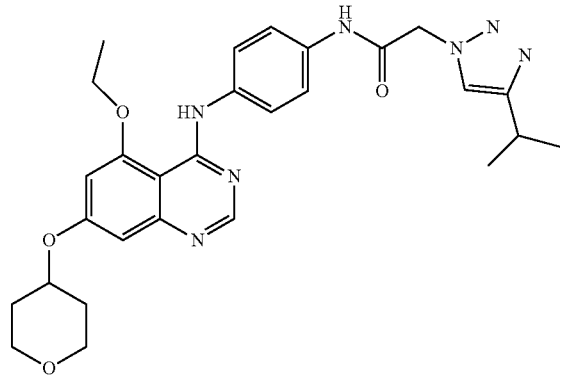 [SMILES: CCOc1cc(OC2CCOCC2)cc2ncnc(Nc3ccc(NC(=O)CN(N)/C=C(\N)C(C)C)cc3)c12]

Potassium tert-butoxide (112 mg, 1 mmol) was added to N-(4-((5-ethoxy-7-fluoroquinazolin-4-yl)amino)phenyl)-2-(4-isopropyl-1H-1,2,3-triazol-1-yl)acetamide (150 mg, 0.3 mmol) and tetrahydro-4H-pyran-4-ol (102 mg, 1 mmol) in DMF (2 mL) at room temperature. The resulting solution was stirred at 80° C. for 7 hours. The crude product was purified by preparative HPLC. Fractions containing the desired compound were evaporated to dryness to afford the title compound (75 mg, 42%) as a white solid. 1H NMR (DMSO-d6, 400 MHz) δ 1.26 (6H, d), 1.58 (3H, t), 1.65 (2H, t), 2.01-2.11 (2H, m), 2.95-3.07 (1H, m), 3.52-3.58 (2H, m), 3.86-3.91 (2H, m), 4.35 (2H, q), 4.80-4.86 (1H, m), 5.27 (2H, s), 6.70 (1H, d), 6.88 (1H, d), 7.57-7.65 (2H, m), 7.75-7.84 (2H, m), 7.89 (1H, d), 8.44 (1H, s), 9.98 (1H, s), 10.50 (1H, s); m/z (ES+), [M+H]+=532; acid, HPLC tR=1.485 min.

Example 6

N-(4-((7-(2-(Dimethylamino)ethoxy)-5-ethoxyquinazolin-4-yl)amino)phenyl)-2-(4-isopropyl-1H-1,2,3-triazol-1-yl)acetamide

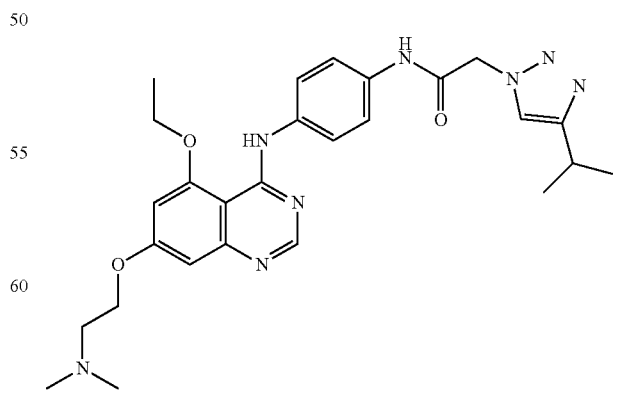

Potassium tert-butoxide (75 mg, 0.7 mmol) was added to 2-(dimethylamino)ethan-1-ol (39.7 mg, 0.4 mmol) and N-(4-((5-ethoxy-7-fluoroquinazolin-4-yl)amino)phenyl)-2-(4-isopropyl-1H-1,2,3-triazol-1-yl)acetamide (100 mg, 0.2 mmol) in DMF (2 mL) at 25° C. under air. The resulting mixture was stirred at 80° C. for 15 hours. The crude product was purified by preparative HPLC. Fractions containing the desired compound were evaporated to dryness to afford the title compound as a light yellow solid (51 mg, 44%). 1H NMR (400 MHz DMSO, 20° C.) δ 1.26 (6H, d), 1.58 (3H, t), 2.25 (6H, s), 2.65-2.69 (2H, t), 2.95-3.05 (1H, m), 4.19 (2H, t), 4.31-4.36 (2H, m), 5.27 (2H, s), 6.90 (1H, s), 6.80 (1H, s), 7.61 (2H, d), 7.78 (2H, d), 7.88 (1H, s), 8.45 (1H, s), 9.97 (1H, s), 10.50 (1H, s); m/z (ES+), [M+H]+=519; TFA, HPLC tR=1.193 min.

Example 7

N-(4-((5-Ethoxy-7-methoxyquinazolin-4-yl)amino)phenyl)-2-(4-isopropyl-1H-1,2,3-triazol-1-yl)acetamide

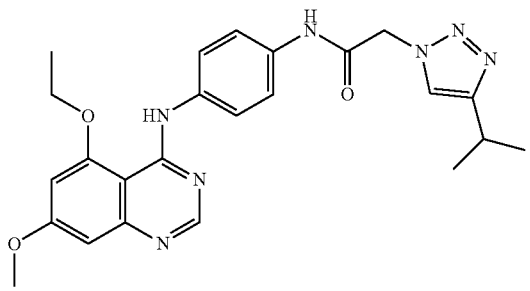 [SMILES: CCOc1cc(OC)cc2ncnc(Nc3ccc(NC(=O)Cn4cc(C(C)C)nn4)cc3)c12]

Sodium methoxide (24 mg, 0.4 mmol) was added to methanol (43 mg, 1.3 mmol) and N-(4-((5-ethoxy-7-fluoroquinazolin-4-yl)amino)phenyl)-2-(4-isopropyl-1H-1,2,3-triazol-1-yl)acetamide (100 mg, 0.2 mmol) in DMF (2 mL) at 25° C. under air. The resulting mixture was stirred at room temperature for 5 hours. The crude product was purified by preparative HPLC. Fractions containing the desired compound were evaporated to dryness to afford the title compound as a white solid (70 mg, 68%). 1H NMR (400 MHz, DMSO, 20° C.) δ 1.26 (6H, d), 1.58 (3H, t), 2.95-3.05 (1H, m), 3.90 (3H, s), 4.31-4.36 (2H, m), 5.27 (2H, s), 6.70 (1H, s), 6.79 (1H, s), 7.61 (2H, d), 7.79 (2H, d), 7.88 (1H, s), 8.46 (1H, s), 9.97 (1H, s), 10.50 (1H, s). m/z (ES+), [M+H]+=462; TFA, HPLC tR=1.445 min.

Example 8

N-(4-((5-Ethoxy-7-(2-methoxyethoxy)quinazolin-4-yl)amino)phenyl)-2-(4-isopropyl-1H-1,2,3-triazol-1-yl)acetamide

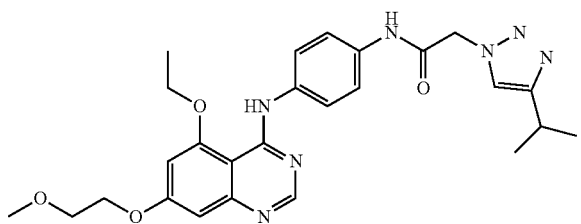 [SMILES: CCOc1cc(OCCOC)cc2ncnc(Nc3ccc(NC(=O)CN(N)/C=C(\N)C(C)C)cc3)c12]

2-Methoxyethan-1-ol (34 mg, 0.4 mmol) was added to N-(4-((5-ethoxy-7-fluoroquinazolin-4-yl)amino)phenyl)-2-(4-isopropyl-1H-1,2,3-triazol-1-yl)acetamide (100 mg, 0.2 mmol) and potassium tert-butoxide (75 mg, 0.7 mmol) in DMF (2 mL) at 25° C. under air. The resulting mixture was stirred at 80° C. for 5 hours. The crude product was purified by preparative HPLC. Fractions containing the desired compound were evaporated to dryness to afford the title compound as a white solid (63 mg, 56%). 1H NMR (400 MHz, DMSO, 20° C.) δ 1.26 (6H, d), 1.58 (3H, t), 2.95-3.05 (1H, m), 3.34 (3H, s), 3.71 (2H, t), 4.25 (2H, t), 4.31-4.36 (2H, m), 5.27 (2H, s), 6.72 (1H, s), 6.79 (1H, s), 7.61 (2H, d), 7.78 (2H, d), 7.88 (1H, s), 8.45 (1H, s), 9.97 (1H, s), 10.50 (1H, s); m/z (ES+), [M+H]+=506; TFA, HPLC tR=1.445 min.

Example 9

N-(4-((5-Ethoxy-7-(oxetan-3-yloxy)quinazolin-4-yl)amino)phenyl)-2-(4-isopropyl-1H-1,2,3-triazol-1-yl)acetamide

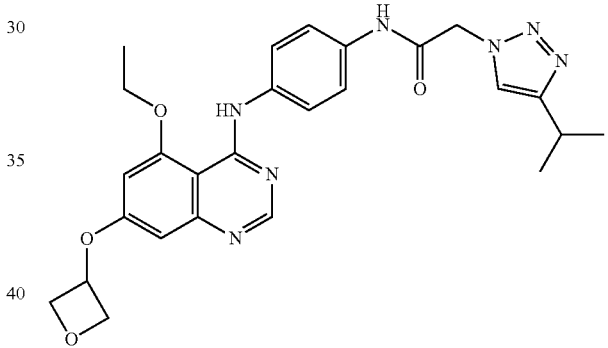

Potassium tert-butoxide (50 mg, 0.4 mmol) was added to oxetan-3-ol (33 mg, 0.4 mmol) and N-(4-((5-ethoxy-7-fluoroquinazolin-4-yl)amino)phenyl)-2-(4-isopropyl-1H-1,2,3-triazol-1-yl)acetamide (100 mg, 0.2 mmol) in DMF (2 mL) at 25° C. under air. The resulting mixture was stirred at 80° C. for 5 hours. The crude product was purified by preparative HPLC. Fractions containing the desired compound were evaporated to dryness to afford the title compound as a white solid (68 mg, 61%). 1H NMR (400 MHz, DMSO, 20° C.) δ 1.26 (6H, d), 1.58 (3H, t), 2.98-3.05 (1H, m), 4.33-4.38 (2H, m), 4.60 (2H, t), 5.00 (2H, t), 5.27 (2H, s), 5.45-5.50 (1H, m), 6.46 (1H, s), 6.72 (1H, s), 7.61 (2H, d), 7.78 (2H, d), 7.88 (1H, s), 8.45 (1H, s), 9.97 (1H, s), 10.50 (1H, s); m/z (ES+), [M+H]+=504; TFA, HPLC tR=1.883 min.

Example 10

N-(4-{[5-Methoxy-7-(tetrahydro-2H-pyran-4-yloxy)quinazolin-4-yl]amino}phenyl)-2-[4-(propan-2-yl)-1H-1,2,3-triazol-1-yl]acetamide

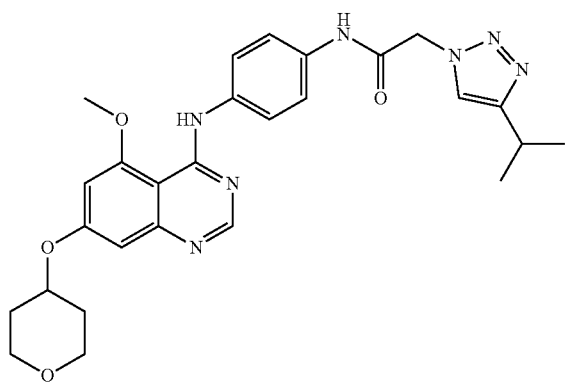 [SMILES: COc1cc(OC2CCOCC2)cc2ncnc(Nc3ccc(NC(=O)Cn4cc(C(C)C)nn4)cc3)c12]

Potassium tert-butoxide (85 mg, 0.8 mmol) was added to N-(4-((7-fluoro-5-methoxyquinazolin-4-yl)amino)phenyl)-2-(4-isopropyl-1H-1,2,3-triazol-1-yl)acetamide (110 mg, 0.3 mmol) and tetrahydro-4H-pyran-4-ol (77 mg, 0.8 mmol) in DMF (3 mL) at room temperature. The resulting solution was stirred at 80° C. for 7 hours. The crude product was purified by preparative HPLC. Fractions containing the desired compound were evaporated to dryness to afford the title compound as a white solid (38 mg, 29%). 1H NMR (DMSO-d6, 400 MHz) δ 1.26 (6H, d), 1.60-1.69 (2H, m), 2.05 (2H, d), 2.95-3.10 (1H, m), 3.56 (2H, t), 3.89 (2H, t), 4.09 (3H, s), 4.81-4.85 (1H, m), 5.27 (2H, s), 6.69 (1H, d), 6.87 (1H, d), 7.57-7.66 (2H, m), 7.74-7.84 (2H, m), 7.89 (1H, d), 8.40 (1H, s), 9.78 (1H, s), 10.52 (1H, d); m/z (ES+), [M+H]+=518; TFA, HPLC tR=8.32 min.

The intermediates used in Example 10 were prepared as follows:

Preparation of 7-Fluoro-5-methoxyquinazolin-4(3H)-one

Sodium methoxide (in methanol) (9.9 g, 54.9 mmol) was added to 5,7-difluoroquinazolin-4(3H)-one (2 g, 11 mmol) in DMSO (10 mL) cooled to 0° C. under nitrogen. The resulting solution was stirred at room temperature for 2 hours. The reaction mixture was diluted with water then neutralised with 2M HCl. The resulting precipitate was collected by filtration, washed with water (20 mL) and dried under vacuum to afford the title compound as a white solid (1.9 g, 89%), which was used without further purification. 1H NMR (300 MHz, DMSO-d6) δ 3.87 (3H, s), 6.87-7.03 (2H, m), 8.00 (1H, s), 12.04 (1H, s); m/z (ES+), [M+H]+=195; acid, HPLC tR=0.90 min.

Preparation of N1-(7-Fluoro-5-methoxyquinazolin-4-yl)benzene-1,4-diamine

BOP (3.2 g, 7.2 mmol) was added to 7-fluoro-5-methoxyquinazolin-4(3H)-one (1 g, 5.2 mmol) and DBU (1.6 mL, 10.3 mmol) in acetonitrile (20 mL) at 25° C. under nitrogen. The resulting solution was stirred at 60° C. for 15 minutes. Benzene-1,4-diamine (0.8 g, 7.2 mmol) was added to this at 25° C. under nitrogen. The resulting solution was stirred at 60° C. for 1 hour. The solvent was removed under reduced pressure. The reaction mixture was quenched with water (10 mL), extracted with DCM (3×25 mL), the organic layer was dried, filtered and evaporated to afford a dark oil. The crude product was purified by flash silica chromatography, elution gradient 0 to 4% methanol in DCM. Pure fractions were evaporated to dryness to afford the title compound as a yellow solid (2.1 g, >100%). 1H NMR (400 MHz, DMSO-d6) δ 4.10 (3H, s), 5.12 (2H, s), 6.59 (2H, d), 6.97-7.07 (2H, m), 7.31 (2H, d), 8.34 (1H, s), 9.59 (1H, s); m/z (ES+), [M+H]+=285; acid, HPLC tR=0.81 min.

Preparation of N-(4-((7-Fluoro-5-methoxyquinazolin-4-yl)amino)phenyl)-2-(4-isopropyl-1H-1,2,3-triazol-1-yl)acetamide HATU (1.9 g, 4.9 mmol) was added portionwise to N1-(7-fluoro-5-methoxyquinazolin-4-yl)benzene-1,4-diamine (2.1 g, 4.4 mmol), 2-(4-isopropyl-1H-1,2,3-triazol-1-yl)acetic acid (1.2 g, 4.9 mmol) and DIPEA (1.70 mL, 9.8 mmol) in acetonitrile (100 mL) at 25° C. under nitrogen. The resulting solution was stirred at room temperature for 1 hour. The solvent was removed under reduced pressure. The reaction mixture was diluted with water. The precipitate was collected by filtration, washed with water/acetonitrile (50 mL, 5:1) and dried under vacuum to afford the title compound as a pale yellow solid (1.2 g, 62%), which was used without further purification. 1H NMR (400 MHz, DMSO-d6) δ 1.25 (6H, d), 2.95-3.05 (1H, m), 4.13 (3H, s), 5.27 (2H, s), 7.01-7.14 (2H, m), 7.61 (2H, d), 7.75 (2H, d), 7.88 (1H, d), 8.46 (1H, s), 9.87 (1H, s), 10.51 (1H, s); m/z (ES+), [M+H]+=436; base, HPLC tR=0.82 min.

Example 11

2-[4-(Propan-2-yl)-1H-1,2,3-triazol-1-yl]-N-{4-[(5,6,7-trimethoxyquinazolin-4-yl)amino]phenyl}acetamide

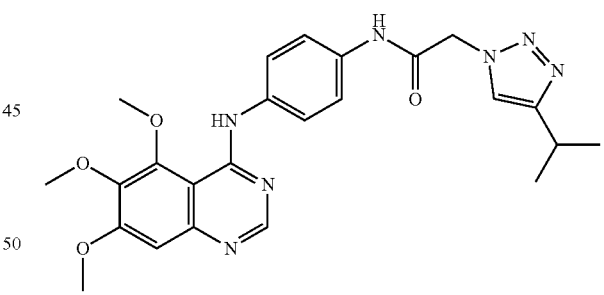

HATU (64 mg, 0.2 mmol) added to suspension of 2-(4-isopropyl-1H-1,2,3-triazol-1-yl)acetic acid (42 mg, 0.1 mmol), N1-(5,6,7-trimethoxyquinazolin-4-yl)benzene-1,4-diamine (44 mg, 0.1 mmol) and N-ethyl-N-isopropylpropan-2-amine (0.05 mL, 0.3 mmol) in DMF (5 mL). The reaction was stirred at ambient temperature for 16 hours. The reaction mixture was quenched with water (10 mL), diluted with ethyl acetate (10 mL) and the layers were separated. The aqueous layer was washed with ethyl acetate (3×10 mL) and the organic layers were combined, washed with brine (10 mL), dried, filtered and concentrated in vacuo. The crude product was purified by preparative HPLC. Fractions containing the desired compound were evaporated to dryness to afford the title compound as a white solid (41 mg, 76%). 1H NMR (500 MHz, DMSO, 27° C.) δ 1.24 (3H, s), 1.25 (3H, s), 2.99 (1H, pd), 3.86 (3H, s), 3.95 (3H, s), 4.12 (3H, s), 5.25 (2H, s), 7.06 (1H, s), 7.59 (2H, d), 7.82 (2H, d), 7.86 (1H, d), 8.43 (1H, s), 9.88 (1H, s), 10.45 (1H, s); m/z: ES+ [M+H]+ 478.

The intermediates used in Example 11 were prepared as follows:

Preparation of
5,6,7-Trimethoxyquinazolin-4(3H)-one

A solution of ethyl 6-amino-2,3,4-trimethoxybenzoate hydrochloride (200 mg, 0.7 mmol) and formimidamide acetate (214 mg, 2.1 mmol) were heated in 2-methoxyethanol (5 mL) at 125° C. for 2 hours. The mixture was cooled to ambient temperature and evaporated. The residue was treated with water (10 mL). The resulting precipitate was collected by filtration, washed with water and dried under vacuum to afford the title compound as a brown solid (164 mg, 100%), which was used without further purification. 1H NMR (500 MHz, CDCl₃, 27° C.) δ 3.95 (3H, s), 3.99 (2H, s), 4.02 (3H, s), 7.01 (1H, s), 7.99 (1H, s), 11.02 (1H, s). m/z: ES+ [M+H]+ 237.

Preparation of N1-(5,6,7-Trimethoxyquinazolin-4-yl)benzene-1,4-diamine

DBU (0.2 mL, 1.4 mmol) was added to a mixture of 5,6,7-trimethoxyquinazolin-4(3H)-one (130 mg, 0.6 mmol) and PyBOP (372 mg, 0.7 mmol) in acetonitrile (10 mL) and was heated at 60° C. for 1 hour. Benzene-1,4-diamine (119 mg, 1.1 mmol) was added and stirring at 60° C. was continued for a further 2 hours. The reaction mixture was cooled to room temperature and concentrated in vacuo. The crude mixture was dissolved in acetone and 2 mL of 2M HCl in diethyl ether was added to form a precipitate. The precipitate was filtered and washed with acetone, then dissolved in a saturated aqueous solution of sodium hydrogen carbonate (20 mL) and ethyl acetate (20 mL). The layers were separated and the aqueous layer was extracted with ethyl acetate (3×20 mL). The combined organic layers were dried, filtered and concentrated in vacuo to afford the title compound as a beige solid (73 mg, 41%), which was used without further purification. m/z: ES+ [M+H]+ 327.

Example 12

N-(4-{[5-Fluoro-7-(2-methoxyethoxy)quinazolin-4-yl]amino}phenyl)-2-[4-(propan-2-yl)-1H-1,2,3-triazol-1-yl]acetamide

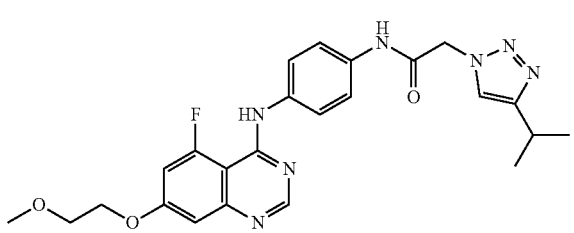 [SMILES: COCCOc1cc(F)c2c(Nc3ccc(NC(=O)Cn4cc(C(C)C)nn4)cc3)ncnc2c1]

A mixture of N-(4-aminophenyl)-2-(4-isopropyl-1H-1,2,3-triazol-1-yl)acetamide (5.4 g, 20.7 mmol) and (E)-N'-(2-cyano-3-fluoro-5-(2-methoxyethoxy)phenyl)-N,N-dimethylformimidamide (5.2 g, 19.7 mmol) in acetic acid (12 mL) was stirred at 60° C. for 35 minutes. The mixture was poured into water (150 mL), the mixture was stirred and sonicated. The resulting precipitate was collected by filtration, washed with water and dried. The solid was dissolved in DCM/methanol (12:1, 600 mL) and the solution washed with 0.2M NaHCO₃ solution (600 mL). The aqueous layer was extracted with DCM/methanol (12:1, 2×200 mL) and the extracts combined with the organic layer. The combined organic extracts were dried, filtered and evaporated to give a beige solid. The crude product was crystallised from hot ethanol (700 mL). After cooling to ambient temperature and stirring for 2 hours, the crystalline solid was collected by filtration, washed with cold ethanol and dried under high vacuum at 50° C. to afford 7.4 g of crude product. The crude product was further purified by recrystallisation in hot ethanol (800 ml). After cooling to ambient temperature and stirring for 20 hours, the crystalline solid was collected by filtration; the solids were collected and dried under vacuum at 50° C. for 72 hours to give the title compound as a white crystalline solid (6.2 g, 58%). 1H NMR (500 MHz, DMSO, 27° C.) δ 1.24 (6H, d), 2.99 (1H, pd), 3.32 (3H, s), 3.67-3.73 (2H, m), 4.24-4.3 (2H, m), 5.26 (2H, s), 7.04 (1H, d), 7.13 (1H, dd), 7.53-7.61 (2H, m), 7.63-7.69 (2H, m), 7.86 (1H, d), 8.44 (1H, s), 8.95 (1H, d), 10.47 (1H, s); m/z: ES+ [M+H]+ 480.

The intermediates used in Example 12 were prepared as follows:

Preparation of Tert-Butyl (4-(2-(4-isopropyl-1H-1,2,3-triazol-1-yl)acetamido)phenyl)carbamate HATU (18.4 g, 48.3 mmol) was added to a solution of tert-butyl (4-aminophenyl)carbamate (8.4 g, 40.3 mmol), 2-(4-isopropyl-1H-1,2,3-triazol-1-yl)acetic acid (19.4 g, 44.3 mmol) and DIPEA (10.5 mL, 60.4 mmol) at ambient temperature. The mixture was stirred at ambient temperature for 16 hours. The mixture was concentrated to 75 mL volume, diluted with water (700 mL) and extracted with ethyl acetate (3×300 mL). The combined ethyl acetate extracts were washed with 0.5M citric acid solution (300 mL), water (4×300 mL), 0.5M NaHCO₃ solution (200 mL), water (200 mL), brine (200 mL) and dried. The solution was evaporated to dryness and the residue was recrystallised from acetonitrile to afford the title compound as a white solid (8.2 g, 57%). 1H NMR (500 MHz, DMSO, 27° C.) δ 1.23 (6H, d), 1.45 (9H, s), 2.98 (1H, hept), 5.20 (2H, s), 7.38 (2H, d), 7.44 (2H, d), 7.83 (1H, d), 9.27 (1H, s), 10.31 (1H, s). m/z: ES+ [M+H]+ 360.

Preparation of N-(4-Aminophenyl)-2-(4-isopropyl-1H-1,2,3-triazol-1-yl)acetamide

4M Hydrogen chloride in dioxane (15.3 mL, 61.2 mmol) was added to a mixture of tert-butyl (4-(2-(4-isopropyl-1H-1,2,3-triazol-1-yl)acetamido)phenyl)carbamate (2.2 g, 6.1 mmol) in DCM (20 mL) and methanol (20 mL). The mixture was stirred at ambient temperature for 3 hours, during which time an additional portion of 4M hydrogen chloride in dioxane (8.0 mL, 24 mmol) was added. The mixture was evaporated to dryness and the residue dissolved in water (70 mL). This aqueous solution was added slowly to stirred 1M potassium carbonate solution (150 mL), causing a white solid to precipitate. The mixture was stirred for 10 minutes at ambient temperature. The precipitate was collected by filtration, washed with water and dried under vacuum to afford the title compound as a white solid (1.4 g, 89%) which was used without purification. 1H NMR (500 MHz, DMSO, 27° C.) δ 1.23 (6H, d), 2.98 (1H, hept), 4.90 (2H, s), 5.14 (2H, s), 6.50 (2H, d), 7.20 (2H, d), 7.82 (1H, s), 9.99 (1H, s); m/z: ES+ [M+H]+ 260.

Preparation of 2,6-Difluoro-4-(2-methoxyethoxy)benzonitrile

1-Bromo-2-methoxyethane (8.4 mL, 89 mmol) was added to a stirred suspension of 2,6-difluoro-4-hydroxybenzonitrile (11.5 g, 74.1 mmol) and potassium carbonate (30.7 g, 222.4 mmol) in DMF (175 mL). The mixture was heated to 85° C. for 5 hours. The mixture was cooled to ambient temperature and was poured into water (1250 mL). The mixture was extracted with ethyl acetate (2×400 mL). The combined extracts were washed with water (4×400 mL), saturated brine (200 mL), dried and evaporated to dryness to give an orange oil. The crude product was purified by flash silica chromatography, elution gradient 20 to 45% ethyl acetate in heptane. Pure fractions were evaporated to dryness to afford the title compound as a white crystalline solid (16.1 g, 93%). 1H NMR (500 MHz, DMSO, 27° C.) δ 3.28 (3H, s), 3.62-3.68 (2H, m), 4.21-4.27 (2H, m), 7.05-7.14 (2H, m); m/z: ES+ [M+H]+ 214.

Preparation of 2-Amino-6-fluoro-4-(2-methoxyethoxy)benzonitrile 2,6-Difluoro-4-(2-methoxyethoxy)benzonitrile (23 g, 107.9 mmol) was split between 14 microwave vials, each containing (1.64 g, 7.7 mmol) substrate. Each batch was suspended in isopropanol (3 mL) and concentrated aqueous ammonia solution (8 mL, 3237 mmol) was added. Each vial was capped and heated to 100° C. in microwave reactors for 13 hours. All batches were combined; the solid which crystallised from solution was collected by filtration, washed with water and dried to afford the title compound as a white crystalline solid (19.6 g, 87%). 1H NMR (500 MHz, DMSO, 27° C.) δ 3.28 (3H, s), 3.57-3.64 (2H, m), 4.02-4.07 (2H, m), 6.10 (1H, dd), 6.17 (1H, dd), 6.35 (2H, s); m/z: ES− [M−H]− 209.

Preparation of (E)-N'-(2-Cyano-3-fluoro-5-(2-methoxyethoxy)phenyl)-N,N-dimethylformimidamide 1,1-Dimethoxy-N,N-dimethylmethanamine (62.6 ml, 471 mmol) was added to 2-amino-6-fluoro-4-(2-methoxyethoxy)benzonitrile (11 g, 52.3 mmol) at 25° C. The resulting solution was stirred at 80° C. for 2 hours, then cooled to room temperature. The mixture was poured into stirred water (200 mL) (exotherm, cold water cooling applied) and the reaction mixture stirred for 1 hour. The mixture was extracted with ethyl acetate (2×150 mL). The combined extracts were washed with water (3×150 mL), saturated brine (100 mL), dried and evaporated to dryness to afford the title compound as a white crystalline solid (13.9 g, 100%). 1H NMR (500 MHz, DMSO, 27° C.) δ 2.98 (3H, s), 3.07 (3H, s), 3.29 (3H, s), 3.61-3.66 (2H, m), 4.14-4.17 (2H, m), 6.55-6.6 (2H, m), 8.03 (1H, s); m/z: ES+ [M+H]+ 266.

Form A of Compound X

The final product, N-(4-{[5-Fluoro-7-(2-methoxyethoxy)quinazolin-4-yl]amino}phenyl)-2-[4-(propan-2-yl)-1H-1,2,3-triazol-1-yl]acetamide, was analysed by XRPD and DSC and found to be crystalline. XRPD of a sample of the material gave rise to a diffraction pattern as shown in FIG. 1. N-(4-{[5-Fluoro-7-(2-methoxyethoxy)quinazolin-4-yl]amino}phenyl)-2-[4-(propan-2-yl)-1H-1,2,3-triazol-1-yl]acetamide Form A is characterised by at least one peak at a 2θ value of 6.7° and 18.7°, measured using CuKα radiation. The ten most prominent peaks of the XRPD are shown in Table A.

TABLE A

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide Form A

| Angle 2-Theta (2θ) | Intensity % |
| --- | --- |
| 6.7 | 100.0 |
| 18.7 | 76.9 |
| 9.9 | 42.3 |
| 3.4 | 32.3 |
| 16.2 | 10.0 |
| 28.9 | 9.1 |
| 26.6 | 7.1 |
| 23.3 | 5.1 |
| 25.1 | 4.4 |
| 22.1 | 3.6 | wherein the 2-theta values are +/−0.2°.

DSC analysis of N-(4-{[5-Fluoro-7-(2-methoxyethoxy)quinazolin-4-yl]amino}phenyl)-2-[4-(propan-2-yl)-1H-1,2,3-triazol-1-yl]acetamide Form A showed a melting endotherm with an a melting endotherm with an onset of 235.7° C. and a peak at 237.6° C. A trace of the DSC is shown in FIG. 2.

Form B of Compound X

Form B material was produced by slurrying N-(4-{[5-Fluoro-7-(2-methoxyethoxy)quinazolin-4-yl]amino}phenyl)-2-[4-(propan-2-yl)-1H-1,2,3-triazol-1-yl]acetamide, Form A in water at room temperature. Approximately 10 mg of the original material were placed in a 1.5 ml glass vial with a magnetic stirrer bar, and approximately 0.5 ml of water added, the vial was then sealed tightly with a cap and left to stir on a magnetic stirrer plate. After approximately 4 days, the sample was removed from the plate, the cap taken off and the slurry left to dry under ambient conditions before it was analysed by XRPD, DSC and TGA. The resultant material (Form B) was determined to be crystalline by XRPD. DSC and TGA analysis show that this material corresponds to a monohydrate. There was a 4.1% weight loss observed on heating to 220° C. A trace of N-(4-{[5-Fluoro-7-(2-methoxyethoxy)quinazolin-4-yl]amino}phenyl)-2-[4-(propan-2-yl)-1H-1,2,3-triazol-1-yl]acetamide is shown in FIG. 4.

XRPD of a sample of the material gave rise to a diffraction pattern as shown in FIG. 3. N-(4-{[5-Fluoro-7-(2-methoxyethoxy)quinazolin-4-yl]amino}phenyl)-2-[4-(propan-2-yl)-1H-1,2,3-triazol-1-yl]acetamide, Form B is characterised by at least one peak at a 2θ value of 4.2° and 7.7°, measured using CuKα radiation. The ten most prominent peaks of the XRPD are shown in Table B.

TABLE B

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide Form B

| Angle 2-Theta (2θ) | Intensity % |
| --- | --- |
| 18.6 | 100 |
| 9.8 | 35.7 |
| 6.6 | 29.5 |

TABLE B-continued

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide Form B

| Angle 2-Theta (2θ) | Intensity % |
|---|---|
| 13.1 | 23.0 |
| 13.7 | 20.5 |
| 7.7 | 19.0 |
| 26.5 | 15.7 |
| 4.2 | 13.0 |
| 28.8 | 12.8 |
| 20.0 | 11.8 | wherein the 2-theta values are +/−0.2°.

Example 12.1

Scale up of N-(4-{[5-Fluoro-7-(2-methoxyethoxy)quinazolin-4-yl]amino}phenyl)-2-[4-(propan-2-yl)-1H-1,2,3-triazol-1-yl]acetamide 1st Arm of Convergence Route

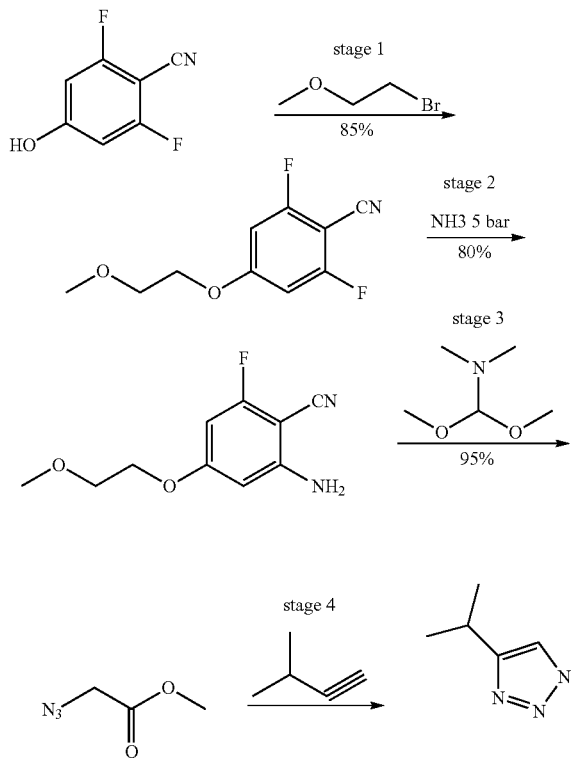

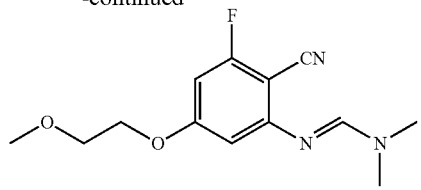

Stage 1:

1-bromo-2-methoxyethane (65.4 mL, 696.31 mmol) was added in one portion to 2,6-difluoro-4-hydroxybenzonitrile (90 g, 580.26 mmol) and potassium carbonate (241 g, 1740.77 mmol) in DMF (1200 mL). The resulting solution was stirred at 85° C. for 5 hours.

The reaction mixture was poured into water (400 mL), extracted with EtOAc (2×200 mL), the organic layer was dried over $Na_2SO_4$, filtered and evaporated to afford crude product.

The crude product was purified by flash silica chromatography, elution gradient 20 to 30% EtOAc in petroleum ether. Pure fractions were evaporated to dryness to afford 2,6-difluoro-4-(2-methoxyethoxy)benzonitrile (115 g, 93%) as a yellow oil. 1H NMR (400 MHz, DMSO-d6) δ 7.17-7.08 (m, 2H), 4.29-4.22 (m, 2H), 3.70-3.61 (m, 2H), 3.30 (s, 3H).

Stage 2:

Aqueous ammonia solution (360 ml, 16.64 mol) was added to 2,6-difluoro-4-(2-methoxyethoxy)benzonitrile (56 g, 0.26 mol) in iPrOH (120 mL) at room temperature. The resulting solution was stirred at 95° C. for 12 hours.

A solid crystallised from solution, the solid was collected by filtration. The solid was washed with 15% isopropanol in water, then washed with water and dried. This resulted in 2-amino-6-fluoro-4-(2-methoxyethoxy)benzonitrile (50.8 g, 92%) as a white solid. 1H NMR (DMSO-d6, 400 MHz) δ 3.29 (3H, s), 3.59-3.66 (2H, m), 4.03-4.10 (2H, m), 6.09-6.23 (2H, m), 6.38 (2H, s).

Stage 3:

DMF-DMA (500 ml, 3734.35 mmol) was added to 2-amino-6-fluoro-4-(2-methoxyethoxy)benzonitrile (90 g, 428.15 mmol). The resulting solution was stirred at 80° C. for 2 hours.

The reaction mixture was poured into ice water (1.5 L), extracted with EtOAc (3×500 mL), the organic layer was dried over $Na_2SO_4$, filtered and evaporated to afford (E)-N'-(2-cyano-3-fluoro-5-(2-methoxyethoxy)phenyl)-N,N-dimethylformimidamide (110 g, 97%) as a colourless solid. 1H NMR (DMSO-d6, 400 MHz) δ 3.04 (6H, d), 3.61-3.69 (2H, m), 4.13-4.21 (2H, m), 6.55-6.63 (2H, m), 8.05 (1H, s).

2nd Arm of Convergence Route

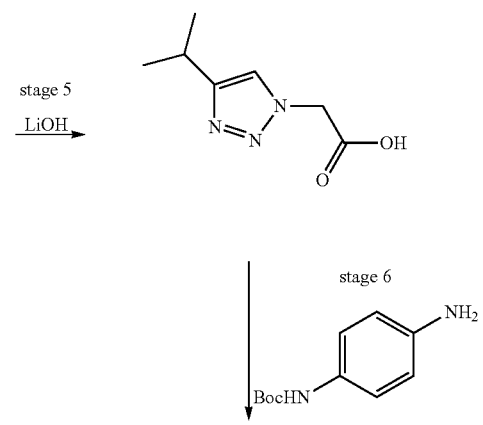

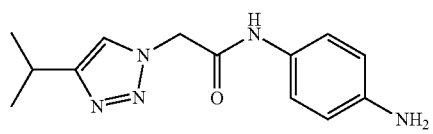 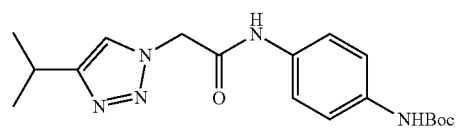

Stage 4:

The process of this stage was run in parallel. A solution of 30% ethyl 2-azidoacetate in DCM (60 g, 464.69 mmol) was mixed with acetonitrile (500 mL) and then added dropwise to a stirred solution of 3-methylbut-1-yne (36.4 g, 534.39 mmol), copper(I) iodide (1.770 g, 9.29 mmol) and TEA (1.295 mL, 9.29 mmol) in acetonitrile (500 mL) at 22° C., over a period of 5 minutes under nitrogen. The resulting solution was stirred at 22° C. for 12 hours.

The resulting solutions were then combined and the solvent was removed under reduced pressure. The crude product was purified by flash silica chromatography, elution gradient 0 to 40% EtOAc in petroleum ether. Pure fractions were evaporated to dryness to afford ethyl 2-(4-isopropyl-1H-1,2,3-triazol-1-yl)acetate (160 g, 175%) as a colourless oil. 1H NMR (Chloroform-d, 300 MHz) δ 1.06-1.18 (9H, m), 2.88-2.97 (1H, m), 4.07 (2H, q), 4.99 (2H, s), 7.35 (1H, d).

Stage 5:

A solution of LiOH (38.9 g, 1622.41 mmol) in water (200 mL) was added dropwise to a stirred solution of ethyl 2-(4-isopropyl-1H-1,2,3-triazol-1-yl)acetate (160 g, 811.20 mmol) in THF (800 mL) at 22° C., over a period of 5 minutes under nitrogen. The resulting solution was stirred at 22° C. for 12 hours.

The solvent was removed under reduced pressure. The reaction mixture was acidified with 2M HCl to pH 6. The solid was collected and dried under vacuum at 40° C. to give 2-(4-isopropyl-1H-1,2,3-triazol-1-yl)acetic acid (120 g, 87%) as a white solid. 1H NMR (Methanol-d4, 300 MHz) δ 1.33 (6H, d), 3.04-3.09 (1H, m), 4.93 (2H, s), 7.69 (1H, d).

Stage 6:

HATU (147 g, 386.88 mmol) was added to tert-butyl (4-aminophenyl)carbamate (67.1 g, 322.40 mmol), 2-(4-isopropyl-1H-1,2,3-triazol-1-yl)acetic acid (60 g, 354.64 mmol) and DIPEA (84 mL, 483.60 mmol) in DMF (200 mL). The resulting solution was stirred at room temperature for 12 hours.

The reaction mixture was poured into water (600 ml). The resulting solid precipitate was collected by filtration and dried to give a light purple solid.

The solid was recrystallised from acetonitrile to afford tert-butyl (4-(2-(4-isopropyl-1H-1,2,3-triazol-1-yl)acetamido)phenyl)carbamate (105 g, 91%) as white solid. 1H NMR (DMSO-d6, 40) MHz) δ 1.25 (6H, d), 1.47 (9H, s), 2.94-3.04 (1H, m), 5.22 (2H, s), 7.36-7.50 (4H, m), 7.85 (1H, d), 9.30 (1H, s), 10.33 (1H, s).

Stage 7:

HCl (4M in dioxane) (598 mL, 2392.68 mmol) was added to tert-butyl (4-(2-(4-isopropyl-1H-1,2,3-triazol-1-yl)acetamido)phenyl)carbamate (86 g, 239.27 mmol) in DCM (400 mL) and MeOH (400 ml). The resulting solution was stirred at 25° C. for 16 hours. The solvent was removed under reduced pressure. The reaction mixture was diluted with DCM. The reaction mixture was adjusted to pH 10 with saturated $Na_2CO_3$. The precipitate was collected by filtration, washed with water (300 mL) and dried under vacuum to afford N-(4-aminophenyl)-2-(4-isopropyl-1H-1,2,3-triazol-1-yl)acetamide (51.0 g, 82%) as a white solid, which was used without further purification. 1H NMR (400 Hz. DMSO) δ: 1.24 (6H, d), 2.96-3.02 (1H, m), 5.11-5.16 (4H, m), 6.53 (2H, d), 7.23 (2H, d), 7.83 (1H, s), 10.04 (1H, s).

Convergence

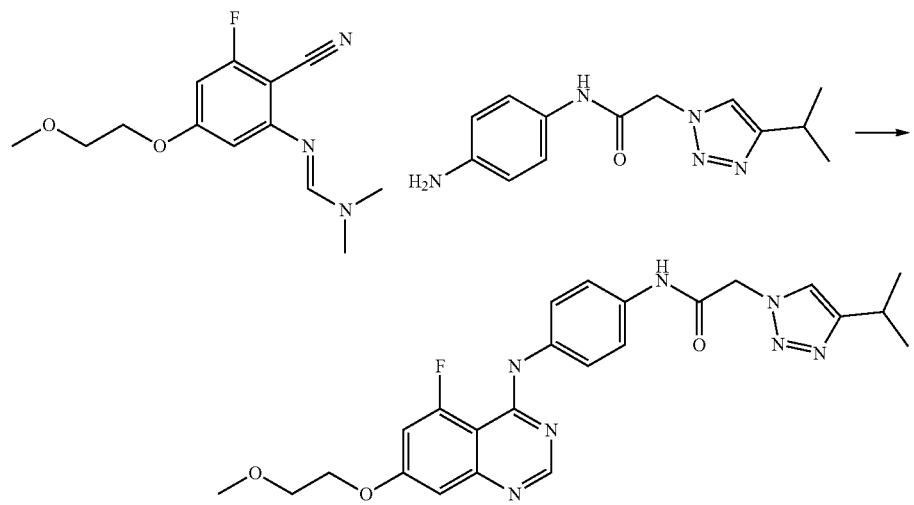

Example 12

(E)-N'-(2-cyano-3-fluoro-5-(2-methoxyethoxy)phenyl)-N,N-dimethylformimidamide (37.6 g, 141.91 mmol) was added to N-(4-aminophenyl)-2-(4-isopropyl-1H-1,2,3-triazol-1-yl)acetamide (46 g, 177.39 mmol) in acetic acid (300 mL). The resulting solution was stirred at 60° C. for 40 minutes.

This reaction was combined with two other batches for isolation and purification which were synthesised according to the process described in the paragraph above.

The reaction mixture was poured into ice water. The precipitate was collected by filtration, washed with water (200 mL) and dried under vacuum to afford crude product.

The crude product was recrystallized with EtOH and dried to afford N-(4-((5-fluoro-7-(2-methoxyethoxy)quinazolin-4-yl)amino)phenyl)-2-(4-isopropyl-1H-1,2,3-triazol-1-yl)acetamide (45.0 g, 66.1%) as white solid. 1H NMR (DMSO-d6, 400 MHz) δ 1.26 (6H, d), 2.93-3.07 (1H, m), 3.33 (3H, s), 3.68-3.75 (2H, m), 4.24-4.32 (2H, m), 5.29 (2H, s), 7.05 (1H, d), 7.14 (1H, q), 7.57-7.64 (2H, m), 7.63-7.72 (2H, m), 7.89 (1H, d), 8.46 (1H, s), 8.98 (1H, d), 10.50 (1H, s).

Example 12A

Scale up of Tosylate Salt of N-(4-{[5-Fluoro-7-(2-methoxyethoxy)quinazolin-4-yl]amino}phenyl)-2-[4-(propan-2-yl)-1H-1,2,3-triazol-1-yl]acetamide

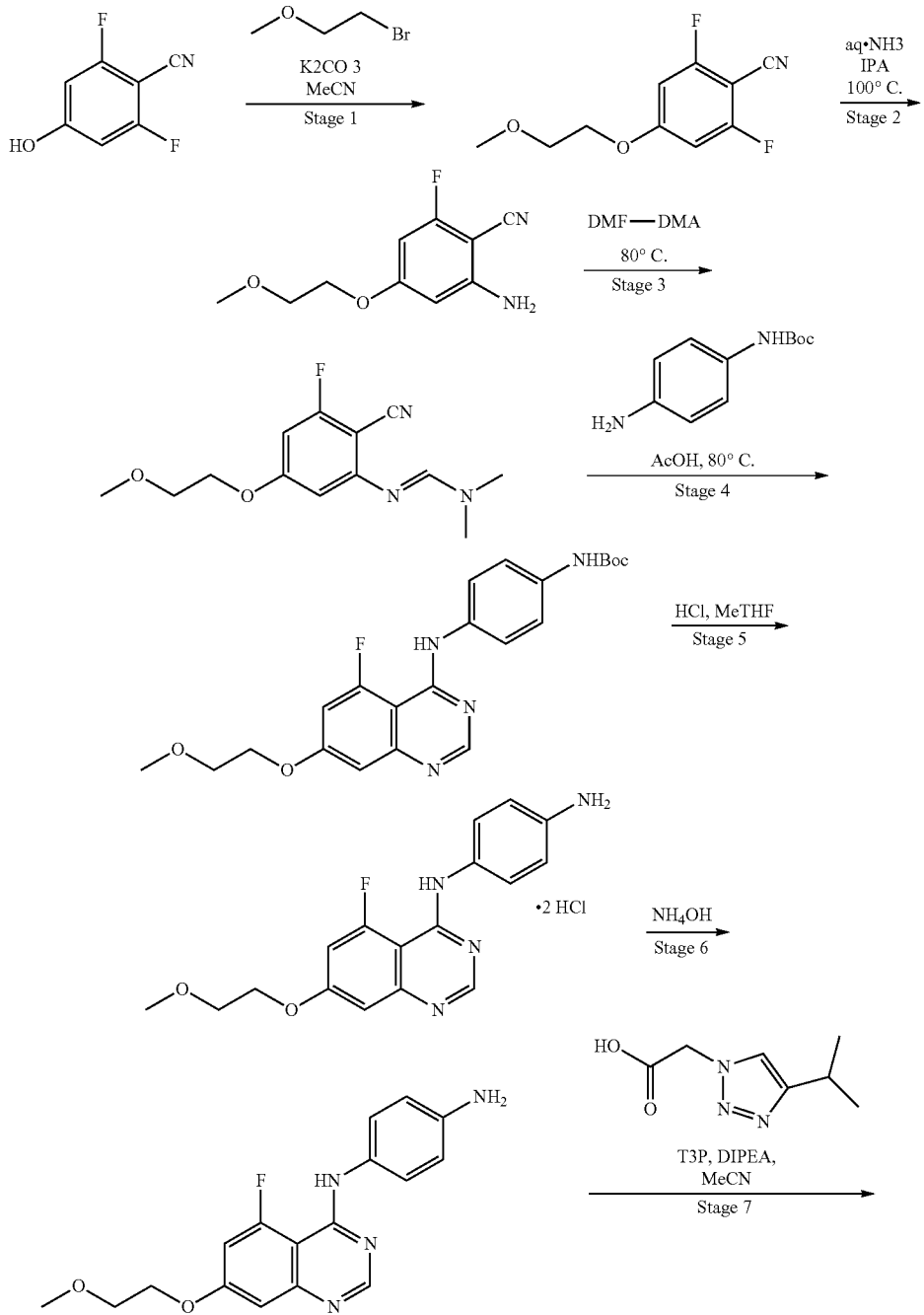

Scheme 4

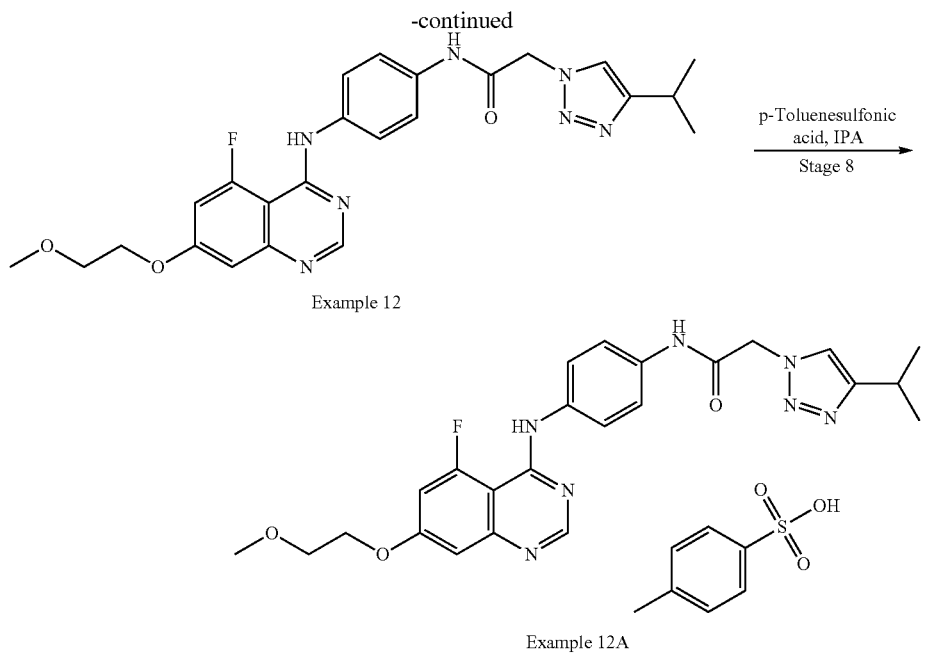

Example 12

Example 12A

Stage 1:

1-bromo-2-methoxyethane (9.6 kg, 69.06 mol) was added in one portion to 2,6-difluoro-4-hydroxybenzonitrile (8.6 kg, 55.45 mol) and potassium carbonate (23 kg, 166.43 mol) in CH$_3$CN (70.9 kg). The resulting solution was stirred at 80-85° C. for 8-10 hours.

The reaction mixture was cooled to 40-45° C. and filtered. The cake was washed with CH$_3$CN (13.4 kg). The combined filtrate was concentrated under vacuum to 34-43 L. Process water (92.0 kg) was added and the mixture was concentrated under vacuum to 77-85 L. The suspension was filtered to afford 2,6-difluoro-4-(2-methoxyethoxy)benzonitrile (13.70 kg, 100%) as a damp solid. 1H NMR (400 MHz, DMSO-d6) δ 3.29 (3H, s), 3.65-3.67 (2H, t), 4.24-4.26 (2H, t), 7.11 (1H, s), 7.14 (1H, s)

Stage 2:

25% Aqueous ammonia solution (187.8 kg, 1341.43 mol) was added to 2,6-difluoro-4-(2-methoxyethoxy)benzonitrile (13.7 kg, 56.68 mol, assay: 88.2%) in iPrOH (42.6 kg) at room temperature. The resulting solution was stirred at 100-110° C. for 16-20 hours in autoclave.

A solid was crystallized from solution and was collected by filtration. The solid was washed with 15% isopropanol in water and dried. This resulted in 2-amino-6-fluoro-4-(2-methoxyethoxy)benzonitrile (7.4 kg, 62%) as a white solid. 1H NMR (DMSO-d6, 400 MHz) δ 3.29 (3H, s), 3.61-3.63 (2H, t), 4.04-4.07 (2H, t), 6.11 (1H, s), 6.16-6.19 (1H, d), 6.37 (2H, s)

Stage 3:

DMF-DMA (16.8 kg, 140.99 mol) was added to 2-amino-6-fluoro-4-(2-methoxyethoxy)benzonitrile (7.4 kg, 35.20 mol) in MTBE (46.8 kg). The resulting solution was stirred at 55-60° C. for 6-8 hours.

The reaction mixture was cooled to 20-30° C. and washed with brine. Molecular sieves (11.0 kg) was added to the organic phase to remove water. The organic solution was concentrated under vacuum to 37-44 L followed by the addition of MTBE to afford (E)-N'-(2-cyano-3-fluoro-5-(2-methoxyethoxy)phenyl)-N,N-dimethylformimidamide solution (53.25 kg, assay: 15.9%, 91%). 1H NMR (DMSO-d6, 400 MHz) δ 2.99 (3H, s), 3.08 (3H, s), 3.30 (3H, s), 3.64-3.67 (2H, t), 4.15-4.18 (2H, t), 6.57-6.60 (2H, m), 8.04 (1H, s)

Stage 4:

tert-butyl (4-aminophenyl)carbamate (8.4 kg, 40.33 mol) was added to (E)-N'-(2-cyano-3-fluoro-5-(2-methoxyethoxy)phenyl)-N,N-dimethylformimidamide solution (9.0 kg, 33.92 mol) in MTBE (30 kg). AcOH (31.6 kg) was added then. The resulting solution was stirred at 50-60° C. for 3-4 hours.

The reaction mixture was cooled to 20-30° C. and filtered. MTBE (26 kg) was used to wash the cake. The solid was dried to afford tert-butyl (4-((5-fluoro-7-(2-methoxyethoxy)quinazolin-4-yl)amino)phenyl)carbamate (13.10 kg, assay: 87.5%, 79%). 1HNMR (DMSO-d6, 400 MHz) δ 1.49 (9H, s), 3.3 (3H, s), 3.70-3.72 (2H, t), 4.27-4.29 (2H, t), 7.04 (1H, s), 7.11-7.15 (1H, dd), 7.43-7.56 (4H, m), 8.42 (1H, s), 8.90-8.93 (1H, d), 9.35 (1H, s)

Stage 5:

HCl gas (85 kg, 2328.77 mol) was added to tert-butyl (4-((5-fluoro-7-(2-methoxyethoxy)quinazolin-4-yl)amino)phenyl)carbamate (10.2 kg, 23.80 mol) in 2-MeTHF (160 kg) and water (10 kg). The resulting solution was stirred at 20-25° C. for 4-6 hours.

The reaction mixture was filtered and washed with 2-MeTHF (40 kg). The solid was dried to afford N1-(5-fluoro-7-(2-methoxyethoxy)quinazolin-4-yl)benzene-1,4-diamine dihydrochloride (9.10 kg, 95%). 1H NMR (DMSO-d6, 400 MHz) δ 3.33 (3H, s), 3.72-3.74 (2H, t), 4.30-4.35 (2H, t), 7.29-7.62 (6H, m), 8.79 (1H, s), 10.57 (2H, brs)

Stage 6:

25% Aqueous ammonia solution (27 kg, 192.86 mol) was added to N1-(5-fluoro-7-(2-methoxyethoxy)quinazolin-4-yl)benzene-1,4-diamine dihydrochloride (9.10 kg, 22.68 mol) in water (150 kg). The resulting solution was stirred at 20-25° C. for 2-3 hours.

The reaction mixture was filtered and washed with water (60 kg). The solid was dried to afford N1-(5-fluoro-7-(2-methoxyethoxy)quinazolin-4-yl)benzene-1,4-diamine (6.15 kg, 83%). 1HNMR (DMSO-d6, 400 MHz) δ 3.3 (3H, s), 3.70-3.72 (2H, t), 4.25-4.29 (2H, t), 5.07 (2H, s), 6.56-6.59 (2H, d), 7.00 (1H, s), 7.09-7.10 (1H, d), 7.23-7.25 (2H, d), 8.35 (1H, s), 8.69-8.72 (1H, d)

Stage 7:

N-[5-fluoro-7-(2-methoxyethoxy)-4-quinazolinyl]-1,4-benzenediamine (4.184 kg, 12.5 mol) was charged with [4-(propan-2-yl)-1H-1,2,3-triazol-1-yl]acetic acid (2.41 kg, 13.8 mol) and acetonitrile (62 L) and heated to 65° C. N-ethyldiisopropylamine (4.36 L, 25.0 mol) was charged with 1-propanephosphonic anhydride 50% in acetonitrile (9.96 kg, 16.3 mol) at <80° C. The mixture was stirred at 65° C. and then cooled to 10-20° C. and 2-propanol (20.5 L) was added. The mixture was then cooled to 0-10° C. before filtering, washing with acetonitrile (2×10 L) and then drying to afford N-(4-{[5-Fluoro-7-(2-methoxyethoxy)quinazolin-4-yl]amino}phenyl)-2-[4-(propan-2-yl)-1H-1,2,3-triazol-1-yl]acetamide (5.530 kg, 91.1%) as an off white solid. 1H NMR (500 MHz, DMSO-d6) δ1.2 (d, 6H) 3.0 (spt, 1H) 3.3 (s, 3H) 3.7-3.7 (m, 2H) 4.2-4.3 (m, 2H) 5.3 (s, 2H) 7.0 (d, 1H) 7.1 (dd, 1H) 7.5-7.6 (m, 2H) 7.6-7.7 (m, 2H) 7.9 (s, 1H) 8.4 (s, 1H) 9.0 (d, 1H) 10.5 (s, 1H)

Stage 8:

N-(4-{[5-Fluoro-7-(2-methoxyethoxy)quinazolin-4-yl]amino}phenyl)-2-[4-(propan-2-yl)-1H-1,2,3-triazol-1-yl]acetamide (2 kg, 4.13 mol) and p-toluenesulfonic acid (0.842 kg, 4.34 mol) are heated with agitation in a mixture of propan-2-ol (26 L, 340 mol) and dimethylsulfoxide (6.5 L, 92 mol) until a solution is formed. The resulting solution is filtered hot and the filtrate cooled and seeded with N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate, the seed was prepared according to the method described below under the heading "Form A of Tosylate Salt Y". The resulting N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate is filtered under reduced pressure and the filter cake washed with a mixture of propan-2-ol (0.4 L, 5 mol) and dimethylsulfoxide (0.1 L, 1 mol). After deliquoring of the filter cake and final filter cake washing with propan-2-ol the solids are dried in the vacuum oven to provide N-(4-{[5-Fluoro-7-(2-methoxyethoxyethoxy)quinazolin-4-yl]amino}phenyl)-2-[4-(propan-2-yl)-1H-1,2,3-triazol-1-yl]acetamide tosylate (2.458 kg, 91.2%) as a bright yellow solid. 1H NMR (500 MHz, DMSO-d6) δ1.2 (d, 6H) 2.3 (s, 3H) 3.0 (spt, 1H) 3.3 (s, 3H) 3.7-3.8 (m, 2H) 4.3-4.4 (m, 2H) 5.3 (s, 2H) 7.0-7.1 (m, 3H) 7.4-7.6 (m, 5H) 7.6-7.7 (m, 2H) 7.9 (s, 1H) 8.8 (s, 1H) 10.5 (br d, 1H) 10.6 (s, 1H)

Scheme 5:

The [4-(propan-2-yl)-1H-1,2,3-triazol-1-yl]acetic acid used in Stage 7 of Scheme 4 was prepared by the method depicted in Scheme 5. A solution of methyl 2-bromoacetate (5.4 kg, 36 mol) in 2-propanol (19 L) and sodium azide (2.3 kg, 35 mol) in water (23 L) were reacted in an Alfa Laval flow reactor at 120° C. with a residence time of 40 seconds, the reaction was monitored by PAT (IR and RAMAN). The output feed was then further reacted with a solution feed containing 3-methylbut-1-yne (3.1 kg, 44 mol) with copper iodide (0.21 kg) and trimethylamine (1.1 kg) in pyridine (8.1 L) at 80° C. with residence time of 152 seconds. The output (monitored by PAT IR) is collected in in an agitated vessel along with a solution feed containing di-sodium edetate (2.9 kg), sodium nitrite (0.14 kg) and sodium hydroxide (5 kg, 58 mol) in water (7.95 L). The resulting suspension is filtered under reduced pressure. Tert-butyl methyl ether (45 L) is added to the filtrate and the mixture agitated for 30 minutes. The agitation is stopped and the layers allowed to separate and the aqueous layer collected. The aqueous layer is acidified by slow addition of aqueous sulfuric acid (3.5 M) with agitation maintaining the temperature at <26° C. until a pH of 2.5 is achieved. 2-Methyltetrahydrofuran (32.5 L) is then added and the mixture agitated for a further 10 minutes. The agitation is stopped and the layers allowed to separate. The organic layer is collected. 2-Methyltetrahydrofuran (33 L) is added to the resulting aqueous layer and the mixture agitated for 10 minutes. The agitation is stopped and the layers allowed to separate and the organic layer collected. The resulting aqueous layer is adjusted to a pH of 2.5 with 3.5 M HCl with agitation and 2-methyltetrahydrofuran (16 L) added and the mixture agitated for 10 minutes. The agitation is stopped and the layers allowed to separate. The organic layer is collected and combined with the previously collected 2-methyltetrahydrofuran organic extracts. The combined organic extracts are distilled at atmospheric pressure to remove 15 relative volumes (48.6 L) of organics. Further 2-methyltetrahydrofuran (33 L) is added to the remaining organics and the mixture distilled at atmospheric pressure to remove a further 12 relative volumes (40 L) of organics. The remaining organics are cooled to 70° C. with agitation then ramp cooled to 0° C. over the course of 4 hours. Tert-butyl methyl ether (13 L) is added over 20 minutes and the mixture agitated at 0° C. for 3 hours. The resulting suspension is filtered under reduced pressure. The filter cake is washed with pre-cooled (0° C.) tert-butyl Scheme 5

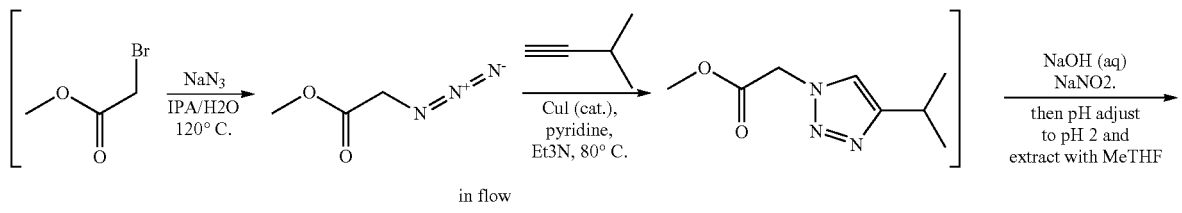

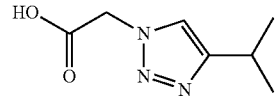

Product isolated
by distillation and cooling
crystallisation in 80% yield
(3 kg).

methyl ether (13 L) and the filter cake pulled dry. The resulting solids are dried in the vacuum oven (40° C.) to provide [4-(propan-2-yl)-1H-1,2,3-triazol-1-yl]acetic acid as a white crystalline solid (6.2 kg, 40%). 1H NMR (DSMO-d6, 500 MHz): 13.3 (1H, br s, OH) 7.82 (1H, s, 5-H), 5.21 (2H, s, CH$_2$CO$_2$H), 2.99 (1H, hept, J=5 Hz, CHMe$_2$), 1.24 (6H, d, J=5 Hz, 2×Me). 13C NMR (DMSO-d6, 125 MHz): 168.9 (C=O), 153.1 (C, C-4), 121.9 (CH, C-5), 50.45 (CH$_2$, CH$_2$CO$_2$H), 23.32 (CH, CHMe$_2$), 22.51 (CH$_3$, 2×Me). UPLC MS (BEH/MeCN/TFA): Rt=0.61 min (λ max=221.1). Mass spectrum: 170.06 (M+H), 154.05 (M−CH$_3$), 125.9 (M−CO$_2$), 112.0 (M−CH$_2$CO$_2$H).

Form A of Tosylate Salt Y

N-(4-{[5-Fluoro-7-(2-methoxyethoxy)quinazolin-4-yl]amino}phenyl)-2-[4-(propan-2-yl)-1H-1,2,3-triazol-1-yl]acetamide pure free base and p-toluenesulfonic acid monohydrate were dissolved in 16 relative volumes of 20% dimethylsulfoxide:propan-2-ol at 20° C. Seed of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form A (0.02%) was added to the vessel and the contents of the vessel were heated to 75° C. over a minimum of 60 minutes. The resulting solution was screened into a crystalliser at 75° C. via an inline filter. Resulting solution was cooled to 40° C. over 20 minutes and propan-2-ol (6.5 relative volumes) was added dropwise to the reaction vessel as an antisolvent to bring the solvent composition to 15% dimethylsulfoxide:propan-2-ol. The crystalliser was seeded again with N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form A (0.06%) while the slurry was at 40° C. The slurry was kept stirring at 40° C. for 3 days. XRPD analysis was carried out to check for polymorphic form. The resultant slurry was filtered, washed with 15% dimethylsulfoxide:propan-2-ol and the solid was dried in the vacuum oven at 40° C. until constant weight was obtained. The resulting powder was sampled for XRPD and HPLC for polymorphic form and purity check respectively, and the loss to liquors was also determined.

In certain circumstances, an additional step may be required, which involves suspending the material in isopropyl acetate, seeding with N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form A and slurrying at 80° C. for 24 hours. The resulting material is analysed by XRPD to confirm formation of Form A, isolated and dried as described above. Form A is characterised by at least one peak at 2θ value of 13.4° and 14.3°, measured using CuKα radiation. The ten most prominent peaks of the XRPD are shown in Table C.

Seed of N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate Salt Form A The seed used in the method described above for Form A of Tosylate Salt Y was obtained as follows: N-(4-{[5-Fluoro-7-(2-methoxyethoxy)quinazolin-4-yl]amino}phenyl)-2-[4-(propan-2-yl)-1H-1,2,3-triazol-1-yl]acetamide pure free base was added to a Duran bottle and 20 relative volumes of ethyl acetate were added to the bottle while stirring to create a slurry. A solution of p-toluenesulfonic acid monohydrate (1.1 equivalent) was made by fully dissolving it in 40 relative volumes of ethyl acetate. The p-toluenesulfonic acid solution was added dropwise to the API solution while stirring vigorously. The resulting yellow material was subjected to slurrying under ambient conditions for 5 days in the capped Duran bottle. The resulting material was checked by XRPD to show the formation of a highly crystalline material that corresponded to a 1:1 N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt following analysis by NMR, DSC and X-ray crystal structure elucidation. The solid was isolated by vacuum filtration and dried in a vacuum oven.

TABLE C

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form A

| Angle 2-Theta (2θ) | Intensity % |
|---|---|
| 11.7 | 100 |
| 20.2 | 74.6 |
| 12.2 | 51.4 |
| 21.4 | 36.6 |
| 23.6 | 30.1 |
| 23.7 | 29.4 |
| 24.4 | 25.9 |
| 17.3 | 22.3 |
| 14.3 | 11.1 |
| 13.4 | 9.7 | wherein the 2-theta values are +/−0.2°.

Form B of Tosylate Salt Y

Form B of Tosylate Salt Y is a hydrated form obtained from salt scale-up experiments in ethanol, seeded with Form C of Tosylate Salt Y.

Form B was obtained by exposing Form C of Tosylate Salt Y to high humidity levels such as in a DVS experiment. Alternatively, Form B was obtained during a salt scale-up experiment in ethanol. N-(4-{[5-Fluoro-7-(2-methoxyethoxy)quinazolin-4-yl]amino}phenyl)-2-[4-(propan-2-yl)-1H-1,2,3-triazol-1-yl]acetamide pure free base and p-toluenesulfonic acid monohydrate were added in a 1 liter glass reactor equipped with an overhead stirrer. Ten relative volumes of ethanol were added to the reactor at 20° C. The contents of the vessel were heated to 75° C. over 2 hours to obtain a clear yellow solution. The contents of the reactor were cooled to 60° C. over 20 minutes. 1% of the mixture of Forms C and B, obtained from the Form C method outlined in the section below, was added to the reactor while stirring. Contents were held at 60° C. for 5 hours followed by cooling to 5° C. over 10 hours. The solid was isolated at 5° C. by vacuum filtration, washed with chilled ethanol and dried in a vacuum oven at 20° C. overnight, followed by a 25 minute drying period at 40° C. The resulting solid was analysed by XRPD and gave a crystalline form named Form B. Form B is characterised by at least one peak at 2θ value of 4.2° and 7.7°, measured using CuKα radiation. The ten most prominent peaks of the XRPD are shown in Table D.

TABLE D

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form B

| Angle 2-Theta (2θ) | Intensity % |
|---|---|
| 11.8 | 100 |
| 19.4 | 88.2 |
| 25.2 | 84.2 |

TABLE D-continued

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form B

| Angle 2-Theta (2θ) | Intensity % |
|---|---|
| 7.1 | 61.7 |
| 20.9 | 61 |
| 14.2 | 54 |
| 20.4 | 43.2 |
| 23.9 | 37.2 |
| 22.5 | 32.8 |
| 9.2 | 11 | wherein the 2-theta values are +/−0.2°.

Form C of Tosylate Salt Y

Form C of Tosylate Salt Y is an ethanol solvate form obtained from solubility measurement experiments in ethanol and acetonitrile.

Form C was obtained during solubility measurement experiments starting with Form A of Tosylate Salt Y. Solubility curves were generated in ethanol and acetonitrile. Different masses of Form A were added in vials and stirred in ethanol and acetonitrile. The heating ramp was set from 25° C. to 75° C. at a rate of 0.03° C./minute. All materials went into solution at elevated temperatures. The solutions were cooled back to 25° C. at a rate of 0.03° C./minute and solid was recrystallised in the vials at different points of the cooling cycle. The resulting solids were analysed by XRPD as slurries and gave a crystalline form named Form C. Form C is not a stable form and will convert to Form B both during vacuum drying and under ambient conditions. Therefore, it is common to isolate a mixture of Forms C and B that will eventually convert to Form B through evaporation of ethanol from the crystal structure. The isolated mixture of Forms C and B can be used as a seed in the method for obtaining Form B, described in the section above.

Form D of Tosylate Salt Y

Form D of Tosylate Salt Y is a dimethylsulfoxide solvate form obtained from salt scale-up experiments in 20% dimethylsulfoxide:propan-2-ol.

Form D was obtained by crystallisation from a N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt saturated solution in 20% dimethylsulfoxide:propan-2-ol. Initially, the solvent system used for obtaining Form A was 20% dimethylsulfoxide:propan-2-ol. It was later realised that recrystallization from the mother liquor after initial Form A isolation in the above solvent system yielded Form D. The amount of dimethylsulfoxide in the solvent mixture for obtaining Form A was therefore reduced from 20% to 15% to ensure that Form A is obtained. Form A is obtained at a temperature of 40° C. while Form D is obtained at temperatures below 25° C. Form D is characterised by at least one peak at 2θ value of 4.4° and 5.6°, measured using CuKα radiation. The ten most prominent peaks of the XRPD are shown in Table E.

TABLE E

Ten most prominent XRPD peaks for N-(4-{[5-Fluoro-7-(2-methoxyethoxy)quinazolin-4-yl]amino}phenyl)-2-[4-(propan-2-yl)-1H-1,2,3-triazol-1-yl]acetamide tosylate salt Form D

| Angle 2-Theta (2θ) | Intensity % |
|---|---|
| 4.4 | 100 |
| 8.8 | 96.2 |
| 19.1 | 53.8 |
| 24.8 | 23.7 |
| 16.8 | 18.3 |
| 26.9 | 17.4 |
| 22.3 | 15.9 |
| 5.6 | 15.6 |
| 21.9 | 14.5 |
| 19.7 | 14.4 | wherein the 2-theta values are +/−0.2°.

Example 13 and Example 14

(R)-2-(4-Isopropyl-1H-1,2,3-triazol-1-yl)-N-(4-((5-methoxy-7-((tetrahydrofuran-3-yl)oxy)quinazolin-4-yl)amino)phenyl)acetamide and (S)-2-(4-isopropyl-1H-1,2,3-triazol-1-yl)-N-(4-((5-methoxy-7-((tetrahydrofuran-3-yl)oxy)quinazolin-4-yl)amino)phenyl)acetamide

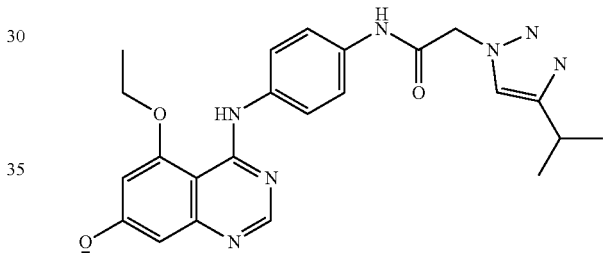

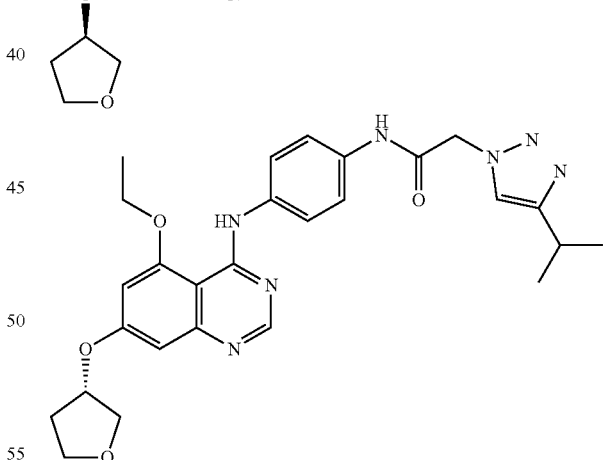

Potassium tert-butoxide (150 mg, 1.4 mmol) was added to tetrahydrofuran-3-ol (121 mg, 1.4 mmol) and N-(4-((7-fluoro-5-methoxyquinazolin-4-yl)amino)phenyl)-2-(4-isopropyl-1H-1,2,3-triazol-1-yl)acetamide (300 mg, 0.7 mmol) in DMF (3 mL) at 25° C. under nitrogen. The resulting mixture was stirred at 80° C. for 5 hours. The reaction mixture was cooled to room temperature and filtered to give a crude residue. The residue was purified by flash silica chromatography, elution gradient 0 to 10% methanol in DCM. Pure fractions were evaporated to dryness to afford crude product as a yellow solid. The crude product was purified by preparative HPLC. Fractions containing the desired compound were evaporated to dryness to afford racemic title compound as a pale yellow solid (150 mg, 43%). The racemic product was purified by preparative chiral-HPLC on a Chiralpak IB column, eluting isocratically with 30% isopropanol in TBME (modified with 0.1% DEA) as eluent. The fractions containing the desired compound were evaporated to dryness to afford one enantiomer of 2-(4-isopropyl-1H-1,2,3-triazol-1-yl)-N-(4-((5-methoxy-7-((tetrahydrofuran-3-yl)oxy)quinazolin-4-yl)amino)phenyl) acetamide as a pale yellow solid (52 mg, 15%, >99.9% e.e.). 1H NMR (300 MHz, DMSO-d6) δ 1.25 (6H, d), 1.97-2.11 (1H, m), 2.27-2.41 (1H, m), 2.94-3.06 (1H, m), 3.75-4.00 (4H, m), 4.11 (3H, s), 5.22-5.28 (1H, m), 5.29 (2H, s), 6.80-6.84 (2H, m), 7.61 (2H, d), 7.67 (2H, d), 7.88 (1H, s), 8.62 (1H, s), 10.43 (1H, s), 10.65 (1H, s); m % z (ES+), [M+H]+=504; acid, HPLC tR=1.35 min. This was followed by the other enantiomer of 2-(4-isopropyl-1H-1,2,3-triazol-1-yl)-N-(4-((5-methoxy-7-((tetrahydrofuran-3-yl)oxy)quinazolin-4-yl)amino)phenyl)acetamide as a pale yellow solid (51 mg, 15%, 98.7% e.e.). 1H NMR (300 MHz, DMSO-d6) δ 1.25 (6H, d), 1.96-2.10 (1H, m), 2.25-2.39 (1H, m), 2.94-3.06 (1H, m), 3.74-3.98 (4H, m), 4.08 (3H, s), 5.20-5.26 (1H, m), 5.27 (2H, s), 6.67 (1H, d), 6.75 (1H, d), 7.60 (2H, d), 7.77 (2H, d), 7.88 (1H, s), 8.41 (1H, s), 9.80 (1H, s), 10.49 (1H, s); m/z (ES+), [M+H]+=504; acid, HPLC tR=1.35 min.

Example 15

N-(4-{[5-Methoxy-7-(propan-2-yloxy)quinazolin-4-yl]amino}phenyl)-2-[4-(propan-2-yl)-1H-1,2,3-triazol-1-yl]acetamide

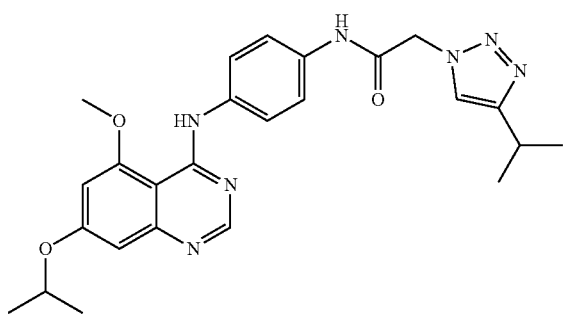 [SMILES: COc1cc(OC(C)C)cc2ncnc(Nc3ccc(NC(=O)Cn4cc(C(C)C)nn4)cc3)c12]

Sodium hydride (41 mg, 1 mmol) was added to N-(4-((7-fluoro-5-methoxyquinazolin-4-yl)amino)phenyl)-2-(4-isopropyl-1H-1,2,3-triazol-1-yl)acetamide (150 mg, 0.3 mmol) and isopropanol (62.1 mg, 1 mmol) in DMF (1.5 mL) at 25° C. under nitrogen. The resulting solution was stirred at room temperature for 1 hour. The resulting solution was stirred at 80° C. for 7 hours. The reaction mixture was filtered. The crude product was purified by preparative HPLC. Fractions containing the desired compound were evaporated to dryness to afford the title compound as a white solid (72 mg, 44%). 1H NMR (300 MHz, DMSO-d6) δ 1.26 (6H, d), 1.35 (6H, d), 2.94-3.07 (1H, m), 4.08 (3H, s), 4.77-4.90 (1H, m), 5.27 (2H, s), 6.64 (1H, d), 6.77 (1H, d), 7.60 (2H, d), 7.78 (2H, d), 7.88 (1H, s), 8.40 (1H, s), 9.77 (1H, s), 10.49 (1H, s) m/z (ES+), [M+H]+=476; acid. HPLC tR=6.90 min.

Example 16

N-(4-{[5-Methoxy-7-(oxetan-3-yloxy)quinazolin-4-yl]amino}phenyl)-2-[4-(propan-2-yl)-1H-1,2,3-triazol-1-yl]acetamide

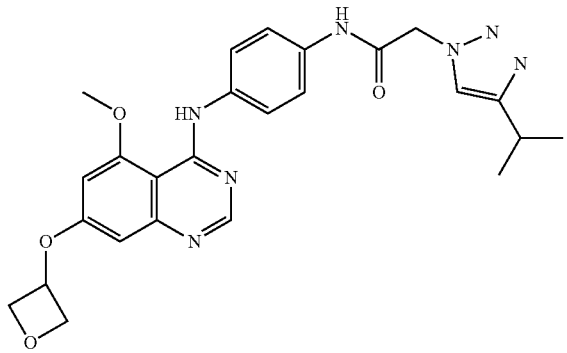 [SMILES: COc1cc(OC2COC2)cc2ncnc(Nc3ccc(NC(=O)CN(N)/C=C(\N)C(C)C)cc3)c12]

Potassium tert-butoxide (52 mg, 0.5 mmol) was added to oxetan-3-ol (34 mg, 0.5 mmol) and N-(4-((7-fluoro-5-methoxyquinazolin-4-yl)amino)phenyl)-2-(4-isopropyl-1H-1,2,3-triazol-1-yl)acetamide (100 mg, 0.2 mmol) in DMF (0.5 mL) at 25° C. under air. The resulting mixture was stirred at 80° C. for 5 hours. The crude product was purified by preparative HPLC. Fractions containing the desired compound were evaporated to dryness to afford the title compound (42 mg, 37%) as an off-white solid. 1H NMR (300 MHz, DMSO, 23° C.) δ 1.25 (6H, d), 2.94-3.06 (1H, m), 4.10 (3H, s), 4.59 (2H, t), 5.00 (2H, t), 5.26 (2H, s), 5.42-5.50 (1H, m), 6.45 (1H, s), 6.72 (1H, s), 7.58-7.60 (2H, m), 7.75-7.77 (2H, m), 7.87 (1H, s), 8.40 (1H, s), 9.78 (1H, s), 10.48 (1H, s). m/z (ES+), [M+H]+=490; TFA, HPLC tR=2.319 min.

Example 17

N-[4-({7-[2-(Dimethylamino)ethoxy]-5-methoxyquinazolin-4-yl}amino)phenyl]-2-[4-(propan-2-yl)-1H-1,2,3-triazol-1-yl]acetamide

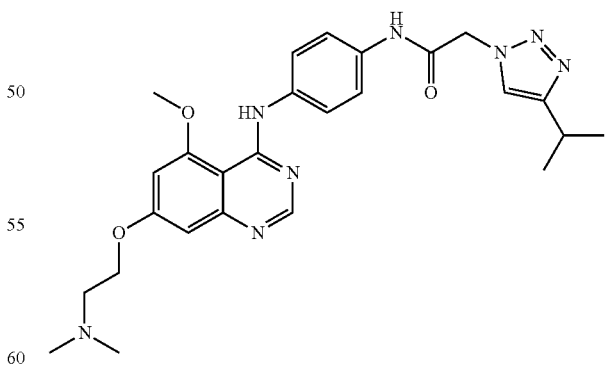

Potassium tert-butoxide (52 mg, 0.5 mmol) was added to N-(4-((7-fluoro-5-methoxyquinazolin-4-yl)amino)phenyl)-2-(4-isopropyl-1H-1,2,3-triazol-1-yl)acetamide (100 mg, 0.2 mmol) and 2-(dimethylamino)ethan-1-ol (31 mg, 0.3 mmol) in DMF (1 mL) at 25° C. under nitrogen. The resulting solution was stirred at 100° C. for 3 hours. The reaction mixture was purified by flash silica chromatography, elution gradient 0 to 10% methanol (1M NH$_3$) in DCM. Pure fractions were evaporated to dryness to afford crude product as a yellow solid. The crude product was purified by preparative HPLC. Fractions containing the desired compound were evaporated to dryness to afford the title compound as a white solid (36 mg, 31%). 1H NMR (300 MHz, DMSO-d6) δ 1.25 (6H, d), 2.24 (6H, s), 2.67 (2H, t), 2.92-3.06 (1H, m), 4.08 (3H, s), 4.19 (2H, t), 5.27 (2H, s), 6.68 (1H, d), 6.79 (1H, d), 7.59 (2H, d), 7.78 (2H, d), 7.88 (1H, d), 8.40 (1H, s), 9.78 (1H, s), 10.48 (1H, s); m/z (ES+), [M+H]+=505; acid, HPLC tR=1.12 min.

Example 18

N-{4-[(7-Ethoxy-5-methoxyquinazolin-4-yl)amino]phenyl}-2-[4-(propan-2-yl)-1H-1,2,3-triazol-1-yl]acetamide

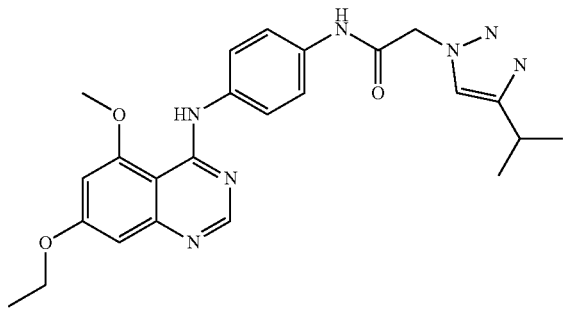 [SMILES: CCOc1cc(OC)c2c(Nc3ccc(NC(=O)CN(N)/C=C(\N)C(C)C)cc3)ncnc2c1]

Sodium ethoxide (in ethanol) (66 mg, 1 mmol) was added to N-(4-((7-fluoro-5-methoxyquinazolin-4-yl)amino)phenyl)-2-(4-isopropyl-1H-1,2,3-triazol-1-yl)acetamide (85 mg, 0.2 mmol) in DMF (5 mL) at room temperature. The resulting solution was stirred at 80° C. for 3 hours. The reaction mixture was poured into saturated aqueous NH$_4$Cl (100 mL). The mixture was filtered and the crude product was purified by preparative HPLC. Fractions containing the desired compound were evaporated to dryness to afford the title compound as a light yellow solid (30 mg, 33%). 1H NMR (DMSO-d6, 400 MHz) δ 1.26 (6H, d), 1.40 (3H, t), 2.93-3.08 (1H, m), 4.08 (3H, s), 4.18 (2H, d), 5.27 (2H, s), 6.73 (2H, dd), 7.60 (2H, d), 7.78 (2H, d), 7.88 (1H, s), 8.41 (1H, s), 9.78 (1H, s), 10.49 (1H, s); m/z (ES+), [M+H]+=462; acid. HPLC tR=1.406 min.

Example 19

N-{4-[(5,7-Diethoxyquinazolin-4-yl)amino]phenyl}-2-[4-(propan-2-yl)-1H-1,2,3-triazol-1-yl]acetamide

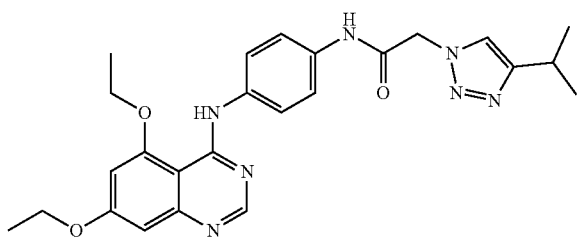 [SMILES: CCOc1cc(OCC)c2c(Nc3ccc(NC(=O)Cn4cc(C(C)C)nn4)cc3)ncnc2c1]

HATU (140 mg, 0.4 mmol) was added to 4-((5,7-diethoxyqunazoinazolin-4-yl)oxy)aniline (260 mg, 0.3 mmol), 2-(4-isopropyl-1H-1,2,3-triazol-1-yl)acetic acid (79 mg, 0.3 mmol) and DIPEA (0.12 mL, 0.7 mmol) in DMF (3 mL) at 23° C. under nitrogen. The resulting solution was stirred at room temperature for 1 hour. The solvent was removed under reduced pressure. The crude product was purified by flash silica chromatography, elution gradient 0 to 8% methanol in DCM. Pure fractions were evaporated to dryness to afford crude product as a yellow solid. The crude product was purified by preparative HPLC. Fractions containing the desired compound were evaporated to dryness to afford the title compound as a white solid (97 mg, 61%). 1H NMR (400 MHz, DMSO-d6) δ 1.25 (6H, d), 1.39 (3H, t), 1.57 (3H, t), 2.95-3.06 (1H, m), 4.11-4.24 (2H, m), 4.26-4.40 (2H, m), 5.27 (2H, s), 6.68 (1H, d), 6.76 (1H, d), 7.61 (2H, d), 7.79 (2H, d), 7.88 (1H, s), 8.44 (1H, s), 9.97 (1H, s), 10.51 (1H, s); m/z (ES+), [M+H]+=476; acid. HPLC tR=1.48 min.

The intermediates used in Example 19 were prepared as follows:

Preparation of 5,7-Diethoxyquinazolin-4(3H)-one

Sodium ethoxide (2.6 g, 7.9 mmol) was added to 7-fluoro-5-methoxyquinazolin-4(3H)-one (1.4 g, 7.2 mmol) in DMF (15 mL) under nitrogen. The resulting solution was stirred at 80° C. for 5 hours. The reaction mixture was poured into ice water. The resulting precipitate was collected by filtration, washed with cold water (100 mL), ether (50 ml) and dried under vacuum to afford a solid. The crude product was purified by preparative HPLC. Fractions containing the desired compound were evaporated to dryness to afford firstly 7-ethoxy-5-methoxyquinazolin-4(3H)-one (0.5 g, 29%). 1H NMR (DMSO-d6, 300 MHz) δ 1.38 (3H, t), 3.83 (3H, s), 4.16 (2H, q), 6.53 (1H, d), 6.65 (1H, d), 7.92 (1H, s), 11.78 (1H, s) followed by 5,7-diethoxyquinazolin-4(3H)-one as a white solid (0.2 g, 9%). 1H NMR (DMSO-d6, 300 MHz) δ 1.35 (6H, t), 4.10 (4H, dq), 6.49 (1H, d), 6.61 (1H, d), 7.88 (1H, s), 11.71 (1H, s).

Preparation of N1-(5,7-Diethoxyquinazolin-4-yl)benzene-1,4-diamine

DBU (0.27 mL, 1.8 mmol) was added to 5,7-diethoxyquinazolin-4(3H)-one (160 mg, 0.7 mmol) and BOP (393 mg, 0.9 mmol) in acetonitrile (5 mL) at room temperature under nitrogen. The resulting solution was stirred at 60° C. for 1 hour. Para-Phenylenediamine (148 mg, 1.4 mmol) was added. The resulting solution was stirred at 60° C. for 5 hours. The reaction mixture was concentrated and diluted with DCM (100 mL), and washed sequentially with saturated aqueous NH$_4$Cl (10 mL), water (10 mL), and saturated NaHCO$_3$ (10 mL). The organic layer was dried, filtered and evaporated to afford crude product. The crude product was purified by flash silica chromatography, elution gradient 0 to 4% methanol in DCM. Pure fractions were evaporated to dryness to afford the title compound as a yellow solid (280 mg, >100%). 1H NMR (400 MHz, DMSO-d6) δ 1.38 (3H, t), 1.54 (3H, t), 4.12-4.18 (2H, m), 4.24-4.37 (2H, m), 5.60 (2H, s), 6.58 (1H, s), 6.61 (2H, d), 6.70 (1H, s), 7.39 (2H, d), 8.33 (1H, s), 9.68 (1H, s); m/z (ES+), [M+H]+=325; base, HPLC tR=0.83 min.

Example 20

N-(4-{[5-Methoxy-7-(2-methoxyethoxy)quinazolin-4-yl]amino}phenyl)-2-[4-(propan-2-yl)-1H-1,2,3-triazol-1-yl]acetamide

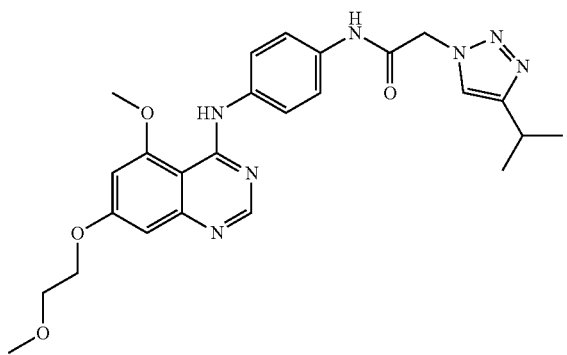 [SMILES: COCCOc1cc(OC)c2c(Nc3ccc(NC(=O)Cn4cc(C(C)C)nn4)cc3)ncnc2c1]

HATU (10 mg, 0.03 mmol) was added to N1-(5-methoxy-7-(2-methoxyethoxy)quinazolin-4-yl)benzene-1,4-diamine (1.5 g, 4.4 mmol), 2-(4-isopropyl-1H-1,2,3-triazol-1-yl)acetic acid (1.1 g, 4.9 mmol) and DIPEA (1.1 g, 8.8 mmol) in DMF (30 mL). The resulting mixture was stirred at room temperature for 2 hours. The reaction mixture was diluted with water. The resulting precipitate was collected by filtration, washed with acetonitrile/H$_2$O (1:10, 50 mL) and dried under vacuum. The crude product was purified by crystallisation from acetonitrile to afford the title compound as a pale yellow solid (1.5 g, 70%). 1H NMR (400 MHz, DMSO-d6) δ 1.25 (6H, d), 2.93-3.07 (1H, m), 3.33 (3H, s), 3.65-3.77 (2H, m), 4.09 (3H, s), 4.20-4.30 (2H, m), 5.26 (2H, s), 6.72 (1H, d), 6.78 (1H, d), 7.59 (2H, d), 7.77 (2H, d), 7.87 (1H, s), 8.41 (1H, s), 9.79 (1H, s), 10.48 (1H, s); m/z (ES+), [M+H]+=492; acid, HPLC tR=1.44 min.

The intermediates used in Example 20 were prepared as follows:

Preparation of 5-Methoxy-7-(2-methoxyethoxy)quinazolin-4(3H)-one

Potassium tert-butoxide (4.3 g, 38.6 mmol) was added to 7-fluoro-5-methoxyquinazolin-4(3H)-one (3 g, 15.5 mmol) and 2-methoxyethan-1-ol (1.76 g, 23.2 mmol) in DMSO (30 mL) under nitrogen. The resulting solution was stirred at 80° C. for 15 hours. The reaction mixture was neutralised with 2M HCl. The combined aqueous layer was dried by lyophilization. The reaction mixture was diluted with DCM (30 mL) and TBME (70 mL). The resulting precipitate was collected by filtration, washed with DCM (10 mL) and dried under vacuum to afford the title compound as a white solid (2.2 g, 57%), which was used without further purification. 1H NMR (400 MHz, DMSO-d6) 3.66-3.77 (2H, m), 3.88 (3H, s), 4.19-4.32 (2H, m), 6.71 (1H, d), 6.81 (1H, d), 8.74 (1H, s); m/z (ES+), [M+H]+=251; base, HPLC tR=0.46 min.

Preparation of N1-(5-Methoxy-7-(2-methoxyethoxy)quinazolin-4-yl)benzene-1,4-diamine hydrochloride PyAOP (5.5 g, 10.6 mmol) was added to 5-methoxy-7-(2-methoxyethoxy)quinazolin-4(3H)-one (2.2 g, 8.8 mmol) and DBU (2.7 mL, 17.6 mmol) in acetonitrile (100 mL) at 25° C. under nitrogen. The resulting solution was stirred at room temperature for 5 minutes. Benzene-1,4-diamine (1.5 g, 14.1 mmol) was added to this at 25° C. under nitrogen. The resulting solution was stirred at room temperature for 3 hours. The reaction mixture was concentrated and diluted with DCM (500 mL), and washed sequentially with saturated NaHCO$_3$ (100 mL) and saturated aqueous NH$_4$Cl (100 mL). The organic layer was dried, filtered and evaporated to afford crude product. The crude product was purified by flash silica chromatography, elution gradient 0 to 4% methanol in DCM. Pure fractions were evaporated to dryness to afford crude product as a pale yellow oil. The reaction mixture was diluted with HCl (4 M in dioxane, 2 mL) and acetone (10 mL). The precipitate was collected by filtration, washed with acetone (10 mL) and dried under vacuum to afford the title compound as a brown solid. The solid was dissolved in DCM (300 mL), and washed sequentially with saturated NaHCO$_3$ (50 mL). The organic layer was dried, filtered and evaporated to afford the title compound as a yellow solid (1.2 g, 40%). 1H NMR (400 MHz, DMSO-d6) δ 3.33 (3H, s), 3.67-3.74 (2H, m), 4.05 (3H, s), 4.20-4.26 (2H, m), 4.98 (2H, s), 6.58 (2H, d), 6.65 (1H, d), 6.72 (1H, d), 7.33 (2H, d), 8.28 (1H, s), 9.47 (1H, s); m/z (ES+), [M+H]+=341; base, HPLC tR=0.7 min.

Example 21

N-{4-[(5-Fluoro-7-methoxyquinazolin-4-yl)amino]phenyl}-2-[4-(propan-2-yl)-1H-1,2,3-triazol-1-yl]acetamide

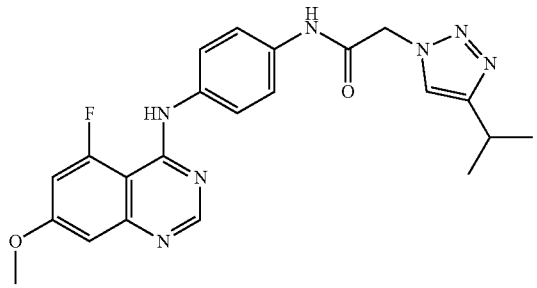 [SMILES: COc1cc(F)c2c(Nc3ccc(NC(=O)Cn4cc(C(C)C)nn4)cc3)ncnc2c1]

HATU (0.3 g, 0.8 mmol) was added to a solution of N1-(5-fluoro-7-methoxyquinazolin-4-yl)benzene-1,4-diamine (0.2 g, 0.7 mmol) and DIPEA (0.5 mL, 2.7 mmol) in DMF (5 mL). The mixture was stirred at ambient temperature for 6 hours. The reaction mixture was poured into water (40 mL) and stirred for 5 minutes. Ethyl acetate (30 mL) was added and the organic layer separated. The aqueous layer was extracted with ethyl acetate (30 mL) and the extracts combined and washed with saturated brine (2×30 mL) and evaporated to dryness. The residue was purified by flash silica chromatography, eluting with a gradient of 0-10% (10:1 ethyl acetate:methanol with 1% NH$_3$) in ethyl acetate. Appropriate fractions were evaporated to dryness to afford the title compound as a white solid (70 mg, 25%). 1H NMR (500 MHz. DMSO, 27° C.) δ 1.24 (3H, s), 1.25 (3H, s), 2.99 (1H, hept), 3.92 (3H, s), 5.26 (2H, s), 7.04 (1H, d), 7.11 (1H, dd), 7.55-7.62 (2H, m), 7.63-7.7 (2H, m), 7.86 (1H, d), 8.45 (1H, s), 8.95 (1H, d), 10.48 (1H, s); m/z: ES+ [M+H]+ 436.

The intermediates used in Example 21 were prepared as follows:

Preparation of 2-Amino-6-fluoro-4-methoxybenzonitrile

Ammonium hydroxide (5.2 mL, 41.4 mmol) was added to a microwave vial containing 2,6-difluoro-4-methoxybenzonitrile (1 g, 5.9 mmol) in isopropanol (1 mL). The resulting solution was sealed and stirred at 80° C. for 16 hours. The reaction mixture was concentrated and ethyl acetate (75 mL) was added. The organic layer were isolated and washed with saturated brine (10 mL) then evaporated to afford the title compound (0.8 g, 86%) which was used without further purification. 1H NMR (500 MHz, DMSO, 27° C.) δ 3.72 (3H, s), 6.11 (1H, dd), 6.15 (1H, dd), 6.36 (2H, s); m/z: ES− [M−H]− 165.

Preparation of (E)-N'-(2-Cyano-3-fluoro-5-methoxyphenyl)-N,N-dimethylformimidamide 1,1-Dimethoxy-N,N-dimethylmethanamine (6.9 ml, 51.8 mmol) was added to 2-amino-6-fluoro-4-methoxybenzonitrile (0.9 g, 5.2 mmol) at 25° C. The resulting slurry was stirred at 80° C. for 2 hours and then cooled to room temperature. Water (10 mL) was added and the reaction mixture stirred for 1 hour. A precipitate formed which was collected by filtration to give the title compound as a pink solid (0.8 g, 72%) which was used without further purification. 1H NMR (500 MHz, DMSO, 27° C.) δ 2.98 (3H, s), 3.07 (3H, s), 3.81 (3H, s), 6.53-6.59 (2H, m), 8.01 (1H, s); m/z: ES+ [M+H]+ 222.

Preparation of 5-Fluoro-7-methoxy-N-(4-nitrophenyl)quinazolin-4-amine

4-Nitroaniline (259 mg, 1.9 mmol) was added to (E)-N'-(2-cyano-3-fluoro-5-methoxyphenyl)-N,N-dimethylformimidamide (277 mg, 1.3 mmol) in acetic acid (7 mL). The resulting solution was stirred at 120° C. for 2 hours. Upon cooling the reaction mixture solidified. Ether (15 mL) was added and the solid slurried for 10 minutes. The resulting yellow solid was collected by filtration, washed with additional ether and dried under vacuum to give the title compound as a tan solid (210 mg, 53%) which was used without further purification. 1H NMR (500 MHz, DMSO, 27° C.) δ 3.95 (3H, s), 7.14 (1H, d), 7.22 (1H, dd), 8.08 (2H, d), 8.21-8.29 (2H, m), 8.66 (1H, s), 9.52 (1H, s); m/z: ES+ [M+H]+ 315.

Preparation of N4-(5-Fluoro-7-methoxy-quinazolin-4-yl)benzene-1,4-diamine

5-Fluoro-7-methoxy-N-(4-nitrophenyl)quinazolin-4-amine (0.2 g, 0.7 mmol) in DMF (8 mL) was added to 10% palladium on carbon (0.07 g, 0.1 mmol) under nitrogen. The reaction mixture was allowed to stir for 24 hours under hydrogen. The reaction mixture was filtered through celite, washed with ethyl acetate (30 mL) and the resulting liquors concentrated to give the title compound as a yellow gum (190 mg, 100%). 1H NMR (500 MHz, DMSO, 27° C.) δ 3.90 (3H, s), 5.01 (2H, s), 6.53-6.60 (2H, m), 6.99 (1H, d), 7.05 (1H, dd), 7.20-7.27 (2H, m), 8.34 (1H, s), 8.67 (1H, d); m/z: ES+ [M+H]+ 285.

Example 22

N-{4-[(5,7-Dimethoxyquinazolin-4-yl)amino]phenyl}-2-[4-(propan-2-yl)-1H-1,2,3-triazol-1-yl]acetamide

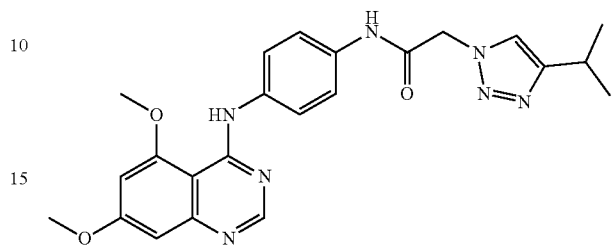

HATU (15.6 g, 40.9 mmol) was added to a mixture of N1-(5,7-dimethoxyquinazolin-4-yl)benzene-1,4-diamine (8.1 g, 27.3 mmol), 2-(4-isopropyl-1H-1,2,3-triazol-1-yl) acetic acid (11.9 g, 34.1 mmol) and DIPEA (14.3 mL, 81.9 mmol) in DMF (250 mL). The mixture was stirred at ambient temperature for 16 hours. The mixture was quenched by the addition of water (20 mL). The resulting solution was concentrated to 100 mL volume and added to a rapidly stirred mixture of ethyl acetate (250 mL) and water (1300 mL). The mixture was stirred for 1 hour. The resulting precipitate was collected by filtration and washed with water (400 mL) to give a beige solid. The solid was treated with with 0.1M NaHCO₃ solution (400 mL) and the resulting suspension was sonicated and stirred for 1 hour. The precipitate was collected by filtration and washed with water. The solid was treated with water (400 mL) and the resulting suspension was sonicated and stirred for 30 minutes. The precipitate was collected by filtration, washed with water and dried to give a beige solid (11.2 g). The solid was recrystallised from acetonitrile (300 mL) to afford the title compound as an off-white semi-crystalline solid (8.8 g, 72%). 1H NMR (500 MHz, DMSO, 27° C.) δ 1.24 (6H, d), 2.99 (1H, hept), 3.89 (3H, s), 4.07 (3H, s), 5.25 (2H, s), 6.68 (1H, d), 6.77 (1H, d), 7.58 (2H, d), 7.76 (2H, d), 7.86 (1H, d), 8.40 (1H, s), 9.76 (1H, s), 10.45 (1H, s); m/z: ES+ [M+H]+ 448.

The intermediates used in Example 22 were prepared as follows:

Preparation of N1-(5,7-Dimethoxyquinazolin-4-yl)benzene-1,4-diamine

DBU (18.8 mL, 126 mmol) was added to a mixture of 5,7-dimethoxyquinazolin-4(3H)-one (10 g, 48.5 mmol) and PyBOP (32.8 g, 63 mmol) in acetonitrile (500 mL). A colourless solution formed that was heated at 60° C. for 1 hour. Benzene-1,4-diamine (10.5 g, 96.9 mmol) was added, and stirring at 60° C. continued for a further 2 hours. The mixture was evaporated and the residue was partitioned between DCM (700 mL) and saturated ammonium chloride solution (600 mL). The organic layer was washed with saturated ammonium chloride solution (300 mL), water (600 mL), saturated NaHCO₃ solution (600 mL) and brine (300 mL), dried and evaporated to dryness. The residue was purified by flash silica chromatography, elution gradient 0 to 6% (10:1 methanol/conc. NH₃ (aq)) in ethyl acetate. Fractions were evaporated to give the crude product (26 g) as brown semi-solid. This solid was dissolved in acetone (400 mL) and HCl in diethyl ether (2M, 25 mL) was added. The resulting solid was collected by filtration and washed with acetone to give the crude product, which was partitioned between saturated NaHCO$_3$ solution (300 mL) and DCM (300 mL). The aqueous layer was extracted with DCM (200 mL) and the extracts combined with the organic layer. The combined organic extracts were filtered through a phase-separating paper and evaporated to dryness. The residue was triturated with diethyl ether to afford the title compound as an orange solid (8 g, 55%). 1H NMR (500 MHz, DMSO, 27° C.) δ 3.87 (3H, s), 4.03 (3H, s), 4.97 (2H, s), 6.57 (2H, d), 6.63 (1H, d), 6.71 (1H, d), 7.31 (2H, d), 8.28 (1H, s), 9.45 (1H, s); m/z: ES+ [M+H]+ 297.

The invention claimed is:

1. A compound of Formula (I):

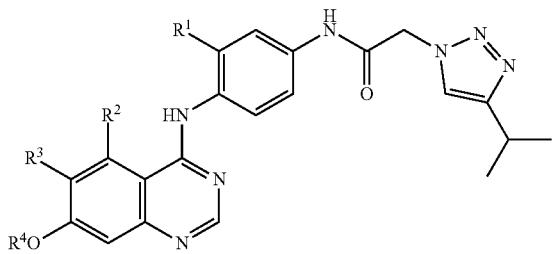

or a pharmaceutically acceptable salt thereof, wherein:
$R^1$ is selected from hydrogen and fluoro;
$R^2$ is selected from fluoro and $C_{1-2}$ alkoxy;
$R^3$ is selected from hydrogen and methoxy; and
$R^4$ is a $C_{1-3}$ alkyl, optionally substituted with a group selected from $C_{1-3}$ alkoxy and $NR^5R^6$, wherein $R^5$ and $R^6$ are each independently hydrogen or methyl; or a 4 to 6 membered heterocyclyl ring containing one oxygen atom.

2. The compound of Formula (I), or a pharmaceutically acceptable salt thereof, as claimed in claim 1, wherein $R^1$ hydrogen.

3. The compound of Formula (I), or a pharmaceutically acceptable salt thereof, as claimed in claim 1, wherein $R^2$ is fluoro.

4. The compound of Formula (I), or a pharmaceutically acceptable salt thereof, as claimed in claim 1, wherein $R^3$ is hydrogen.

5. The compound of Formula (I), or a pharmaceutically acceptable salt thereof, as claimed in claim 1, wherein $R^4$ is selected from methyl, ethyl, isopropyl, oxetanyl, tetrahydrofuranyl, oxanyl, 2-dimethylaminoethyl and 2-methoxyethyl.

6. The compound of Formula (I), or a pharmaceutically acceptable salt thereof, as claimed in claim 5, wherein $R^4$ is 2-methoxyethyl.

7. The compound of Formula (I), or a pharmaceutically acceptable salt thereof, as claimed in claim 1, wherein the compound is selected from the group consisting of:
N-{4-[(5,7-Dimethoxyquinazolin-4-yl)amino]-3-fluorophenyl}-2-[4-(propan-2-yl)-1H-1,2,3-triazol-1-yl]acetamide;
N-{4-[(5-Fluoro-6,7-dimethoxyquinazolin-4-yl)amino]phenyl}-2-[4-(propan-2-yl)-1H-1,2,3-triazol-1-yl]acetamide;
(R)—N-(4-{[5-Ethoxy-7-(tetrahydrofuran-3-yloxy)quinazolin-4-yl]amino}phenyl)-2-[4-(propan-2-yl)-1H-1,2,3-triazol-1-yl]acetamide;
(S)—N-(4-{[5-Ethoxy-7-(tetrahydrofuran-3-yloxy)quinazolin-4-yl]amino}phenyl)-2-[4-(propan-2-yl)-1H-1,2,3-triazol-1-yl]acetamide;
N-(4-((5-Ethoxy-7-((tetrahydro-2H-pyran-4-yl)oxy)quinazolin-4-yl)amino)phenyl)-2-(4-isopropyl-1H-1,2,3-triazol-1-yl)acetamide;
N-(4-((7-(2-(Dimethylamino)ethoxy)-5-ethoxyquinazolin-4-yl)amino)phenyl)-2-(4-isopropyl-1H-1,2,3-triazol-1-yl)acetamide;
N-(4-((5-Ethoxy-7-methoxyquinazolin-4-yl)amino)phenyl)-2-(4-isopropyl-1H-1,2,3-triazol-1-yl)acetamide;
N-(4-((5-Ethoxy-7-(2-methoxyethoxy)quinazolin-4-yl)amino)phenyl)-2-(4-isopropyl-1H-1,2,3-triazol-1-yl)acetamide;
N-(4-((5-Ethoxy-7-(oxetan-3-yloxy)quinazolin-4-yl)amino)phenyl)-2-(4-isopropyl-1H-1,2,3-triazol-1-yl)acetamide;
N-(4-{[5-Methoxy-7-(tetrahydro-2H-pyran-4-yloxy)quinazolin-4-yl]amino}phenyl)-2-[4-(propan-2-yl)-1H-1,2,3-triazol-1-yl]acetamide;
2-[4-(Propan-2-yl)-1H-1,2,3-triazol-1-yl]-N-{4-[(5,6,7-trimethoxyquinazolin-4-yl)amino]phenyl}acetamide;
N-(4-{[5-Fluoro-7-(2-methoxyethoxy)quinazolin-4-yl]amino}phenyl)-2-[4-(propan-2-yl)-1H-1,2,3-triazol-1-yl]acetamide;
(R)-2-(4-Isopropyl-1H-1,2,3-triazol-1-yl)-N-(4-((5-methoxy-7-((tetrahydrofuran-3-yl)oxy)quinazolin-4-yl)amino)phenyl)acetamide;
(S)-2-(4-Isopropyl-1H-1,2,3-triazol-1-yl)-N-(4-((5-methoxy-7-((tetrahydrofuran-3-yl)oxy)quinazolin-4-yl)amino)phenyl)acetamide;
N-(4-{[5-Methoxy-7-(propan-2-yloxy)quinazolin-4-yl]amino}phenyl)-2-[4-(propan-2-yl)-1H-1,2,3-triazol-1-yl]acetamide;
N-(4-{[5-Methoxy-7-(oxetan-3-yloxy)quinazolin-4-yl]amino}phenyl)-2-[4-(propan-2-yl)-1H-1,2,3-triazol-1-yl]acetamide;
N-[4-({7-[2-(Dimethylamino)ethoxy]-5-methoxyquinazolin-4-yl}amino)phenyl]-2-[4-(propan-2-yl)-1H-1,2,3-triazol-1-yl]acetamide;
N-{4-[(7-Ethoxy-5-methoxyquinazolin-4-yl)amino]phenyl}-2-[4-(propan-2-yl)-1H-1,2,3-triazol-1-yl]acetamide;
N-{4-[(5,7-Diethoxyquinazolin-4-yl)amino]phenyl}-2-[4-(propan-2-yl)-1H-1,2,3-triazol-1-yl]acetamide;
N-(4-{[5-Methoxy-7-(2-methoxyethoxy)quinazolin-4-yl]amino}phenyl)-2-[4-(propan-2-yl)-1H-1,2,3-triazol-1-yl]acetamide;
N-{4-[(5-Fluoro-7-methoxyquinazolin-4-yl)amino]phenyl}-2-[4-(propan-2-yl)-1H-1,2,3-triazol-1-yl]acetamide; and
N-{4-[(5,7-Dimethoxyquinazolin-4-yl)amino]phenyl}-2-[4-(propan-2-yl)-1H-1,2,3-triazol-1-yl]acetamide.

8. A pharmaceutical composition which comprises a compound of Formula (I), or a pharmaceutically acceptable salt thereof, as claimed in claim 1, and at least one pharmaceutically acceptable diluent or carrier.

9. A method for treating cancer in a warm-blooded animal in need of such treatment, which comprises administering to the warm-blooded animal a therapeutically effective amount of a compound of Formula (I), or a pharmaceutically acceptable salt thereof, as claimed in claim 1, and wherein the cancer is selected from the group consisting of gastrointestinal stromal tumour, melanoma, lung cancer, glioblastoma, leukemias, testicular carcinomas, and head and neck cancers.

10. N-(4-{[5-Fluoro-7-(2-methoxyethoxy)quinazolin-4-yl]amino}phenyl)-2-[4-(propan-2-yl)-1H-1,2,3-triazol-1-yl]acetamide.

11. A pharmaceutically acceptable salt of N-(4-{[5-Fluoro-7-(2-methoxy-ethoxy)quinazolin-4-yl]amino}phenyl)-2-[4-(propan-2-yl)-1H-1,2,3-triazol-1-yl]acetamide.

12. The pharmaceutically acceptable salt, as claimed in claim 11, wherein the salt is a tosylate salt of N-(4-{[5-Fluoro-7-(2-methoxyethoxy)quinazolin-4-yl]-amino}phenyl)-2-[4-(propan-2-yl)-1H-1,2,3-triazol-1-yl]acetamide.

13. A pharmaceutical composition which comprises N-(4-{[5-Fluoro-7-(2-methoxyethoxy)quinazolin-4-yl]amino}phenyl)-2-[4-(propan-2-yl)-1H-1,2,3-triazol-1-yl]-acetamide, or a pharmaceutically acceptable salt thereof, and at least one pharmaceutically acceptable diluent or carrier.

14. The pharmaceutical composition, as claimed in claim 13, wherein the composition comprises N-(4-{[5-Fluoro-7-(2-methoxyethoxy)quinazolin-4-yl]amino}-phenyl)-2-[4-(propan-2-yl)-1H-1,2,3-triazol-1-yl]acetamide.

15. The pharmaceutical composition, as claimed in claim 13, wherein the composition comprises a pharmaceutically acceptable salt of N-(4-{[5-Fluoro-7-(2-methoxyethoxy)quinazolin-4-yl]amino}phenyl)-2-[4-(propan-2-yl)-1H-1,2,3-triazol-1-yl]-acetamide.

16. The pharmaceutical composition, as claimed in claim 13, wherein the composition comprises a pharmaceutically acceptable tosylate salt of N-(4-{[5-Fluoro-7-(2-methoxy-ethoxy)quinazolin-4-yl]amino}phenyl)-2-[4-(propan-2-yl)-1H-1,2,3-triazol-1-yl]-acetamide.

17. The pharmaceutical composition, as claimed in claim 13, wherein the composition is an oral pharmaceutical composition.

18. A method for treating cancer in a human in need of such treatment, which comprises administering to the human a therapeutically effective amount of N-(4-{[5-Fluoro-7-(2-methoxyethoxy)quinazolin-4-yl]amino}phenyl)-2-[4-(propan-2-yl)-1H-1,2,3-triazol-1-yl]acetamide, or a pharmaceutically acceptable salt thereof, and wherein the cancer is selected from the group consisting of gastrointestinal stromal tumour, melanoma, lung cancers, glioblastoma, leukemias, testicular carcinomas, and head and neck cancers.

19. The method of treating, as claimed in claim 18, wherein the cancer is gastrointestinal stromal tumour.

20. The method of treating, as claimed in claim 18, wherein the cancer is glioblastoma.

21. The method of treating, as claimed in claim 18, wherein the cancer is lung cancer.

22. The method of treating, as claimed in claim 21, wherein the lung cancer is squamous carcinoma of the lung.

23. The method of treating, as claimed in claim 18, wherein the cancer is leukemia.

24. The method of treating, as claimed in claim 18, wherein the leukemia is acute myeloid leukaemia or mast cell leukemia.

* * * * *